(12) United States Patent
Dumas et al.

(10) Patent No.: US 7,977,333 B2
(45) Date of Patent: *Jul. 12, 2011

(54) SUBSTITUTED PYRIDINES AND PYRIDAZINES WITH ANGIOGENESIS INHIBITING ACTIVITY

(75) Inventors: Jacques P. Dumas, Bethany, CT (US); Stephen J. Boyer, Hilden (DE); Julie A. Dixon, Bethany, CT (US); Teddy K. Joe, San Francisco, CA (US); Harold C. E. Kluender, Trumbull, CT (US); Wendy Lee, Hamden, CT (US); Dhanapalan Nagarathnam, Bethany, CT (US); Robert N. Sibley, North Haven, CT (US); Ning Su, Hamden, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 1959 days.

This patent is subject to a terminal disclaimer.

(21) Appl. No.: 10/720,702

(22) Filed: Nov. 24, 2003

(65) Prior Publication Data

US 2004/0092740 A1     May 13, 2004

Related U.S. Application Data

(62) Division of application No. 09/672,294, filed on Sep. 27, 2000, now Pat. No. 6,689,883.

(60) Provisional application No. 60/287,595, filed on Apr. 20, 2000.

(51) Int. Cl.
*A61K 31/535* (2006.01)
*A61K 31/50* (2006.01)
*C07D 237/30* (2006.01)
*C07D 237/32* (2006.01)
*C07D 237/34* (2006.01)
*C07D 413/14* (2006.01)

(52) U.S. Cl. ............. 514/248; 514/234.5; 544/116; 544/119; 544/231; 544/235; 544/236; 544/237

(58) Field of Classification Search .......... 544/231, 544/235, 236, 237, 116, 119; 514/248, 234.5
See application file for complete search history.

(56) References Cited

U.S. PATENT DOCUMENTS

| | | | |
|---|---|---|---|
| 3,478,028 A | 11/1969 | Parsons et al. | |
| 3,753,988 A | 8/1973 | Rodway et al. | |
| 3,764,598 A * | 10/1973 | Yurugi et al. | 544/81 |
| 5,089,494 A | 2/1992 | Iwase et al. | |
| 5,324,727 A | 6/1994 | Iwase et al. | |
| 5,849,741 A * | 12/1998 | Watanabe et al. | 514/248 |
| 6,288,064 B1 | 9/2001 | Watanabe et al. | |
| 6,689,883 B1 * | 2/2004 | Dumas et al. | 544/235 |

FOREIGN PATENT DOCUMENTS

| | | |
|---|---|---|
| EP | 0534443 A1 | 9/1993 |
| EP | 0722936 | 7/1996 |
| EP | 0920868 | 8/1997 |
| EP | 0682947 | 9/1997 |
| EP | 0534443 B1 | 12/1998 |
| FR | 1453897 | 9/1966 |
| FR | 1516777 | 3/1968 |
| JP | 3106875 | 7/1991 |
| WO | WO 0009495 | 2/1998 |
| WO | WO 9835958 | 8/1998 |
| WO | WO 9852944 | 11/1998 |
| WO | WO 9858929 | 12/1998 |
| WO | WO 9911628 | 2/1999 |
| WO | WO 9962908 | 12/1999 |
| WO | WO 0059509 | 10/2000 |
| WO | WO 0110859 | 2/2001 |

OTHER PUBLICATIONS

Biagi et al., Chemical Abstracts, vol. 126:89328, 1996.
Biagi et al., Chemical Abstracts, vol. 123:83329, 1995.
Biagli et al., Chemical Abstracts, vol. 123:111969, 1995.
Monge et al., Chemical Abstracts, vol. 120:95169, 1994.
Marchard et al., Chemical Abstracts, vol. 114:42612, 1991.
Andersen et al., Chemical Abstracts, vol. 112:55749, 1990.
Suzuki et al., Chemical Abstracts, vol. 90:152107, 1979.
Mitsuhashi et al., Chemical Abstracts, vol. 84:180170, 1976.
Sieja, Chemical Abstracts, vol. 78:137957, 1973.
Pons et al., Chemical Abstracts, vol. 71:81350, (1969).
Howe et al., Chemical Abstracts, vol. 71:21922, (1969).
Robba et al., Chemical Abstracts, vol. 69:10411, (1968).
Robba et al., Chemical Abstracts, vol. 66:95066, (1967).
Robba et al., Chemical Abstracts, vol. 66:94981, (1967).
Desimoni et al., Chemical Abstracts, vol. 66:55454, (1967).

(Continued)

*Primary Examiner* — Peter G O'Sullivan
(74) *Attorney, Agent, or Firm* — Edwards Angell Palmer & Dodge LLP; Ralph A. Loren; Nicholas J. DiCeglie, Jr.

(57) ABSTRACT

Substituted and pyridines and pyridazines having angiogenesis inhibiting activity and the generalized structural formula

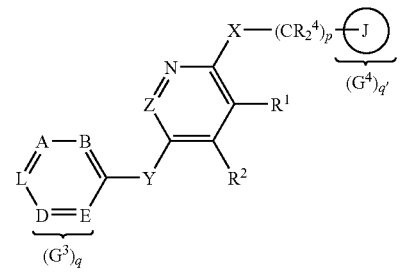

wherein the ring containing A, B, D, E, and L is phenyl or a nitrogen-containing heterocycle; groups X and Y may be any of a variety of defined linking units; $R^1$ and $R^2$ may be defined independent substituents or together may be a ring-defining bridge; ring J may be an aryl, pyridyl, or cycloalkyl group; and G groups may be any of a variety of defined substituents. Pharmaceutical compositions containing these materials, and methods of treating a mammal having a condition characterized by abnormal angiogenesis or hyperpermiability processes using these materials are also disclosed.

7 Claims, No Drawings

OTHER PUBLICATIONS

Chemical Abstract: 15:256197; Uenishi, Keiji et al. "Preparations of 1(3-pyridylmethyl) phthalazines as blood platelet aggregation inhibitors",Jpn.Kokai Tokkyo Koho, 6 pp 1992.

Ferrara, N. et al., "Molecular and Biological Properties of the Vascular Endothelial Growth Factor Family of Proteins", Endocrine Reviews, 13, 18-32 (1992).

Neufeld, G. et al., "Vascular endothelial growth factor (VDGF) and its receptors". FASEB J., 13, 9-22 (1999).

Shweiki, D. et al., "Vascular Endothelial growth factor induced by hypoxia may mediate hypoxia-initated angiogenesis". Nature, 359, 843-848, (1992).

Mustonen, T. and Alitalo K., "Endothelial Receptor Tyrosine Kinases Involved in Angiogenesis". Cell Biology, 129, 895-898 (1995).

Waltenberger, J. et al., "Different Signal Transduction Properties of KDR and Flt1, Two Receptors for Vascular Endothelial Growth Factor" J. Biol. Chem. 269, 26988-26995, 1994.

Seetharan, L. et al., "A unique signal transduction from FLT tyrosine kinase, a receptor for vascular endothelial growth factor VEGF". Oncogene, 10, 135-147 (1995).

Shweiki, D. et al., "Induction of vascular endothelial growth factor expression by hypoxia and by glucose deficiency in multicell spheroids: Implications for tumor angiogenesis". Proc. Nat'l. Acad. Sci. USA, 92, 768-772 (1995).

Grugel, S. et al., "Both v-Ha-Ras and v-Raf Stimulate Expression of the Vascular Endothelial Growth Factor in NIH 3T3 Cells," J. Biol. Chem., 270, 25915-25919 (1995).

Rak, J. et al., "Mutant ras Oncogenes Upregulate VEGF/VPF Expression: Implications for Induction and Inhibition of Tumor Angiogenesis." Cancer Research 55, 4575-4580 (1995).

Mattern, J., et al., "Association of vascular endothelial growth factor expression with intratumoral microvessel density and tumour cell proliferation in human epidermoid lung carcinoma." Brit. J. Cancer, 73, 931-934 (1996).

Viglietto, G. et al., "Upregulation of vascular endothelial growth factor (VDGF) and downregulation of placenta growth factor (PIGF) associated with malignancy injuman thyroid tumors and cell lines". Oncogene, 11, 1569-1579 (1995).

Brown, L. et al., "Expression of Vascular Permeability Factor (Vascular Endothelial Growth Factor) and its Receptors in Breast Cancer". Human Pathology, 26, 86-91 (1995).

Brown, L. et al., "Expression of Vascular Permeability Factor (Vascular Endothethiel Growth Factor) and its Receptors in Adrenocarinomas of the Gastrointestinal Tract". Cancer Research 53, 4727-4735 (1993).

Suzuki, K. et al., "Expression of Vascular Permeability Factor/Vascular Endothelial Growth Factor in Human Hepatocellular Carcinoma", Cancer Research, 56, 3004-3009 (1996).

Brown, L, et al., "Increased Expression of Vascular Permeability Factor (Vascular Endothelial growth Factor) and its Receptors in Kidney and Bladder Carcinomas", Am. J. Pathology, 143, 1255-1262 (1993).

Olson, T. et al., "Vascular Permeability Factor Gene Expression in Normal and Neoplastic Human Ovaries", Cancer Research, 54, 276-280 (1994).

Guidi, A. J. et al., "Vascular Permeability Factor (Vascular Endothelial Growth Factor) Expression and Angiogenesis in Cervical Neoplasia", J. Nat'l. Cancer Institute, 87; 1237-1245 (1995).

Hashimoto, M. et al., "Expression of Vascular Endothelial Growth Factor and its Receptor mRNA in Angiosarcoma". Laboratory Investigation, 83, 859-863, (1995).

Plate, Karl H. et al., "Vascular endothelial growth factor is a potential tumour angiogenesis factor in human gliomas in vivo". Nature, 359, 845-848 (1992).

Phillips, Heidi S. et al., "Intense focal expression of vascular endothelial growth factor mRNA in human intracranial neoplasms: association with regions of necrosis". Int. J. Oncology, 2, 913-919 (1993).

Berkman, Richard A., et al., "Expression of the Vascular Permeability Factor/Vascular Endothethial Growth Factor Gene in Central Nervous System Neoplasms", J. Clin. Invest. 91, 153-159 (1993).

Kim K. Jin, et al., "Inhibition of Vascular Endothelial Growth Factor-Induced Angiogenesis Suppresses Tumour Growth in vivo," Nature, 362, 841-844 (1993).

Rockwell, P. and Goldstein, N. I., "Role of Protein Tyrosine Kinase Receptors in Cancer; Possibilities for Therapeutic Intervention", Mol. And Cell. Differ., 3, 315-335 (1995).

Aiello, L. P., et al., "Vascular Endothelial Growth Factor in Ocular Fluid of Patients with Diabetic Retinopathy and other Retinal Disorders". New England J. Med., 331, 1480-1487 (1994).

Pe'er, J., et al., "Hypoxia-Induced Expression of Vascular Endothelial Growth Factor by Retinal Cells is a Common Factor in Neovascularizing Ocular Diseases", Lab. Invest., 72, 638-645 (1995).

Lopez, P. F. et al., "Transdifferentitated Retinal pigment Epithelial Cells are Immunoreactive for Vascular Endothelial Growth Factor in Surgically Excised Age-Related Macular Degeneration-Related Choroidal Neovascular Membranes". Invest Opthamol. Vis. Sci., 37, 855-868 (1996).

Koch, A. E. et al., "Vascular Endothelial Growth Factor: A Cytokine Modulating Endothelial Function in Rheumatoid Arthritis," J. Immunol., 152, 4149-4156 (1994).

Peacock, D. J., et al., "Angiogenesis Inhibition Suppresses Collagen Arthritis", J. Exp. Med., 175, 1135-1138, (1992).

Brown, L., et al., "Increased Expression of Vascular Permeability Factor (Vascular Endothelial Growth Factor) in Bullous Pemphigoid, Dermatities Herpetiformis, and Erythema Multiforme", J. Invest. Dermatol., 194, 744-749 (1995).

El-Feky, S.A.., "Phthalazine Derivatives from 1-Hydrazino 4-Benzyl (or Methyl) Phthalizine", Egypt J. Chem., 33, 189-197 (1990).

Duhault, J. et al., "Etude D'Hydrazones Heterocycliques de Pyridoxal Phosphate. Comportement Coenzymatique", Bull Soc. Chim. Biol. 49, 177-0190 (1967).

Holava, H.M. and Partyka, R.A., "1-Substituted 4-Aryl-(or 4-Arylalkyl-) Phthalazines", J. Med. Chem, 12, 555-556 (1969).

Gerhardt, et al., Imidazo[4,5,d]pyridazines. IV. Synthesis Of 4,7-Disubstituted Derivatives and 1-Benzyl-2-Substituted Thio Derivatives, J. Heterocyclic Chem., 2, 247-252 (1965).

Malm, et al., Imidazo[4,5,d]pyridazines. III. The Synthesis of 2-Phenylimidazo[4,5,d]pyridazines. J. Heterocyclic Chem., 1, 182-185 (1964).

Laursen, et al., Synthesis of 2,4,7-Trichloroimidazo[4,5,d]pyridazine and Certain of its Derivatives. J. Org Chem., 27, 2500-2504 (1962).

Biagi, et al., 1,2,3- Triazole[4,5-d]pyridazines—IV. Preparation and Adenosine Receptor Binding of New 4 and/or 7 Amino-derivatives. II Farmaco, 50, 99-105 (1995).

Majcen, et al., Pyridazines., LXIX. Annealation of an azole ring to 1,2,5-Thiadiazolo[3,4-d]pyridazine. Chem. Abstracts 83: 79175f (1975).

Robba et al., Thieno[2,3-d]pyridazines and thieno[3,4-d]pyridazines. Chem. Abstracts 69:10411y (1968).

Desimoni, et al., Polynuclear isoxazole types II. Isoxazolo[4,5-d]pyridazines. Chem. Abstracts 66: 5545u (1967).

* cited by examiner

SUBSTITUTED PYRIDINES AND PYRIDAZINES WITH ANGIOGENESIS INHIBITING ACTIVITY

FIELD

This application relates to small molecule heterocyclic pharmaceuticals, and more particularly, to substituted pyridines and pyridazines having angiogenesis inhibiting activity.

BACKGROUND

Vasculogenesis involves the de novo formation of blood vessels from endothelial cell precursors or angioblasts. The first vascular structures in the embryo are formed by vasculogenesis. Angiogenesis involves the development of capillaries from existing blood vessels, and is the principle mechanism by which organs, such as the brain and the kidney are vascularized. While vasculogenesis is restricted to embryonic development, angiogenesis can occur in the adult, for example during pregnancy, the female cycle, or wound healing.

One major regulator of angiogenesis and vasculogenesis in both embryonic development and some angiogenic-dependent diseases is vascular endothelial growth factor (VEGF; also called vascular permeability factor, VPF). VEGF represents a family of mitogens isoforms resulting from alternative mRNA splicing and which exist in homodimeric forms. The VEGF KDR receptor is highly specific for vascular endothelial cells (for reviews, see: Farrara et al. *Endocr. Rev.* 1992, 13, 18; Neufield et al. *FASEB J.* 1999, 13, 9).

VEGF expression is induced by hypoxia (Shweiki et al. *Nature* 1992, 359, 843), as well as by a variety of cytokines and growth factors, such as interleukin-1, interleukin-6, epidermal growth factor and transforming growth factor-α and -β.

To date VEGF and the VEGF family members have been reported to bind to one or more of three transmembrane receptor tyrosine kinases (Mustonen et al. *J. Cell Biol.*, 1995, 129, 895), VEGF receptor-1 (also known as flt-1 (fms-like tyrosine kinase-1)); VEGFR-2 (also known as kinase insert domain containing receptor (KDR), the murine analogue of KDR being known as fetal liver kinase-1 (flk-1)); and VEGFR-3 (also known as flt-4). KDR and fit-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependent tyrosine phosphorylation in intact cells, whereas flt-1 displays a weaker response. Thus, binding to KDR is a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. Regulation of the VEGF-mediated signal transduction cascade will therefore provide a useful mode for control of abnormal angiogenesis and/or hyperpermeability processes.

Angiogenesis is regarded as an absolute prerequisite for growth of tumors beyond about 1-2 mm. Oxygen and nutrients may be supplied to cells in tumors smaller than this limit through diffusion. However, every tumor is dependent on angiogenesis for continued growth after it has reached a certain size. Tumorigenic cells within hypoxic regions of tumors respond by stimulation of VEGF production, which triggers activation of quiescent endothelial cells to stimulate new blood vessel formation. (Shweiki et al. *Proc. Nat'l. Acad. Sci.*, 1995, 92, 768). In addition, VEGF production in tumor regions where there is no angiogenesis may proceed through the ras signal transduction pathway (Grugel et al. *J. Biol. Chem.*, 1995, 270, 25915; Rak et al. *Cancer Res.* 1995, 55, 4575). In situ hybridization studies have demonstrated VEGF mRNA is strongly upregulated in a wide variety of human tumors, including lung (Mattern et al. *Br. J. Cancer* 1996, 73, 931), thyroid (Viglietto et al. *Oncogene* 1995, 11, 1569), breast (Brown et al. *Human Pathol.* 1995, 26, 86), gastrointestinal tract (Brown et al. *Cancer Res.* 1993, 53, 4727; Suzuki et al. *Cancer Res.* 1996, 56, 3004), kidney and bladder (Brown et al. *Am. J. Pathol.* 1993, 143I, 1255), ovary (Olson et al. *Cancer Res.* 1994, 54, 1255), and cervical (Guidi et al. *J. Nat'l Cancer Inst.* 1995, 87, 12137) carcinomas, as well as angiosacroma (Hashimoto et al. *Lab. Invest.* 1995, 73, 859) and several intracranial tumors (Plate et al. *Nature* 1992, 359, 845; Phillips et al. *Int. J. Oncol.* 1993, 2, 913; Berkman et al. *J. Clin. Invest.*, 1993, 91, 153). Neutralizing monoclonal antibodies to KDR have been shown to be efficacious in blocking tumor angiogenesis (Kim et al. *Nature* 1993, 362, 841; Rockwell et al. *Mol. Cell. Differ.* 1995, 3, 315).

Overexpression of VEGF, for example under conditions of extreme hypoxia, can lead to intraocular angiogenesis, resulting in hyperproliferation of blood vessels, leading eventually to blindness. Such a cascade of events has been observed for a number of retinopathies, including diabetic retinopathy, ischemic retinal-vein occlusion, retinopathy of prematurity (Aiello et al. *New Engl. J. Med.* 1994, 331, 1480; Peer et al. *Lab. Invest.* 1995, 72, 638), and age-related macular degeneration (AMD; see, Lopez et al. *Invest. Opthlhalmol. Vis. Sci.* 1996, 37, 855).

In rheumatoid arthritis (RA), the in-growth of vascular pannus may be mediated by production of angiogenic factors. Levels of immunoreactive VEGF are high in the synovial fluid of RA patients, while VEGF levels were low in the synovial fluid of patients with other forms of arthritis of with degenerative joint disease (Koch et al. *J. Immunol.* 1994, 152, 4149). The angiogenesis inhibitor AGM-170 has been shown to prevent neovascularization of the joint in the rat collagen arthritis model (Peacock et al. *J. Exper. Med.* 1992, 175, 1135).

Increased VEGF expression has also been shown in psoriatic skin, as well as bullous disorders associated with subepidermal blister formation, such as bullous pemphigoid, erythema multiforme, and dermatitis herpetiformis (Brown et al. *J. Invest. Dermatol.* 1995, 104, 744).

Because inhibition of KDR signal transduction leads to inhibition of VEGF-mediated angiogenesis and permeabilization, KDR inhibitors will be useful in treatment of diseases characterized by abnormal angiogenesis and/or hyperpermeability processes, including the above listed diseases Examples of phthalazines and other fused pyridazines that are similar in structure to those of the present application are disclosed in the following patents or patent applications: WO 9835958 (Novartis), U.S. Pat. No. 5,849,741, U.S. Pat. No. 3,753,988, U.S. Pat. No. 3,478,028 and JP 03106875. Other literature references to phthalazines are El-Feky, S. A., Bayoumy, B. E., and Abd El-Sami, Z. K., Egypt. J. Chem. (1991), Volume Date 1990, 33(2), 189-197; Duhault, J., Gonnard, P., and Fenard, S., Bull. Soc. Chim. Biol., (1967), 49 (2), 177-190; and Holava, H. M. and Jr, Partyka, R. A., J. Med. Chem., (1969), 12, 555-556. The compounds of the present invention are distinct from those described in each of the above references, and only the Novartis publication describes such compounds as inhibitors of angiogenesis.

As explained above, compounds which inhibit angiogenesis have applicability in treatment of a variety of medical conditions, and are therefore desirable. Such materials are the subject of the present application.

SUMMARY

In its broadest aspect, the present invention relates to the sum of three sets of chemical compounds, or pharmaceutically acceptable salts or prodrugs thereof, with each set overlapping the others in scope. The generalized structural formula for the compounds in each of the three sets of compounds is the same, but it should be noted that the definitions of the several groups comprising the general structure in each set differ somewhat. Thus, the defined sets of chemical compounds differ from each other, but overlap in their scopes.

The first set of compounds have the generalized structural formula

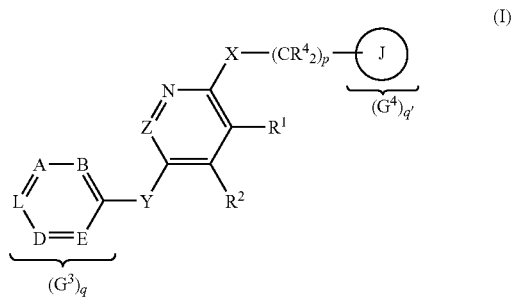

(I)

wherein
$R^1$ and $R^2$
together form a bridge containing two $T^2$ moieties and one $T^3$ moiety, said bridge, taken together with the ring to which it is attached, forming a bicyclic of structure

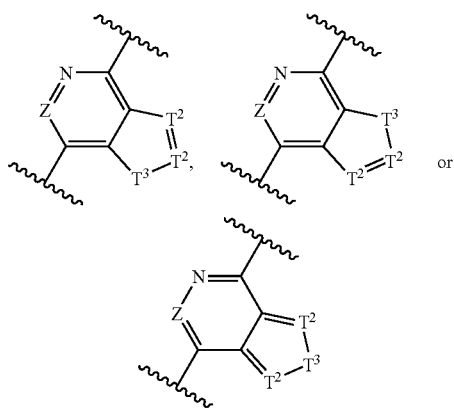

wherein
each $T^2$ independently represents N, CH, or $CG^1$;
$T^3$ represents S, O, $CR^4G^1$, $C(R^4)_2$, or $NR^3$.

In the above substructures, $G^1$ is a substituent independently selected from the group consisting of —$N(R^6)_2$; —$NR^3COR^6$; halogen; alkyl; cycloalkyl; lower alkenyl; lower cycloalkenyl; halogen-substituted alkyl; amino-substituted alkyl; N-lower alkylamino-substituted alkyl; N,N-di-lower alkylamino-substituted alkyl; N-lower alkanoylamino-substituted alkyl; hydroxy-substituted alkyl; cyano-substituted alkyl; carboxy-substituted alkyl; lower alkoxycarbonyl-substituted alkyl; phenyl lower alkoxycarbonyl-substituted alkyl; halogen-substituted alkylamino; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; cyano-substituted alkylamino; carboxy-substituted alkylamino; lower alkoxycarbonyl-substituted alkylamino; phenyl-lower alkoxycarbonyl-substituted alkylamino; —$OR^6$; —$SR^6$; —$S(O)R^6$; —$S(O)_2R^6$; halogenated lower alkoxy; halogenated lower alkylthio; halogenated lower alkylsulfonyl; —$OCOR^6$; —$COR^6$; —$CO_2R^6$; —$CON(R^6)_2$; —$CH_2OR^3$; —$NO_2$; —CN; amidino; guanidino; sulfo; —$B(OH)_2$; optionally substituted aryl; optionally substituted heteroaryl; optionally substituted saturated heterocyclyl; optionally substituted saturated heterocyclylalkyl; optionally substituted partially unsaturated heterocyclyl; optionally substituted partially unsaturated heterocyclylalkyl; —$OCO_2R^3$; optionally substituted heteroarylalkyl; optionally substituted heteroaryloxy; —$S(O)_p$ (optionally substituted heteroaryl); optionally substituted heteroarylalkyloxy; —$S(O)_p$ (optionally substituted heteroarylalkyl); —CHO; —$OCON(R^6)_2$; —$NR^3CO_2R^6$; and —$NR^3CON(R^6)_2$.

The group $R^3$ is H or lower alkyl. $R^6$ is independently selected from the group consisting of H; alkyl; cycloalkyl; optionally substituted aryl; optionally substituted aryl lower alkyl, lower alkyl-$N(R^3)_2$, and lower alkyl-OH.

In generalized structural formula (I), $R^4$ is H, halogen, or lower alkyl. The subscript p is 0, 1, or 2; and X is selected from the group consisting of O, S, and $NR^3$.

The linking moiety Y is selected from the group consisting of lower alkylene; —$CH_2$—O—; —$CH_2$—S—; —$CH_2$—NH—; —O—; —S—; —NH—; —O—$CH_2$—; —S(O)—; —$S(O)_2$—; —$SCH_2$—; —$S(O)CH_2$—; —$S(O)_2CH_2$—; —$CH_2S(O)$—; —$CH_2S(O)_2$; —$(CR^4_2)_n$—$S(O)_p$-(5-membered heteroaryl)-$(CR^4_2)_s$—; and —$(CR^4_2)_n$—$C(G^2)(R^4)$—$(CR^4_2)_s$—. In the latter two linking groups Y, n and s are each independently 0 or an integer of 1-2. The substituent $G^2$ is selected from the group consisting of —CN, —$CO_2R^3$, —$CON(R^6)_2$, and —$CH_2N(R^6)_2$.

Z represents $CR^4$ or N.

Regarding the ring containing A, B, D, E, and L, the number of possible substituents $G^3$ on the ring is indicated by subscript q, which is 0, 1, or 2.

Substituent moieties $G^3$ are monovalent or bivalent moieties selected from the group consisting of: lower alkyl; —$NR^3COR^6$; carboxy-substituted alkyl; lower alkoxycarbonyl-substituted alkyl; —$OR^6$; —$SR^6$; —$S(O)R^6$; —$S(O)_2R^6$; —$OCOR^6$; —$COR^6$; —$CO_2R^6$; —$CH_2OR^3$; —$CON(R^6)_2$; —$S(O)_2N(R^6)_2$; —$NO_2$; —CN; optionally substituted aryl; optionally substituted heteroaryl; optionally substituted saturated heterocyclyl; optionally substituted partially unsaturated heterocyclyl; optionally substituted heteroarylalkyl; optionally substituted heteroaryloxy; —$S(O)_p$ (optionally substituted heteroaryl); optionally substituted heteroarylalkyloxy; —$S(O)_p$ (optionally substituted heteroarylalkyl); —$OCON(R^6)_2$; —$NR^3CO_2R^6$; —$NR^3CON(R^6)_2$; and bivalent bridge of structure $T^2$=$T^2$-$T^3$. In this bivalent bridge, each $T^2$ independently represents N, CH, or $CG^{3'}$; and $T^3$ represents S, O, $CR^4G^{3'}$, $C(R^4)_2$, or $NR^3$. $G^{3'}$ represents any of the above-defined moieties $G^3$ which are monovalent; and the terminal $T^2$ of the bridge is bound to L, and $T^3$ is bound to D, thus forming a 5-membered fused ring.

In the ring shown at the left in generalized structural formula (I), A and D independently represent N or CH; B and E independently represent N or CH; and L represents N or CH; with the provisos that a) the total number of N atoms in the ring containing A, B, D, E, and L is 0, 1, 2, or 3; b) when L represents CH and any $G^3$ is a monovalent substituent, at least one of A and D is an N atom; and c) when L represents CH and a $G^3$ is a bivalent bridge of structure $T^2=T^2-T^3$, then A, B, D, and E are also CH.

J is a ring selected from the group consisting of aryl; pyridyl; and cycloalkyl. The subscript q' represents the number of substituents $G^4$ on ring J and is 0, 1, 2, 3, 4, or 5.

The possible substituents $G^4$ on ring J are monovalent or bivalent moieties selected from the group consisting of —N($R^6$)$_2$; —$NR^3COR^6$; halogen; alkyl; cycloalkyl; lower alkenyl; lower cycloalkenyl; halogen-substituted alkyl; amino-substituted alkyl; N-lower alkylamino-substituted alkyl; N,N-di-lower alkylamino-substituted alkyl; N-lower alkanoylamino-substituted alkyl; hydroxy-substituted alkyl; cyano-substituted alkyl; carboxy-substituted alkyl; lower alkoxycarbonyl-substituted alkyl; phenyl lower alkoxycarbonyl-substituted alkyl; halogen-substituted alkylamino; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; cyano-substituted alkylamino; carboxy-substituted alkylamino; lower alkoxycarbonyl-substituted alkylamino; phenyl-lower alkoxycarbonyl-substituted alkylamino; —$OR^6$; —$SR^6$; —S(O)$R^6$; —S(O)$_2$$R^6$; halogenated lower alkoxy; halogenated lower alkylthio; halogenated lower alkylsulfonyl; —$OCOR^6$; —$COR^6$; —$CO_2R^6$; —CON($R^6$)$_2$; —$CH_2OR^3$; —$NO_2$; —CN; amidino; guanidino; sulfo; —B(OH)$_2$; optionally substituted aryl; optionally substituted heteroaryl; optionally substituted saturated heterocyclyl; optionally substituted partially unsaturated heterocyclyl; —$OCO_2R^3$; optionally substituted heteroarylalkyl; optionally substituted heteroaryloxy; —S(O)$_p$ (optionally substituted heteroaryl); optionally substituted heteroarylalkyloxy; —S(O)$_p$ (optionally substituted heteroarylalkyl); —CHO; —OCON($R^6$)$_2$; —$NR^3CO_2R^6$; —$NR^3CON(R^6)_2$; and fused ring-forming bivalent bridges attached to and connecting adjacent positions of ring J, said bridges having the structures:

a)

wherein each $T^2$ independently represents N, CH, or $CG^{4'}$; $T^3$ represents S, O, $CR^4G^{4'}$, $C(R^4)_2$, or $NR^3$; G4' represents any of the above-defined moieties $G^4$ which are monovalent; and binding to ring J is achieved via terminal atoms $T^2$ and $T^3$;

b)

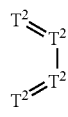

wherein each $T^2$ independently represents N, CH, or $CG^{4'}$; G4' represents any of the above-defined moieties $G^4$ which are monovalent; with the proviso that a maximum of two bridge atoms $T^2$ may be N; and binding to ring J is achieved via terminal atoms $T^2$; and c)

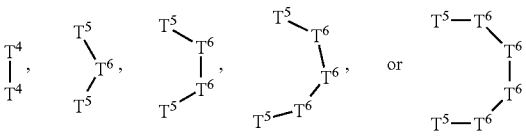

wherein each $T^4$, $T^5$, and $T^6$ independently represents O, S, $CR^4G^{4'}$, $C(R^4)_2$, or $NR^3$; $G^{4'}$ represents any of the above-defined moieties G which are monovalent; and binding to ring J is achieved via terminal atoms $T^4$ or $T^5$; with the provisos that:
  i) when one $T^4$ is O, S, or $NR^3$, the other $T^4$ is $CR^4G^{4'}$ or $C(R^4)_2$;
  ii) a bridge comprising $T^5$ and $T^6$ atoms may contain a maximum of two heteroatoms O, S, or N; and
  iii) in a bridge comprising $T^5$ and $T^6$ atoms, when one $T^5$ group and one $T^6$ group are O atoms, or two $T^6$ groups are O atoms, said O atoms are separated by at least one carbon atom.

When $G^4$ is an alkyl group located on ring J adjacent to the linkage —(CR$^4$$_2$)$_p$—, and X is $NR^3$ wherein $R^3$ is an alkyl substituent, then $G^4$ and the alkyl substituent $R^3$ on X may be joined to form a bridge of structure —(CH$_2$)$_{p'}$— wherein p' is 2, 3, or 4, with the proviso that the sum of p and p' is 2, 3, or 4, resulting in formation of a nitrogen-containing ring of 5, 6, or 7 members.

Additional provisos are that: 1) in $G^1$, $G^2$, $G^3$, and $G^4$, when two groups $R^3$ or $R^6$ are each alkyl and located on the same N atom they may be linked by a bond, an O, an S, or $NR^3$ to form a N-containing heterocycle of 5-7 ring atoms; and 2) when an aryl, heteroaryl, or heterocyclyl ring is optionally substituted, that ring may bear up to substituents which are independently selected from the group consisting of amino, mono-lower-alkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —$CO_2R^3$, —CHO, —$CH_2OR^3$, —$OCO_2R^3$, —CON($R^6$)$_2$, —OCON($R^6$)$_2$, —$NR^3CON(R^6)_2$, nitro, amidino, guanidino, mercapto, sulfo, and cyano; and 3) when any alkyl group is attached to O, S, or N, and bears a hydroxyl substituent, then said hydroxyl substituent is separated by at least two carbon atoms from the O, S, or N to which the alkyl group is attached.

The second set of compounds have the generalized structural formula

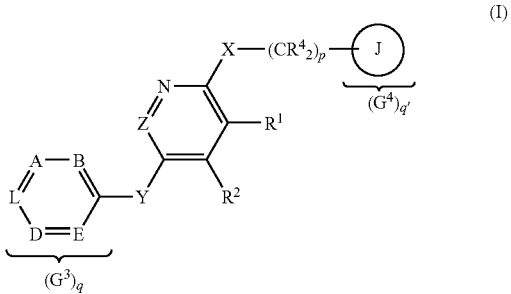

(I)

wherein
R¹ and R²:
  i) independently represent H or lower alkyl;
  ii) together form a bridge of structure

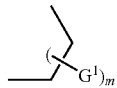

wherein binding is achieved via the terminal carbon atoms;
  iii) together form a bridge of structure

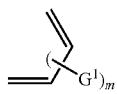

wherein binding is achieved via the terminal carbon atoms;
  iv) together form a bridge of structure

wherein one or two ring members $T^1$ are N and the others are CH or $CG^1$, and binding is achieved via the terminal atoms; or
  v) together form a bridge containing two $T^2$ moieties and one $T^3$ moiety, said bridge, taken together with the ring to which it is attached, forming a bicyclic of structure

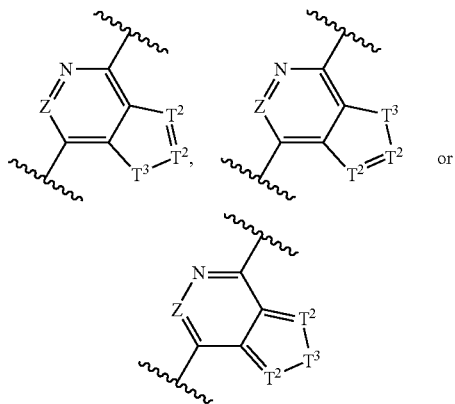

wherein
     each $T^2$ independently represents N, CH, or $CG^1$;
     $T^3$ represents S, O, $CR^4G^1$, $C(R^4)_2$, or $NR^3$.

In the above bridge substructures, the subscript m is 0 or an integer 1-4; indicating that the resultant fused rings may optionally bear up to four substituents $G^1$.

$G^1$ is a substituent independently selected from the group consisting of —$N(R^6)_2$; —$NR^3COR^6$; halogen; alkyl; cycloalkyl; lower alkenyl; lower cycloalkenyl; halogen-substituted alkyl; amino-substituted alkyl; N-lower alkylamino-substituted alkyl; N,N-di-lower alkylamino-substituted alkyl; N-lower alkanoylamino-substituted alkyl; hydroxy-substituted alkyl; cyano-substituted alkyl; carboxy-substituted alkyl; lower alkoxycarbonyl-substituted alkyl; phenyl lower alkoxycarbonyl-substituted alkyl; halogen-substituted alkylamino; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; cyano-substituted alkylamino; carboxy-substituted alkylamino; lower alkoxycarbonyl-substituted alkylamino; phenyl-lower alkoxycarbonyl-substituted alkylamino; —$OR^6$; —$SR^6$; —$S(O)R^6$; —$S(O)_2R^6$; halogenated lower alkoxy; halogenated lower alkylthio; halogenated lower alkylsulfonyl; —$OCOR^6$; —$COR^6$; —$CO_2R^6$; —$CON(R^6)_2$; —$CH_2OR^3$; —$NO_2$; —CN; amidino; guanidino; sulfo; —$B(OH)_2$; optionally substituted aryl; optionally substituted heteroaryl; optionally substituted saturated heterocyclyl; optionally substituted saturated heterocyclylalkyl; optionally substituted partially unsaturated heterocyclyl; optionally substituted partially unsaturated heterocyclylalkyl; —$OCO_2R^3$; optionally substituted heteroarylalkyl; optionally substituted heteroaryloxy; —$S(O)_p$ (optionally substituted heteroaryl); optionally substituted heteroarylalkyloxy; —$S(O)_p$ (optionally substituted heteroarylalkyl); —CHO; —$OCON(R^6)_2$; —$NR^3CO_2R^6$; and —$NR^3CON(R^6)_2$.

The group $R^3$ is H or lower alkyl. $R^6$ is independently selected from the group consisting of H; alkyl; cycloalkyl; optionally substituted aryl; optionally substituted aryl lower alkyl; lower alkyl-$N(R^3)_2$, and lower alkyl-OH.

In generalized structural formula (I), $R^4$ is H, halogen, or lower alkyl; the subscript p is 0, 1, or 2; and X is selected from the group consisting of O, S, and $NR^3$.

The linking moiety Y is selected from the group consisting of lower alkylene; —$CH_2$—O—; —$CH_2$—S—; —$CH_2$—NH—; —O—; —S—; —NH—; —O—$CH_2$—; —S(O)—; —$S(O)_2$—; —$SCH_2$—; —$S(O)CH_2$—; —$S(O)_2CH_2$—; —$CH_2S(O)$—; —$CH_2S(O)_2$—; —$(CR^4{}_2)_n$—$S(O)_p$-(5-membered heteroaryl)-$(CR^4{}_2)_s$—; and —$(CR^4{}_2)_n$—$C(G^2)(R^4)$—$(CR^4{}_2)_s$—. In the latter two linking groups Y, subscripts n and s are each independently 0 or an integer of 1-2.

$G^2$ is selected from the group consisting of —CN, —$CO_2R^3$, —$CON(R^6)_2$, and —$CH_2N(R^6)_2$.

Z represents N or $CR^4$.

Regarding the ring containing A, B, D, E, and L, the number of possible substituents $G^3$ on the ring is indicated by the subscript q, which is 1 or 2.

Substituents $G^3$ are monovalent or bivalent moieties selected from the group consisting of lower alkyl; —$NR^3COR^6$; carboxy-substituted alkyl; lower alkoxycarbonyl-substituted alkyl; —$OR^6$; —$SR^6$; —$S(O)R^6$; —$S(O)_2R^6$; —$OCOR^6$; —$COR^6$; —$CO_2R^6$; —$CH_2OR^3$; —$CON(R^6)_2$; —$S(O)_2N(R^6)_2$; —$NO_2$; —CN; optionally substituted aryl; optionally substituted heteroaryl; optionally substituted saturated heterocyclyl; optionally substituted partially unsaturated heterocyclyl; optionally substituted heteroarylalkyl; optionally substituted heteroaryloxy; —$S(O)_p$ (optionally substituted heteroaryl); optionally substituted heteroarylalkyloxy; —$S(O)_p$ (optionally substituted heteroarylalkyl); —$OCON(R^6)_2$; —$NR^3CO_2R^6$; —$NR^3CON(R^6)_2$; and bivalent bridge of structure $T^2$=$T^2$-$T^3$. In this bivalent bridge, each $T^2$ independently represents N, CH, or $CG^{3'}$; and $T^3$ represents S, O, $CR^4G^{3'}$, $C(R^4)_2$, or $NR^3$. $G^{3'}$ represents any of the above-defined moieties $G^3$ which are monovalent; and the terminal $T^2$ is bound to L, and $T^3$ is bound to D, thus forming a 5-membered fused ring.

In the ring shown at the left in generalized structural formula (I), A and D independently represent CH; B and E independently represent CH; and L is CH; with the proviso that the resulting phenyl ring bears as a $G^3$ substituent said bivalent bridge of structure $T^2=T^2-T^3$.

J is a ring selected from the group consisting of aryl; pyridyl; and cycloalkyl. The subscript q' represents the number of substituents $G^4$ on ring J and is 0, 1, 2, 3, 4, or 5.

$G^4$ is a monovalent or bivalent moiety selected from the group consisting of —$N(R^6)_2$; —$NR^3COR^6$; halogen; alkyl; cycloalkyl; lower alkenyl; lower cycloalkenyl; halogen-substituted alkyl; amino-substituted alkyl; N-lower alkylamino-substituted alkyl; N,N-di-lower alkylamino-substituted alkyl; N-lower alkanoylamino-substituted alkyl; hydroxy-substituted alkyl; cyano-substituted alkyl; carboxy-substituted alkyl; lower alkoxycarbonyl-substituted alkyl; phenyl lower alkoxycarbonyl-substituted alkyl; halogen-substituted alkylamino; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; cyano-substituted alkylamino; carboxy-substituted alkylamino; lower alkoxycarbonyl-substituted alkylamino; phenyl-lower alkoxycarbonyl-substituted alkylamino; —$OR^6$; —$SR^6$; —$S(O)R^6$; —$S(O)_2R^6$; halogenated lower alkoxy; halogenated lower alkylthio; halogenated lower alkylsulfonyl; —$OCOR^6$; —$COR^6$; —$CO_2R^6$; —$CON(R^6)_2$; —$CH_2OR^3$; —$NO_2$; —CN; amidino; guanidino; sulfo; —$B(OH)_2$; optionally substituted aryl; optionally substituted heteroaryl; optionally substituted saturated heterocyclyl; optionally substituted partially unsaturated heterocyclyl; —$OCO_2R^3$; optionally substituted heteroarylalkyl; optionally substituted heteroaryloxy; —$S(O)_p$ (optionally substituted heteroaryl); optionally substituted heteroarylalkyloxy; —$S(O)_p$ (optionally substituted heteroarylalkyl); —CHO; —$OCON(R^6)_2$; —$NR^3CO_2R^6$; —$NR^3CON(R^6)_2$; and fused ring-forming bivalent bridges attached to and connecting adjacent positions of ring J, said bridges having the structures:

a)

wherein each $T^2$ independently represents N, CH, or $CG^{4'}$; $T^3$ represents S, O, $CR^4G^{4'}$, $C(R^4)_2$, or $NR^3$; $G^{4'}$ represents any of the above-defined moieties $G^4$ which are monovalent; and binding to ring J is achieved via terminal atoms $T^2$ and $T^3$;

b)

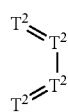

wherein each $T^2$ independently represents N, CH, or $CG^{4'}$; $G^{4'}$ represents any of the above-defined moieties $G^4$ which are monovalent; with the proviso that a maximum of two bridge atoms $T^2$ may be N; and binding to ring J is achieved via terminal atoms $T^2$; and c)

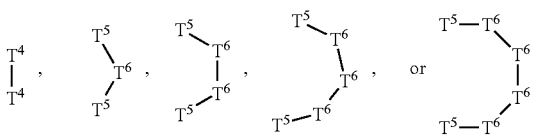

wherein each $T^4$, $T^5$, and $T^6$ independently represents O, S, $CR^4G^{4'}$, $C(R^4)_2$, or $NR^3$; $G^{4'}$ represents any of the above-identified moieties $G^4$ which are monovalent; and binding to ring J is achieved via terminal atoms $T^4$ or $T^5$; with the provisos that:

i) when one $T^4$ is O, S, or $NR^3$, the other $T^4$ is $CR^4G^{4'}$ or $C(R^4)_2$;

ii) a bridge comprising $T^5$ and $T^6$ atoms may contain a maximum of two heteroatoms O, S, or N; and iii) in a bridge comprising $T^5$ and $T^6$ atoms, when one $T^5$ group and one $T^6$ group are O atoms, or two $T^6$ groups are O atoms, said O atoms are separated by at least one carbon atom.

When $G^4$ is an alkyl group located on ring J adjacent to the linkage $CR^4_2)_p$—, and X is $NR^3$ wherein $R^3$ is an alkyl substituent, then $G^4$ and the alkyl substituent $R^3$ on X may be joined to form a bridge of structure —$(CH_2)_{p'}$— wherein p' is 2, 3, or 4, with the proviso that the sum of p and p' is 2, 3, or 4, resulting in formation of a nitrogen-containing ring of 5, 6, or 7 members.

Additional provisos are that: 1) in $G^1$, $G^2$, $G^3$, and $G^4$, when two groups $R^3$ or $R^6$ are each alkyl and located on the same N atom they may be linked by a bond, an O, an S, or $NR^3$ to form a N-containing heterocycle of 5-7 ring atoms; and 2) when an aryl, heteroaryl, or heterocyclyl ring is optionally substituted, that ring may bear up to 5 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —$CO_2R^3$, —CHO, —$CH_2OR^3$, —$OCO_2R^3$, —$CON(R^6)_2$, —$OCON(R^6)_2$, —$NR^3CONqj(R^6)_2$, nitro, amidino, guanidino, mercapto, sulfo, and cyano; and 3) when any alkyl group is attached to O, S, or N, and bears a hydroxyl substituent, then said hydroxyl substituent is separated by at least two carbon atoms from the O, S, or N to which the alkyl group is attached.

The third set of compounds have the generalized structural formula

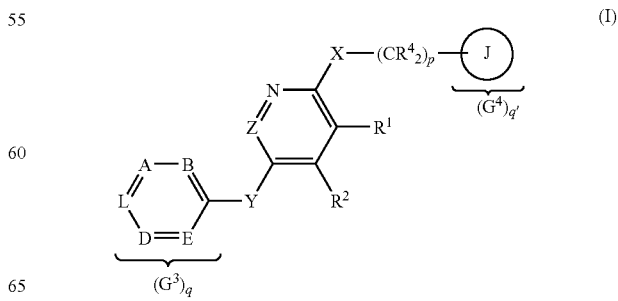

(I)

wherein
R$^1$ and R$^2$:
  i) independently represent H or lower alkyl;
  ii) together form a bridge of structure

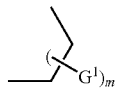

wherein binding is achieved via the terminal carbon atoms;
  iii) together form a bridge of structure

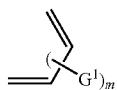

wherein binding is achieved via the terminal carbon atoms;
  iv) together form a bridge of structure

wherein one or two ring members T$^1$ are N and the others are CH or CG$^1$, and binding is achieved via the terminal atoms; or
  v) together form a bridge containing two T$^2$ moieties and one T$^3$ moiety, said bridge, taken together with the ring to which it is attached, forming a bicyclic of structure

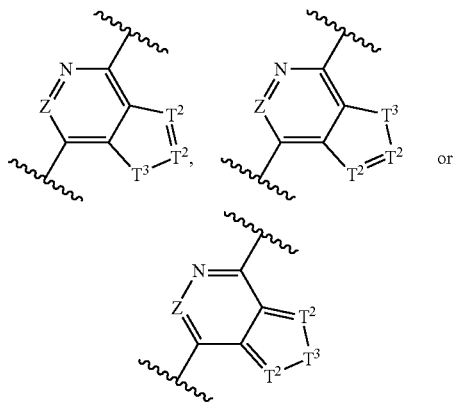

wherein
    each T$^2$ independently represents N, CH, or CG$^1$;
    T$^3$ represents S, O, CR$^4$G$^1$, C(R$^4$)$_2$, or NR$^3$.

In the above bridge structures, the subscript m is 0 or an integer 1-4; indicating that the resultant fused rings may optionally bear up to four substituents G$^1$.

G$^1$ is a substituent independently selected from the group consisting of —N(R$^6$)$_2$—NR$^3$COR$^6$; halogen; alkyl; cycloalkyl; lower alkenyl; lower cycloalkenyl; halogen-substituted alkyl; amino-substituted alkyl; N-lower alkylamino-substituted alkyl; N,N-di-lower alkylamino-substituted alkyl; N-lower alkanoylamino-substituted alkyl; hydroxy-substituted alkyl; cyano-substituted alkyl; carboxy-substituted alkyl; lower alkoxycarbonyl-substituted alkyl; phenyl lower alkoxycarbonyl-substituted alkyl; halogen-substituted alkylamino; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; cyano-substituted alkylamino; carboxy-substituted alkylamino; lower alkoxycarbonyl-substituted alkylamino; phenyl-lower alkoxycarbonyl-substituted alkylamino; —OR$^6$; —SR$^6$; —S(O)R$^6$; —S(O)$_2$R$^6$; halogenated lower alkoxy; halogenated lower alkylthio; halogenated lower alkylsulfonyl; —OCOR$^6$; —COR$^6$; —CO$_2$R$^6$; —CON(R$^6$)$_2$; —CH$_2$OR$^3$; —NO$_2$; —CN; amidino; guanidino; sulfo; —B(OH)2; optionally substituted aryl; optionally substituted heteroaryl; optionally substituted saturated heterocyclyl; optionally substituted saturated heterocyclylalkyl; optionally substituted partially unsaturated heterocyclyl; optionally substituted partially unsaturated heterocyclylalkyl; —OCO$_2$R$^3$; optionally substituted heteroarylalkyl; optionally substituted heteroaryloxy; —S(O)$_p$ (optionally substituted heteroaryl); optionally substituted heteroarylalkyloxy; —S(O)$_p$ (optionally substituted heteroarylalkyl); —CHO; —OCON(R$^6$)$_2$; —NR$^3$CO$_2$R$^6$; and —NR$^3$CON(R$^6$)$_2$.

The group R$^3$ is H or lower alkyl. R$^6$ is independently selected from the group consisting of H; alkyl; cycloalkyl; optionally substituted aryl; optionally substituted aryl lower alkyl; lower alkyl-N(R$^3$)$_2$, and lower alkyl-OH.

In generalized structural formula (I), R$^4$ is H, halogen, or lower alkyl; the subscript p is 0, 1, or 2; and X is selected from the group consisting of O, S, and NR$^3$.

The linking moiety Y is selected from the group consisting of lower alkylene; —CH$_2$—O—; —CH$_2$—S—; —CH$_2$—NH—; —O—; —S—; —NH—; —O—CH$_2$—; —S(O)—; —S(O)$_2$—; —SCH$_2$—; —S(O)CH$_2$—; —S(O)$_2$CH$_2$—; —CH$_2$S(O)—; —CH$_2$S(O)$_2$—; —(CR$^4$$_2$)$_n$—S(O)$_p$-(5-membered heteroaryl)-(CR$^4$$_2$)$_s$—; and —(CR$^4$$_2$)$_n$—C(G$^2$)(R$^4$)—(CR$^4$$_2$)$_s$—. In the latter two linking groups Y, subscripts n and s are each independently 0 or an integer of 1-2. G$^2$ is selected from the group consisting of —CN, —CO$_2$R$^3$, —CON(R$^6$)$_2$, and —CH$_2$N(R$^6$)$_2$.

Z represents CR$^4$.

Regarding the ring containing A, B, D, E, and L, the number of possible substituents G$^3$ on the ring is indicated by the subscript q, which is 1 or 2.

Substituents G$^3$ are monovalent or bivalent moieties selected from the group consisting of —NR$^3$COR$^6$; carboxy-substituted alkyl; lower alkoxycarbonyl-substituted alkyl; —OR$^6$; —SR$^6$; —S(O)R$^6$; —S(O)$_2$R$^6$; —OCOR$^6$; —COR$^6$; —CO$_2$R$^6$; —CH$_2$OR$^3$; —CON(R$^6$)$_2$; —S(O)$_2$N(R$^6$)$_2$; —NO$_2$; —CN; optionally substituted aryl; optionally substituted heteroaryl; optionally substituted saturated heterocyclyl; optionally substituted partially unsaturated heterocyclyl; optionally substituted heteroarylalkyl; optionally substituted heteroaryloxy; S(O)$_p$ (optionally substituted heteroaryl); optionally substituted heteroarylalkyloxy; —S(O)$_p$ (optionally substituted heteroarylalkyl); —OCON(R$^6$)$_2$; —NR$^3$CO$_2$R$^6$; —NR$^3$CON(R$^6$)$_2$; and bivalent bridge of structure T$^2$=T$^2$-T$^1$. In this bivalent bridge, each T$^2$ independently represents N, CH, or CG$^{3'}$; and T$^3$ represents S, O, CR$^4$G$^{3'}$, C(R$^4$)$_2$, or NR$^3$. G$^{3'}$ represents any of the above-defined moieties G$^3$ which are monovalent; and the terminal T$^2$ is bound to L, and T$^3$ is bound to D, thus forming a 5-membered fused ring.

In the ring shown at the left in generalized structural formula (I), A and D independently represent N or CH; B and E independently represent N or CH; and L represents N or CH; with the provisos that a) the total number of N atoms in the ring containing A, B, D, E, and L is 0, 1, 2, or 3; and b) when L represents CH and any $G^3$ is a monovalent substituent, at least one of A and D is an N atom; and c) when L represents CH and a $G^3$ is a bivalent bridge of structure $T^2=T^2-T^3$, then A, B, D, and E are also CH.

J is a ring selected from the group consisting of aryl; pyridyl; and cycloalkyl. The subscript q' represents the number of substituents $G^4$ on ring J and is 0, 1, 2, 3, 4, or 5.

$G^4$ is a monovalent or bivalent moiety selected from the group consisting of —$N(R^6)_2$; —$NR^3COR^6$; halogen; alkyl; cycloalkyl; lower alkenyl; lower cycloalkenyl; halogen-substituted alkyl; amino-substituted alkyl; N-lower alkylamino-substituted alkyl; N,N-di-lower alkylamino-substituted alkyl; N-lower alkanoylamino-substituted alkyl; hydroxy-substituted alkyl; cyano-substituted alkyl; carboxy-substituted alkyl; lower alkoxycarbonyl-substituted alkyl; phenyl lower alkoxycarbonyl-substituted alkyl; halogen-substituted alkylamino; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; cyano-substituted alkylamino; carboxy-substituted alkylamino; lower alkoxycarbonyl-substituted alkylamino; phenyl-lower alkoxycarbonyl-substituted alkylamino; —$OR^6$; —$SR^6$; —$S(O)R^6$; —$S(O)_2R^6$; halogenated lower alkoxy; halogenated lower alkylthio; halogenated lower alkylsulfonyl; —$OCOR^6$; —$COR^6$; —$CO_2R^6$; —$CON(R^6)_2$; —$CH_2OR^3$; —$NO_2$; —CN; amidino; guanidino; sulfo; —$B(OH)2$; optionally substituted aryl; optionally substituted heteroaryl; optionally substituted saturated heterocyclyl; optionally substituted partially unsaturated heterocyclyl; —$OCO_2R^3$; optionally substituted heteroarylalkyl; optionally substituted heteroaryloxy; —$S(O)_p$ (optionally substituted heteroaryl); optionally substituted heteroarylalkyloxy; —$S(O)_p$ (optionally substituted heteroarylalkyl); —CHO; —$OCON(R^6)_2$; —$NR^3CO_2R^6$; —$NR^3CON(R^6)_2$; and fused ring-forming bivalent bridges attached to and connecting adjacent positions of ring J, said bridges having the structures:

a)

wherein each $T^2$ independently represents N, CH, or $CG^{4'}$; $T^3$ represents S, O, $CR^4G^{4'}$, $C(R^4)_2$, or $NR^3$; G4' represents any of the above-defined moieties G4 which are monovalent; and binding to ring J is achieved via terminal atoms $T^2$ and $T^3$;

b)

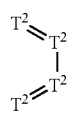

wherein each $T^2$ independently represents N, CH, or $CG^{4'}$; G4' represents any of the above-defined moieties G4 which are monovalent; with the proviso that a maximum of two bridge atoms $T^2$ may be N; and binding to ring J is achieved via terminal atoms $T^2$; and c)

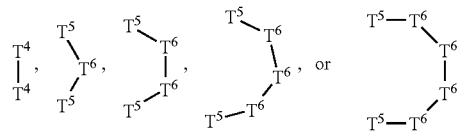

wherein each $T^4$, $T^5$, and $T^6$ independently represents O, S, $CR^4G^{4'}$, $C(R^4)_2$, or $NR^3$; G4' represents any of the above-defined moieties G4 which are monovalent; and binding to ring J is achieved via terminal atoms $T^4$ or $T^5$ with the provisos that:
  i) when one $T^4$ is O, S, or $NR^3$, the other $T^4$ is $CR^4G^{4'}$ or $C(R^4)_2$;
  ii) a bridge comprising $T^5$ and $T^6$ atoms may contain a maximum of two heteroatoms O, S, or N; and
  iii) in a bridge comprising $T^5$ and $T^6$ atoms, when one $T^5$ group and one $T^6$ group are O atoms, or two $T^6$ groups are O atoms, said O atoms are separated by at least one carbon atom;

When $G^4$ is an alkyl group located on ring J adjacent to the linkage $CR^4{}_2)_p$—, and X is $NR^3$ wherein $R^3$ is an alkyl substituent, then $G^4$ and the alkyl substituent $R^3$ on X may be joined to form a bridge of structure —$(CH_2)_{p'}$— wherein p' is 2, 3, or 4, with the proviso that the sum of p and p' is 2, 3, or 4, resulting in formation of a nitrogen-containing ring of 5, 6, or 7 members.

Additional provisos are that: 1) in $G^1$, G2, $G^3$, and $G^4$, when two groups $R^3$ or $R^6$ are each alkyl and located on the same N atom they may be linked by a bond, an O, an S, or $NR^3$ to form a N-containing heterocycle of 5-7 ring atoms; and 2) when an aryl, heteroaryl, or heterocyclyl ring is optionally substituted, that ring may bear up to 5 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —$CO_2R^3$, —CHO, —$CH_2OR^3$, —$OCO_2R^3$, —$CON(R^6)_2$, —$OCON(R^3)_2$, —$NR^3CON(R^6)_2$, nitro, amidino, guanidino, mercapto, sulfo, and cyano; and 3) when any alkyl group is attached to O, S, or N, and bears a hydroxyl substituent, then said hydroxyl substituent is separated by at least two carbon atoms from the O, S, or N to which the alkyl group is attached.

Pharmaceutically acceptable salts of these compounds as well as commonly used prodrugs of these compounds such as O-acyl derivatives of invention compounds which contain hydroxy groups are also within the scope of the invention.

The invention also relates to pharmaceutical compositions comprising one or more of the compounds of the invention, or their salts or prodrugs, in a pharmaceutically acceptable carrier.

The invention also relates to a method for using these materials to treat a mammal having a condition characterized by abnormal angiogenesis or hyperpermiability processes, comprising administering to the mammal an amount of a compound of the invention, or a salt or prodrug thereof, which is effective to treat the condition.

DETAILED DESCRIPTION

Definitions:

The prefix "lower" denotes a radical having up to and including a maximum of 7 atoms, especially up to and including a maximum of 5 carbon atoms, the radicals in question being either linear or branched with single or multiple branching.

"Alkyl" means a hydrocarbon radical having up to a maximum of 12 carbon atoms, which may be linear or branched with single or multiple branching. Alkyl is especially lower alkyl.

Where the plural form is used for compounds, salts, and the like, this is taken to mean also a single compound, salt, or the like.

Any asymmetric carbon atoms may be present in the (R)-, (S)- or (R,S)configuration, preferably in the (R)- or (S)-configuration. Substituents at a double bond or a ring may be present in cis- (=Z-) or trans (=E-) form. The compounds may thus be present as mixtures of isomers or as pure isomers, preferably as enantiomer-pure diastereomers and having pure cis- or trans-double bonds.

Lower alkylene Y may be branched or linear but is preferably linear, especially methylene ($—CH_2—$), ethylene ($—CH_2—CH_2—$), trimethylene ($—CH_2—CH_2—CH_2—$) or tetramethylene ($—CH_2CH_2CH_2CH_2—$). When Y is lower alkylene, it is most preferably methylene.

"Aryl" means an aromatic radical having 6 to 14 carbon atoms, such as phenyl, naphthyl, fluorenyl or phenanthrenyl.

"Halogen" means fluorine, chlorine, bromine, or iodine but is especially fluorine, chlorine, or bromine.

"Pyridyl" means 1-, 2-, or 3-pyridyl but is especially 2- or 3-pyridyl.

"Cycloalkyl" is a saturated carbocycle that contains between 3 and 12 carbons but preferably 3 to 8 carbons.

"Cycloalkenyl" means a non-reactive and non-aromatic unsaturated carbocycle that contains between 3 and 12 carbons but preferably 3 to 8 carbons and up to three double bonds. It is well known to those skilled in the art that cycloalkenyl groups that differ from aromatics by lacking only one double bond such as cyclohaxadiene are not sufficiently non-reactive to be reasonable drug substances and therefor their use as substituents is not within the scope of this invention.

Cycloalkyl and cycloalkenyl groups may contain branch points such that they are substituted by alkyl or alkenyl groups. Examples of such branched cyclic groups are 3,4-dimethylcyclopentyl, 4-allylcyclohexyl or 3-ethylcyclopent-3-enyl.

Salts are especially the pharmaceutically acceptable salts of compounds of formula I such as, for example, acid addition salts, preferably with organic or inorganic acids, from compounds of formula I with a basic nitrogen atom. Suitable inorganic acids are, for example, halogen acids such as hydrochloric acid, sulfuric acid, or phosphoric acid. Suitable organic acids are, for example, carboxylic, phosphonic, sulfonic, or sulfamic acids, for example acetic acid, propionic acid, octanoic acid, decanoic acid, dodecanoic acid, glycolic acid, lactic acid, -hydroxybutyric acid, gluconic acid, glucosemonocarboxylic acid, fumaric acid, succinic acid, adipic acid, pimelic acid, suberic acid, azeiaic acid, malic acid, tartaric acid, citric acid, glucaric acid, galactaric acid, amino acids, such as glutamic acid, aspartic acid, N-methylglycine, acetytaminoacetic acid, N-acetylasparagine or N-acetylcysteine, pyruvic acid, acetoacetic acid, phosphoserine, 2- or 3-glycerophosphoric acid.

In the definition of Y, the diradical "-(5 member heteroaryl)-" denotes a 5-membered aromatic heterocycle containing 1-3 heteroatoms selected from O, S, and N, the number of N atoms being 0-3 and the number of O and S atoms each being 0-1 and connected to the sulfur from a carbon and to $—(CR^4{}_2)_s—$ through a C or N atom. Examples of such diradicals include

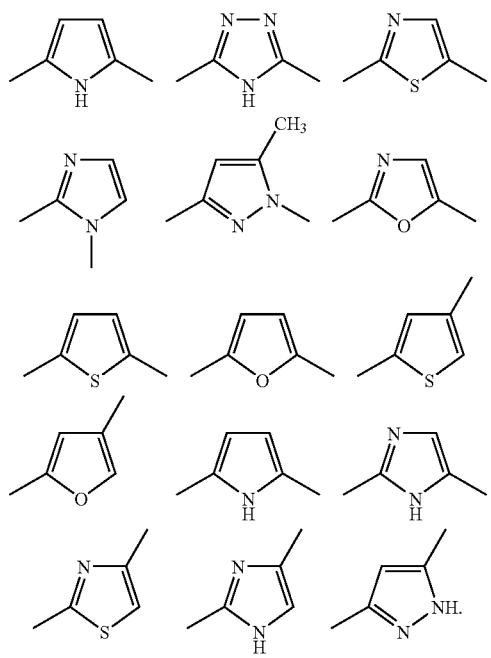

In the definitions of $G^1$, $G^2$, $G^3$, and $G^4$ the statement is made that when two groups $R^3$ or $R^6$ are found on a single N, they can be combined into a heterocycle of 5-7 atoms. Examples of such heterocycles, including the N to which they are attached, are:

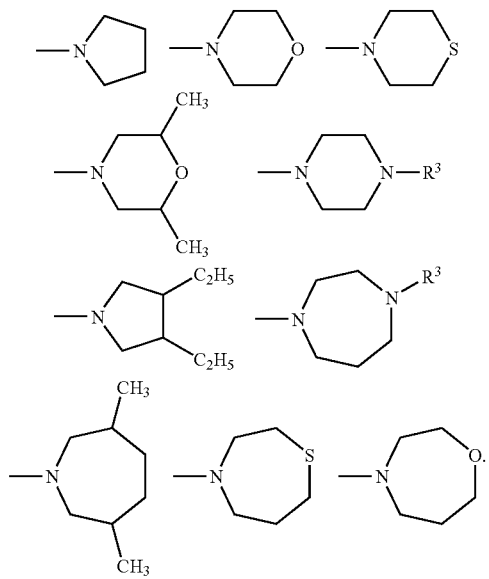

"Heterocyclyl" or "heterocycle" means a five- to seven-membered heterocyclic system with 1-3 heteroatoms selected from the group nitrogen, oxygen, and sulfur, which may be unsaturated or wholly or partly saturated, and is unsubstituted or substituted especially by lower alkyl, such as methyl, ethyl, 1-propyl, 2-propyl, or tert-butyl.

When an aryl, heteroaryl, or heterocyclyl ring is said to be optionally substituted, that ring may bear up to 5 substituents which are independently selected from the group consisting of amino, mono- or di-loweralkyl-substituted amino, lower alkanoylamino, halogeno, lower alkyl, halogenated lower alkyl such as trifluoromethyl, hydroxy, lower alkoxy, lower alkylthio, halogenated lower alkoxy such as trifluoromethoxy, halogenated lower alkylthio such as trifluoromethylthio, lower alkanoyloxy, —CO$_2$R$^3$, —CHO, —CH$_2$OR$^3$, —OCO$_2$R$^3$, —CON(R$^6$)$_2$, —OCON(R$^6$)$_2$, —NR$^3$CON(R$^6$)$_2$, nitro, amidino, guanidino, mercapto, sulfo, and cyano.

In the ring attached to Y, the ring members A, B, D, E, and L may be N or CH, it being understood that the optional substituents G$^3$ are necessarily attached to carbon and not nitrogen, and that when a given carbon bears a substituent group G$^3$, that G$^3$ group is in place of the H atom the carbon would bear in the absence of the G$^3$ group.

Examples of ring J together with two adjacent G$^4$ moieties which taken together form a second fused ring are:

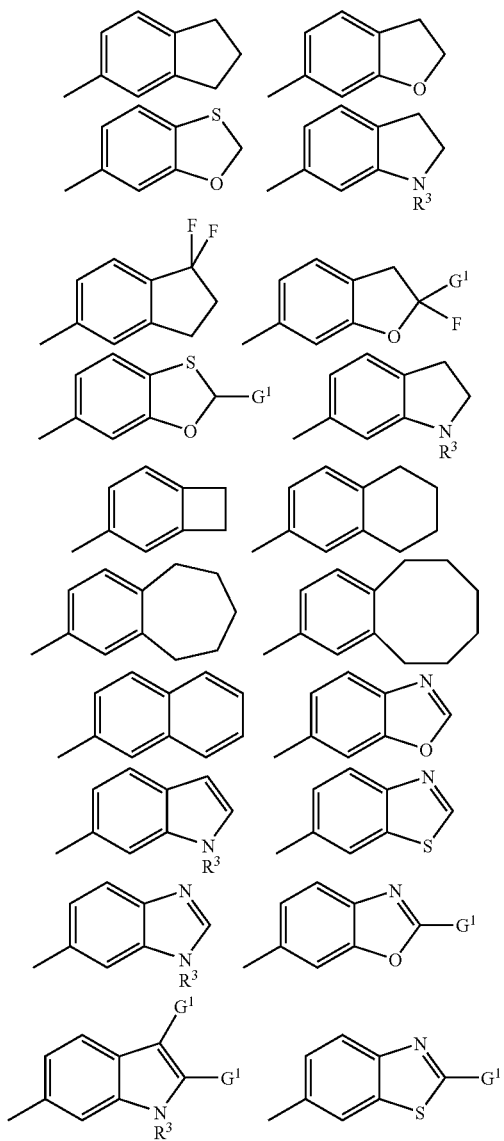

"Heteroaryl" means a monocyclic or fused bicyclic aromatic system with between 5 and 10 atoms in total of which 1-4 are heteroatoms selected from the group comprising nitrogen, oxygen, and sulfur and with the remainder being carbon. Heteroaryl is preferably a monocyclic system with 5 or 6 atoms in total, of which 1-3 are heteroatoms.

"Alkenyl" means an unsaturated radical having up to a maximum of 12 carbon atoms and may be linear or branched with single or multiple branching and containing up to 3 double bonds. Alkenyl is especially lower alkenyl with up to 2 double bonds.

"Alkanoyl" means alkylcarbonyl, and is especially lower alkylcarbonyl.

Halogenated lower alkyl, halogenated lower alkoxy and halogenated lower alkylthio are substituents in which the alkyl moieties are substituted either partially or in full with halogens, preferably with chlorine and/or fluorine and most preferably with fluorine. Examples of such substituents are trifluoromethyl, trifluoromethoxy, trifluoromethylthio, 1,1,2,2-tetrafluoroethoxy, dichloromethyl, fluoromethyl and difluoromethyl.

When a substituent is named as a string of fragments such as "phenyl-lower alkoxycarbonyl-substituted alkylamino," it is understood that the point of attachment is to the final moiety of that string (in this case amino) and that the other fragments of that string are connected to each other in sequence as they are listed in the string. Thus an example of "phenyl-lower alkoxycarbonyl-substituted alkylamino" is:

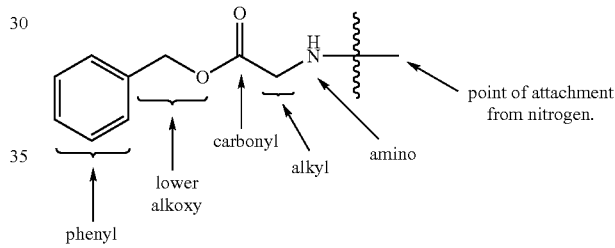

When a substituent is named as a string of fragments with a bond at the start (typically written as a dash) such as "—S(O)$_p$ (optionally substituted heteroarylalkyl)", it is understood that the point of attachment is to the first atom of that string (in this case S or sulfur) and that the other fragments of that string are connected to each other in sequence as they are listed in the string. Thus an example of "—S(O)$_p$ (optionally substituted heteroarylalkyl)" is:

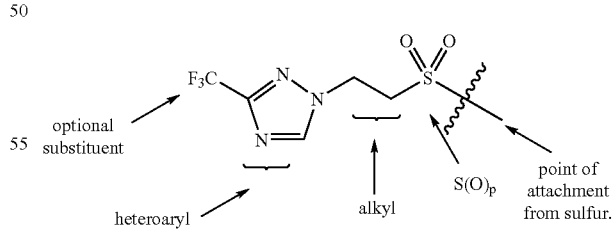

It is to be understood that the left-most moiety of each of the variants of the linker Y is connected to the ring containing A, B, D, E, and L and that the right-most moiety of the linker is connected to the pyridazine fragment of the generalized formulae. Thus, examples of the use of the linker "—CH$_2$—O—" or of the linker "—O—CH$_2$—" are represented in the following invention compounds:

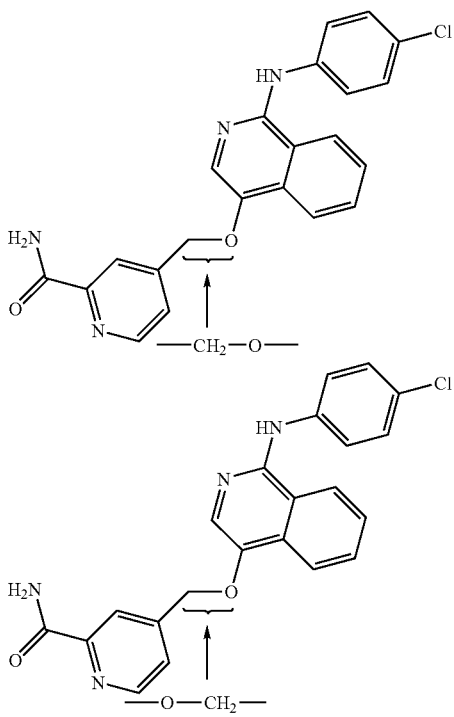

In generalized structural formula (I), the preferred and most preferred groups are as follows.

$R^1$ and $R^2$ preferably:

i) together form a bridge of structure

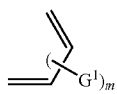

wherein binding is achieved via the terminal carbon atoms; or ii) together form a bridge of structure

wherein one of the ring members $T^1$ is N and the others are CH, and binding is achieved via the terminal atoms; or iii) together form a bridge containing two $T^2$ moieties and one $T^3$ moiety, said bridge, taken together with the ring to which it is attached, forming a bicyclic of structure

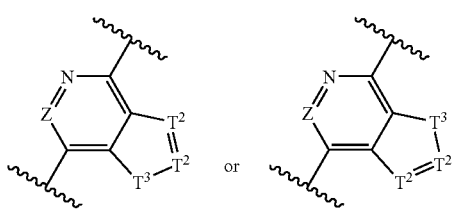

wherein
each $T^2$ independently represents N, CH, or $CG^1$;
$T^3$ represents S, O, $CH_2$, or $NR^3$; and
with the proviso that when $T^3$ is O or S, at least one $T^2$ is CH or $CG^1$.

Most preferably, any group $G^1$ is located on a non-terminal atom of the bridge. Most preferably, in the bridge in iii), the terminal $T^2$ is N or CH, the non-terminal $T^2$ is CH or $CG^1$, and $T^3$ is S or O.

The subscript m is preferably 0 or an integer 1-2, and substituents $G^1$ are preferably selected from the group consisting of —$N(R^6)_2$; —$NR^3COR^6$; halogen; lower alkyl; hydroxy-substituted alkyl; amino-substituted alkylamino; N-lower alkylamino-substituted alkylamino; N,N-di-lower alkylamino-substituted alkylamino; hydroxy-substituted alkylamino; carboxy-substituted alkylamino; lower alkoxycarbonyl-substituted alkylamino; —$OR^6$; —$SR^1$; —$S(O)R^6$; —$S(O)_2R^6$; halogenated lower alkoxy; halogenated lower alkylthio; halogenated lower alkylsulfonyl; —$OCOR^6$; —$COR^6$; —$CO_2R^6$; —$CON(R^6)_2$; —$NO_2$; —CN; optionally substituted heteroarylalkyl; optionally substituted heteroaryloxy; optionally substituted heteroarylalkyloxy; and —$S(O)_p$ (optionally substituted heteroarylalkyl). Most preferably, m is 0, and $G^1$ is a substituent independently selected from the group consisting of —$N(R^6)_2$; —$NR^3COR^6$; halogen; —$OR^6$ wherein $R^6$ represents lower alkyl; —$NO_2$; optionally substituted heteroaryloxy; and optionally substituted heteroarylalkyloxy.

When $R^6$ is an alkyl group, it is preferably lower alkyl. The group $R^4$ is preferably H; p is preferably 0 or 1; and X is preferably $NR^3$.

In the linker group Y, the subscripts n and s are preferably 0 or 1, most preferably 0. Preferably, Y is selected from the group consisting of lower alkylene, —$CH_2$—O—; —$CH_2$—S—; —$CH_2$—NH—; —S—; —NH—; —$(CR^4_2)_n$—$S(O)_p$-(5-membered heteroaryl)-$(CR^4_2)_s$—; —$(CR^4_2)_n$—$C(G^2)$ $(R^4)$—$(CR^4_2)_s$—; and —O—$CH_2$—. Most preferably, Y is selected from the group consisting of —$CH_2$—O—; —$CH_2$—NH—; —S—; —NH—; —$(CR^4_2)_n$—$S(O)_p$-(5-membered heteroaryl)-$(CR^4_2)_s$—; and —O—$CH_2$—.

In the ring at the left side of the structure (I), A, D, B, and E are preferably CH, and L is N or CH, with the proviso that when L is N, any substituents $G^3$ are preferably monovalent, and when L is CH then any substituents $G^3$ are preferably divalent.

The substituents $G^3$ are preferably selected from the group consisting of monovalent moieties lower alkyl; —$NR^3COR^6$; —$OR^6$; —$SR^6$; —$S(O)R^6$; —$S(O)_2R^6$; —$CO_2R^6$; —CON$(R^6)_2$; —$S(O)_2N(R^6)_2$; —CN; optionally substituted aryl; optionally substituted heteroaryl; optionally substituted heteroarylalkyl; optionally substituted heteroaryloxy; —$S(O)_p$ (optionally substituted heteroaryl); optionally substituted heteroarylalkyloxy; —$S(O)_p$ (optionally substituted heteroarylalkyl); and bivalent bridge of structure $T^2$=$T^2$-$T^3$ wherein T2 represents N or CH. $T^3$ is preferably S, O, $CR^4_2$, or $NR^3$.

Most preferably, $G^3$ is selected from the group consisting of monovalent moieties lower alkyl; —$NR^3COR^6$; —$CO_2R^6$; —CON$(R^6)_2$; —$S(O)_2N(R^6)_2$; and bivalent bridge of structure $T^2$=$T^2$-$T^3$ wherein $T^2$ represents N or CH. Most preferably $T^3$ is S, O, $CH_2$, or $NR^3$.

Most preferably, the subscript q, which represents the number of substituents $G^3$, is 1.

Ring J is preferably a phenyl ring, and subscript q' representing the number of substituents $G^4$ on the phenyl ring, is preferably 0, 1, 2, or 3. Subscript q' is most preferably 1, or 2.

$G^4$ moieties are preferably selected from the group consisting of —$N(R^6)_2$—$NR^3COR^6$; halogen; alkyl; halogen-substituted alkyl; hydroxy-substituted alkyl; carboxy-substituted alkyl; lower alkoxycarbonyl-substituted alkyl; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; carboxy-substituted alkylamino; lower alkoxycarbonyl-substituted alkylamino; phenyl-lower alkoxycarbonyl-substituted alkylamino; —OR$^6$; —SR$^6$; —S(O)R$^6$; —S(O)$_2$R$^6$; halogenated lower alkoxy; halogenated lower alkylthio; halogenated lower alkylsulfonyl; —OCOR$^6$; —COR$^6$; —CO$_2$R$^6$; —CON(R$^6$)$_2$; —CH$_2$OR$^3$; —NO$_2$; —CN; optionally substituted heteroarylalkyl; optionally substituted heteroaryloxy; —S(O)$_p$ (optionally substituted heteroaryl); optionally substituted heteroarylalkyloxy; —S(O)$_p$ (optionally substituted heteroarylalkyl); as well as fused ring-forming bridges attached to and connecting adjacent positions of the phenyl ring, said bridges having the structures:

a)

wherein each T$^2$ independently represents N, or CH; T$^3$ represents S, or O; and
binding to the phenyl ring is achieved via terminal atoms T$^2$ and T$^3$;

b)

wherein each T$^2$ independently represents N, CH, or CG$^4$; with the proviso that a maximum of two bridge atoms T$^2$ may be N; and binding to the phenyl ring is achieved via terminal atoms T$^2$; and c)

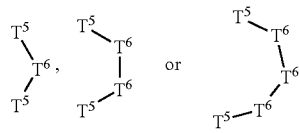

wherein each T$^5$, and T$^6$ independently represents O, S, or CH$_2$; and
binding to ring J is achieved via terminal atoms T$^5$;
with the provisos that:
i) a bridge comprising T$^5$ and T$^6$ atoms may contain a maximum of two heteroatoms O, S, or N; and
ii) in a bridge comprising T$^5$ and T$^6$ atoms, when one T$^5$ group and one T$^6$ group are O atoms, or two T$^6$ groups are O atoms, said O atoms are separated by at least one carbon atom.

Alkyl groups which constitute all or part of a G$^4$ moiety are preferably lower alkyl.

When G$^4$ is an alkyl group located on ring J adjacent to the linkage CR$^4{}_2$)$_p$—, and X is NR$^3$ wherein R$^3$ is an alkyl substituent, then G$^4$ and the alkyl substituent R$^3$ on X may be joined to form a bridge of structure —(CH$_2$)$_{p'}$— wherein p' is preferably 2 or 3, with the proviso that the sum of p and p' is 2 or 3, resulting in formation of a nitrogen-containing ring of 5 or 6 members. Most preferably, the sum of p and p' is 2, resulting in formation of a 5-membered ring.

Most preferably, in G$^1$, G$^2$, G$^3$, and G$^4$, when two groups R$^6$ are each alkyl and located on the same N atom they may be linked by a bond, an O, an S, or NR$^3$ to form a N-containing heterocycle of 5-6 ring atoms.

Preferably, when an aryl, heteroaryl, or heterocyclyl ring is optionally substituted, that ring may bear up to 2 substituents which are independently selected from the group consisting of amino, mono-loweralkyl-substituted amino, di-lower-alkyl-substituted amino, lower alkanoylamino, halogeno, lower alkyl, halogenated lower alkyl, hydroxy, lower alkoxy, lower alkylthio, halogenated lower alkoxy, halogenated lower alkylthio, —CH$_2$OR$^3$, nitro, and cyano.

The method of the invention is intended to be employed for treatment of VEGF-mediated conditions in both humans and other mammals.

The compounds may be administered orally, dermally, parenterally, by injection, by inhalation or spray, or sublingually, rectally or vaginally in dosage unit formulations. The term 'administered by injection' includes intravenous, intraarticular, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired, other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations.

Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administered transdermally using methods known to those skilled in the art (see, for example: Chien; "Transdermal Controlled Systemic Medications"; Marcel Dekker, Inc.; 1987. Lipp et al. WO 94/04157 Mar. 3, 1994). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures one or more materials selected from lower alcohols, lower ketones, lower carboxylic acid esters, polar ethers, lower hydrocarbons, halogenated hydrocarbons.

Suitable penetration enhancing materials for transdermal delivery systems are known to those skilled in the art, and include, for example, monohydroxy or polyhydroxy alcohols such as ethanol, propylene glycol or benzyl alcohol, saturated or unsaturated $C_8$-$C_{18}$ fatty alcohols such as lauryl alcohol or cetyl alcohol, saturated or unsaturated $C_8$-$C_{18}$ fatty acids such as stearic acid, saturated or unsaturated fatty esters with up to 24 carbons such as methyl, ethyl, propyl, isopropyl, n-butyl, sec-butyl isobutyl tert-butyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures one or more materials selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated fatty esters with up to 24 carbons, diesters of saturated or unsaturated dicarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrene-butadiene copolymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.1 to 200 mg administered between one to four times daily. The transdermal concentration will preferably be that required to maintain a daily dose of from 0.01 to 200 mg/Kg. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, but not limited to the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests.

General Preparative Methods

The compounds of the invention may be prepared by use of known chemical reactions and procedures. Nevertheless, the following general preparative methods are presented to aid the reader in synthesizing the KDR inhibitors, with more detailed particular examples being presented below in the experimental section describing the working examples.

All variable groups of these methods are as described in the generic description if they are not specifically defined below. When a variable group or substituent with a given symbol (i.e. $R^3$, $R^4$, $R^6$, $G^1$, $G^2$, $G^3$, or $G^4$) is used more than once in a given structure, it is to be understood that each of these groups or substituents may be independently varied within the range of definitions for that symbol. As defined above, the compounds of the invention contain ring units each of which may independently bear between 0 and 5 substituents $G^1$, $G^3$, or $G^4$, which are not defined as H. By contrast, it is to be noted that in the general method schemes below, the $G^1$, $G^3$, or $G^4$ substituents are used as if their definition includes H, to show where such $G^1$, $G^3$, or $G^4$ substituents may exist in the structures, and for ease in drawing. No change in the definition of $G^1$, $G^3$, or $G^4$ is intended by this non-standard usage, however. Thus, only for purposes of the general method schemes below, $G^1$, $G^3$, or $G^4$ may be H in addition to the moieties set forth in the definitions of $G^1$, $G^3$, or $G^4$. The ultimate compounds contain 0 to 5 non-hydrogen groups $G^1$, $G^3$ or $G^4$.

Within these general methods the variable M is equivalent to the moiety

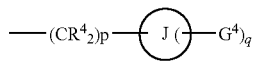

in which each variable group or substituent is allowed to independently vary within the limits defined earlier for that symbol.

Within these general methods the variable $Q^1$ is equivalent to the moiety

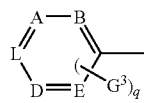

in which L is N and each other variable group or substituent is allowed to independently vary within the limits defined earlier for that symbol.

Within these general methods the variable $Q^2$ is equivalent to the moiety

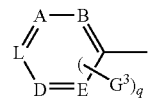

in which each variable group or substituent is allowed to independently vary within the limits defined earlier for that symbol.

It is recognized that compounds of the invention with each claimed optional functional group cannot be prepared with each of the below-listed methods. Within the scope of each method optional substituents are used which are stable to the reaction conditions, or the functional groups which may participate in the reactions are present in protected form where necessary, and the removal of such protective groups is completed at appropriate stages by methods well known to those skilled in the art.

General Method A—The compounds of formula I-A in which X, M, and $Q^2$ are defined as above, Y is —CH$_2$—O—, —CH$_2$—S—, —CH$_2$—NH—, —O—, —S—, or —NH—, and $R^1$ and $R^2$ together with the carbons to which they are attached form a fused 5-membered ring aromatic heterocycle, hal is halogen (Cl, Br, F, or I but preferably Cl, Br or F) are conveniently prepared according to a reaction sequence as shown in Method A. Thus, a heterocycle of formula II in which R is lower alkyl can be made by one skilled in the art according to the corresponding published procedures in the reference table. In the cases of thiophene-2,3-dicarboxylic acid (table entry 1) and pyrazole-3,4-dicarboxylic acid (table entry 10), the carboxylic acids are converted to methyl or ethyl esters by treatment with the corresponding alcohol and catalytic mineral acid (typically sulfuric acid) at reflux. The diester of formula II is treated with hydrazine hydrate to furnish intermediate III (for specific reaction conditions see Robba, M.; Le Guen, Y. *Bull. Soc. Chem. Fr.* 1970 12 4317). Compound III is treated with a halogenating agent such as phosphorous oxychloride, phosphorous oxybromide, phosphorous pentabromide, or phosphorous pentachloride to yield dihalo intermediate IV. The dichloro or dibromo intermediates can be converted to the difluoro intermediate (when desired) by reaction with hydrogen fluoride. By using iodo reagents such as potassium iodide or tetrabutylammonium iodide in subsequent steps, the iodo intermediate is formed in the reaction mixtures without being isolated as a pure substance. Dihalo intermediate IV is treated with a nucleophile of formula V in refluxing alcohol or other suitable solvent such as tetrahydrofuran (THF), dimethoxyethane (DME), dimethylformamide (DMF), dimethylsulfoxide (DMSO), or the like to furnish the intermediate of formula VI. Such condensations can also be done in a melt free of solvent and can be catalyzed by acids such as HCl or bases such as triethylamine or 1,8-diazobicyclo[5.4.0]undec-7-ene (DBU). The compound of formula VI is reacted with compounds of formula VII in a suitable aprotic solvent such as DMSO, DMF or solvent free often with a basic catalyst such as DBU or CsCO$_4$, or a crown ether such as 18-crown-6 at temperatures usually between room temperature and reflux to furnish invention compound of formula I-A. It is understood that the nature of the starting materials will dictate the choice of suitable solvents, catalyst (if used) and temperature by one skilled in the art. Intermediates of formula V and VII are often commercial or are conveniently prepared by methods well known to those skilled in the art. For example see Martin, I., et al. *Acta. Chem. Scand.* 1995 49 230 for the preparation of VII in which Y is —CH$_2$—O— and Q$^2$ is 4-pyridyl substituted by a 2-aminocarbonyl group (2-CONH$_2$).

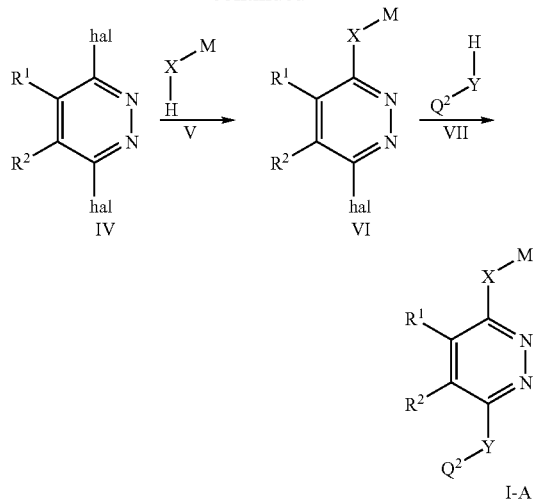

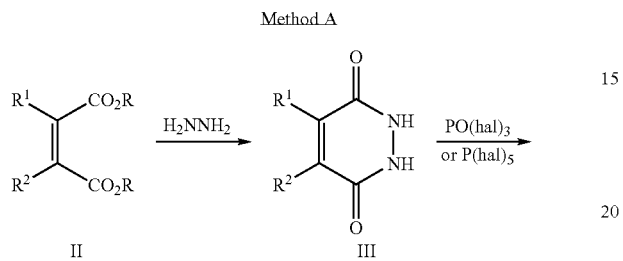

Reference Table for Preparation of Starting Material II

| Structure | Reference |
|---|---|
| 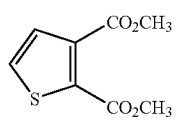 | For diacid: Heffner, R.; Joullie, M. Synth. Commun.. 1991 21(8&9) 1055. The diacid can be converted to dimethyl ester by reflux in methanol with catalytic sulfuric acid. |
| 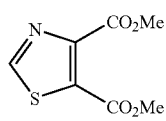 | Erlenmeyer, H.; von Meyenburg, H. Helv. Chim. Acta.. 1937 20 204. |
| 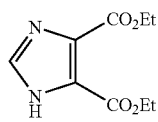 | Commercially available |
| 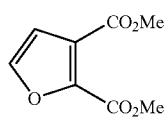 | Bickel, H.; Schmid, H., Helv. Chim. Acta.. 1953 36 664. |
| 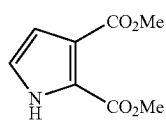 | Nicolaus, Mangoni. Gazz. Chim. Ital.. 1956 86 757. |
| 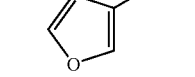 | Alder, Rickert. Chem. Ber.. 1937 70 1354. |
| 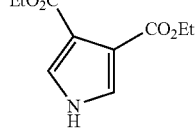 | Nicolaus, Mangom. Gazz. Chim. Ital.. 1956 86 757. |

| | |
|---|---|
| 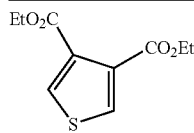 | Sice, J. J. Org. Chem.. 1954 19 70. |
| 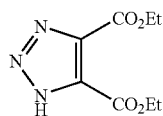 | Tanaka, Y. Tetrahedron. 1973 29 3271. |
| 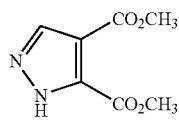 | Diacid: Tyupalo, N.; Semenyuk, T.; Kolbasina, O. Russ. J. Phys. Chem. 1992 66 463. The diacid can be converted to dimethyl ester by reflux in methanol with catalytic sulfuric acid. Alternatively, the diester is prepared by reaction of dimethyl acetylenedicarboxylate with diazomethane. |

General Method B—The compounds of formula I-B in which M, X, and $Q^2$ are as defined above and Y is —$CH_2$—O—, —$CH_2$—S—, —$CH_2$—NH—, —O—, —S—, or —NH— are conveniently prepared as shown in Method B. According to a procedure described in the literature (Tomisawa and Wang, Chem. Pharm. Bull., 21, 1973, 2607, 2612), isocarbostyril VIII is reacted with $PBr_5$ in a melt to form 1,4-dibromoisoquinoline IX. Intermediate IX is treated with a nucleophile of formula V in refluxing alcohol to furnish intermediate of formula X. Such condensations can also be done in a melt free of solvent and can be catalyzed by acids such as HCl or bases, such as triethylamine or 1,8-diazobicyclo[5.4.0]undec-7-ene (DBU). The compound of formula X is reacted with compounds of formula VII in a suitable aprotic solvent such as DMSO, DMF or solvent free often with a basic catalyst such as DBU or $CsCO_4$ at elevated temperatures to furnish invention compound of formula I-B. This method is most useful when Y is —$CH_2$—S— or —S—.

Method B

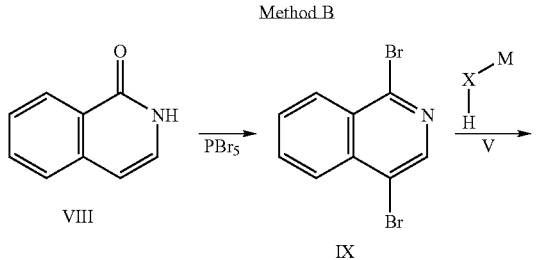

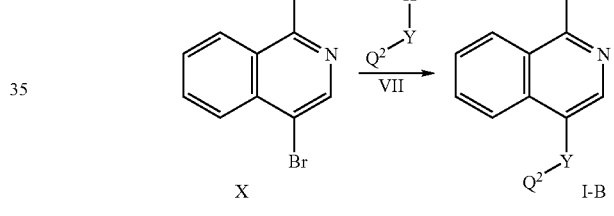

General Method C—The compounds of formula I-C in which M, X, $R^1$, $R^2$, m and $Q^2$ are defined as above are conveniently prepared according by a reaction sequence as shown in method C. In this method m is preferably 0 and $R^1$ and $R^2$ together with the carbons to which they are attached form a fused benzene or fused 5-member ring aromatic heterocycle. Starting material XI is either commercial or is prepared by one skilled in the art as shown in the reference table below. Starting material XI is reacted with urea or ammonia, usually at elevated temperature and pressure (in the case of ammonia), to form imide XII. The imide is reacted with an aldehyde XIII in acetic acid and piperidine at reflux to yield intermediate XIV. Reaction of XIV with sodium borohydride in methanol or other suitable solvents according to the general procedure described by I. W. Elliott and Y. Takekoshi (J. Heterocyclic Chem. 1976 13, 597) yields intermediate XV. Treatment of XV with a suitable halogenating agent such as $POCl_3$, $POBr_3$, $PCl_5$, $PBr_5$ or thionyl chloride yields halo intermediate XVI which is reacted with nucleophile of formula V in refluxing alcohol to furnish invention compound of formula I-C. Such condensations can also be done in a melt free of solvent and can be catalyzed by acids such as HCl or bases such as triethylamine or 1,8-diazobicyclo[5.4.0]undec-7-ene (DBU). Alternatively, reagent V can be condensed with intermediate XV be heating the two components with $P_2O_5$ in a melt to yield invention compound of structure I-C. This last method is especially effective when X is an amine linker.

Method C
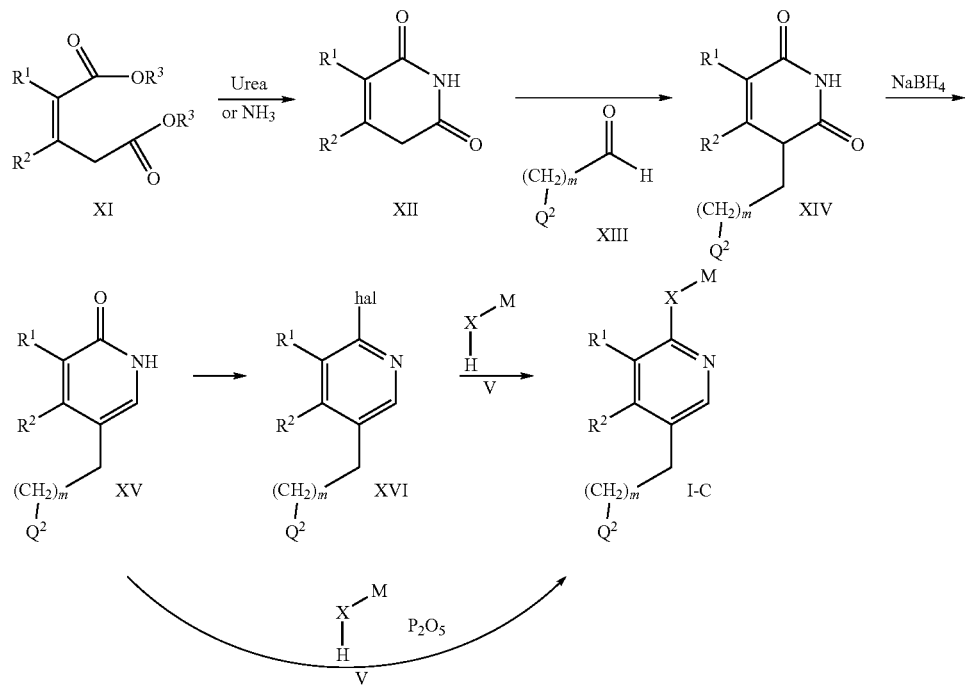
Reference Table for Preparation of Starting Materials
| | | |
|---|---|---|
| 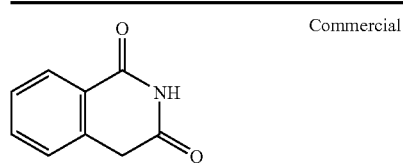 | Commercial | |
| 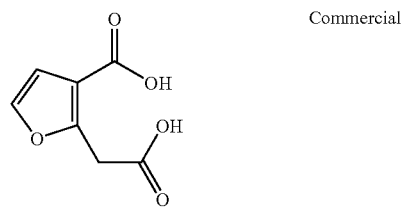 | Commercial | |
| 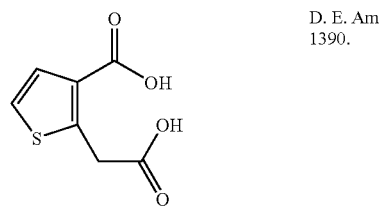 | D. E. Ames and O. Ribeiro, J. Chem. Soc., Perkin Trans. 1 1975, 1390. | |
| 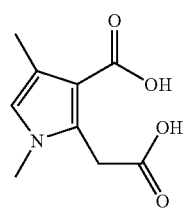 | J. R. Carson and S. Wong, J. Med. Chem. 1973, 16, 172. | |

-continued

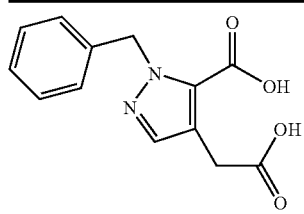 K. Yasuyuki, et al., J. Org. Chem. 1986, 51, 4150.

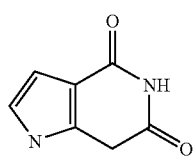 Schneller, et al., J. Med. Chem. 1978, 21, 990.

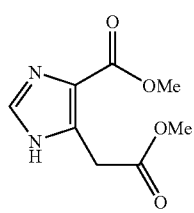 R. K. Robins et al., J. Org. Chem. 1963, 28, 3041.

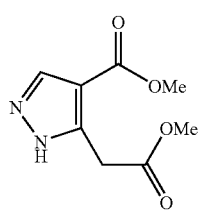 P. Gupta, et al., J. Heterocyci. Chem. 1986, 23, 59.

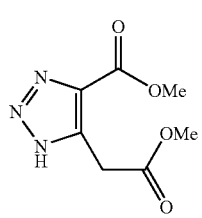 R. B. Meyer, et al., J. Heterocycl. Chem. 1980 17, 159.

General Method D—The compounds of formula I-D-1 in which $R^1$, $R^2$, $R^6$, M, X, Y, $G^3$ and Z are defined as above and q is 0 or 1 are conveniently prepared via a reaction sequence as shown in Method D. Thus, pyridine substituted pyridazines or pyridines (I-D-1) are functionalized into substituted 2-aminocarbonyl pyridines of formula (I-D-2) by the use of formamides (XVII) in the presence of hydrogen peroxide and iron salts, according to a procedure described in the literature (Minisci et al., *Tetrahedron*, 1985, 41, 4157). This method works best when $R^1$ and $R^2$ together constitute a fused aromatic heterocycle or fused aromatic carbocycle. In those cases that Z is CH and $R^1$ and $R^2$ do not form a fused aromatic, an isomeric side product in which Z is $CCONHR^6$ can be formed and, if so formed, is removed from the desired product by chromatography.

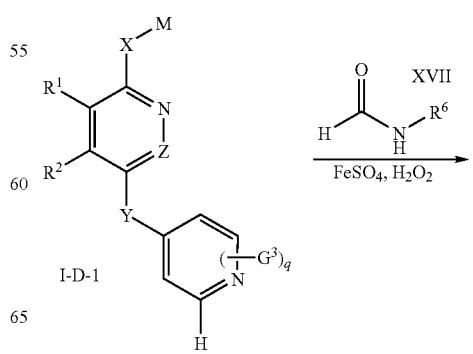

Method D

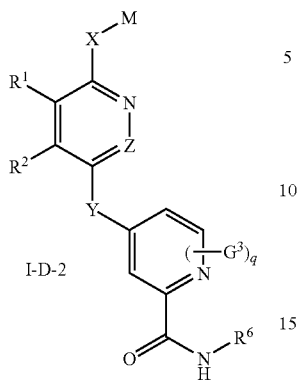

I-D-2

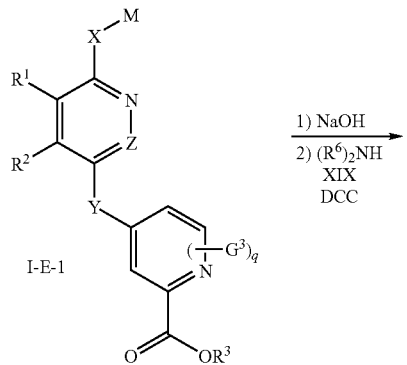

I-E-1

General Method E—The compounds of formula I-E-1 and I-E-2 in which $R^1$, $R^2$, $R^6$, M, X, Y, $G^3$, and Z are defined as above, q is 0 or 1, and $R^3$ is lower alkyl are conveniently prepared via a reaction sequence as shown in Method E. Thus, pyridine substituted pyridazines or pyridines (I-D-1) are functionalized into substituted 2-alkoxycarbonyl pyridines of formula (I-E-1) by the use of monoalkyloxalates (XVIII) in the presence of $S_2O_8^{-2}$, acid and catalytic amounts of $AgNO_3$, according to a procedure described in the literature (Coppa, F. et al., *Tetrahedron Letters*, 1992, 33 (21), 3057). Compounds of formula I-E-1 in which $R^3$ is H are then formed by hydrolysis of the ester with a base such as sodium hydroxide in methanol/water. Compounds of formula I-E-2 in which the $R^6$ groups are independently defined as above, but especially including those compounds in which neither $R^6$ is H, are conveniently prepared from the acid (I-E-1, $R^3$=H) by treatment with amine XIX in the presence of a coupling agent such as DCC (dicyclohexylcarbodiimide). This method works best when $R^1$ and $R^2$ together constitute a fused aromatic heterocycle or fused aromatic carbocycle. In those cases that Z is CH and $R^1$ and $R^2$ do not form a fused aromatic, an isomeric side product in which Z is $CCO_2R^3$ can be formed in the first step and, if so formed, is removed from the desired product by chromatography.

Method E

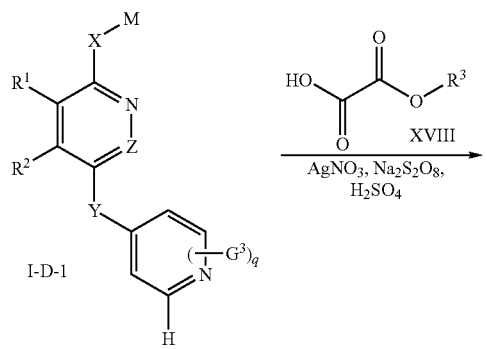

I-E-2

General Method F—The compounds of formula I-F in which M, $Q^2$ and X are defined as above, m is an integer of 1-5, and $R^1$ and $R^2$ together with the carbons to which they are attached form a fused 5-membered ring aromatic heterocycle can be prepared via a reaction sequence as shown in method F. The readily available heterocyclylcarboxylic acid starting material XX is reacted with butyl lithium followed by dimethylformamide to yield the aldehyde with structure XXI. Reaction of XXI with hydrazine yields pyridazinone XXII. Treatment of XXII with a suitable halogenating agent such as $POCl_3$, $POBr_3$, $PCl_5$, $PBr_5$ or thionyl chloride yields a halo intermediate which is reacted with nucleophile of formula V in refluxing alcohol to furnish intermediate compound of formula XXIII. Such condensations can also be done in a melt free of solvent and can be catalyzed by acids such as HCl or bases such as triethylamine or 1,8-diazobicyclo[5.4.0]undec-7-ene (DBU). Alternatively, reagent V can be condensed with intermediate XXII be heating the two components with $P_2O_5$ in a melt to yield XXII. This last method is especially effective when X is an amine linker. Formation and alkylation of the Reissert compound XXIII with halide XXIV is done as described by the general method of F. D. Popp, *Heterocycles*, 1980, 14, 1033 to yield the intermediate of structure XXV. Treatment of XXV with base then yields invention compound I-F.

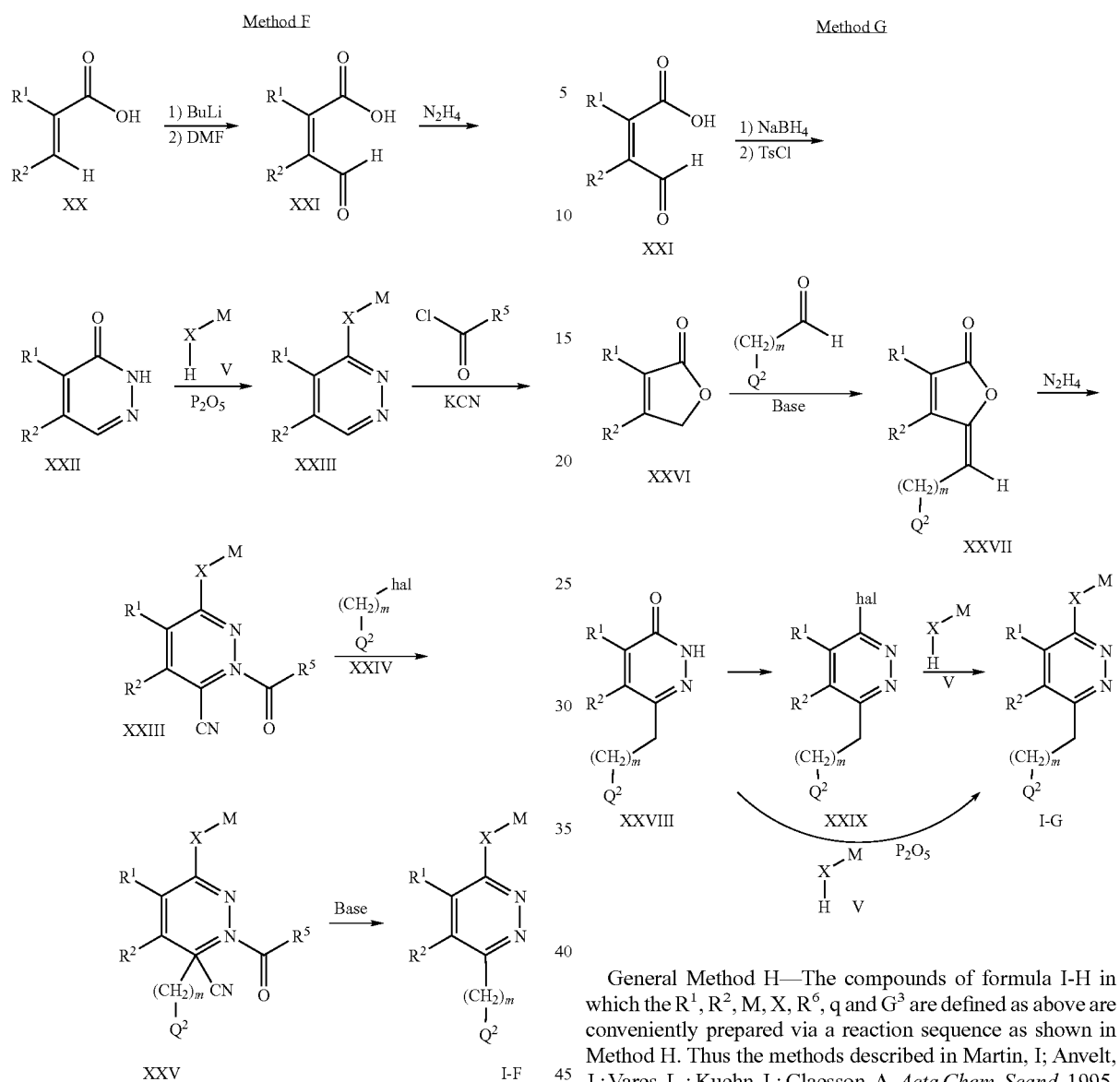

General Method G—The compounds of formula I-G in which M, Q² and X are defined as above, m is an integer of 1-4, and R¹ and R² together with the carbons to which they are attached form a fused 5-membered ring aromatic heterocycle can be prepared via a reaction sequence as shown in method G. Aldehyde XXI, from method F, can be reduced with sodium borohydride to yield a hyroxyacid which is lactonized using methods well known to those skilled in the art such as with toluenesulfonyl chloride to yield lactone XXVI. Condensation of intermediate XXVI with aldehyde XIII in the presence of a base such as sodium methoxide usually in a solvent such as methanol under reflux yields an intermediate of structure XXVII. Reaction of XXVII with hydrazine or preferably with hydrazine hydrate at a temperature of 100-150° C. leads to an intermediate of structure XXVIII. Conversion of intermediate XXVIII to invention compound of structure I-G is done by methods as described in method C by using XXVIII rather than XV.

General Method H—The compounds of formula I-H in which the R¹, R², M, X, R⁶, q and G³ are defined as above are conveniently prepared via a reaction sequence as shown in Method H. Thus the methods described in Martin, I; Anvelt, J.; Vares, L.; Kuehn, I.; Claesson, A. *Acta Chem. Scand.* 1995, 49, 230-232 or those of methods D or E above by substituting readily available pyridine-4-carboxylic ester XXX for I-D-1 are used to convert XXX into XXXI. Reduction of the ester as described by Martin, et al. above is next done with a mild reducing agent such as NaBH₄ such that the amide substituent is left unchanged to yield alcohol XXXII. This alcohol is then heated with a base such as DBU or CsCO₄ with halopyridazine VI from method A under anhydrous conditions to yield the invention compound with formula I-H.

Method H

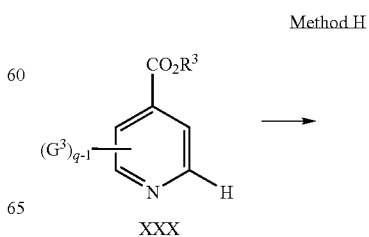

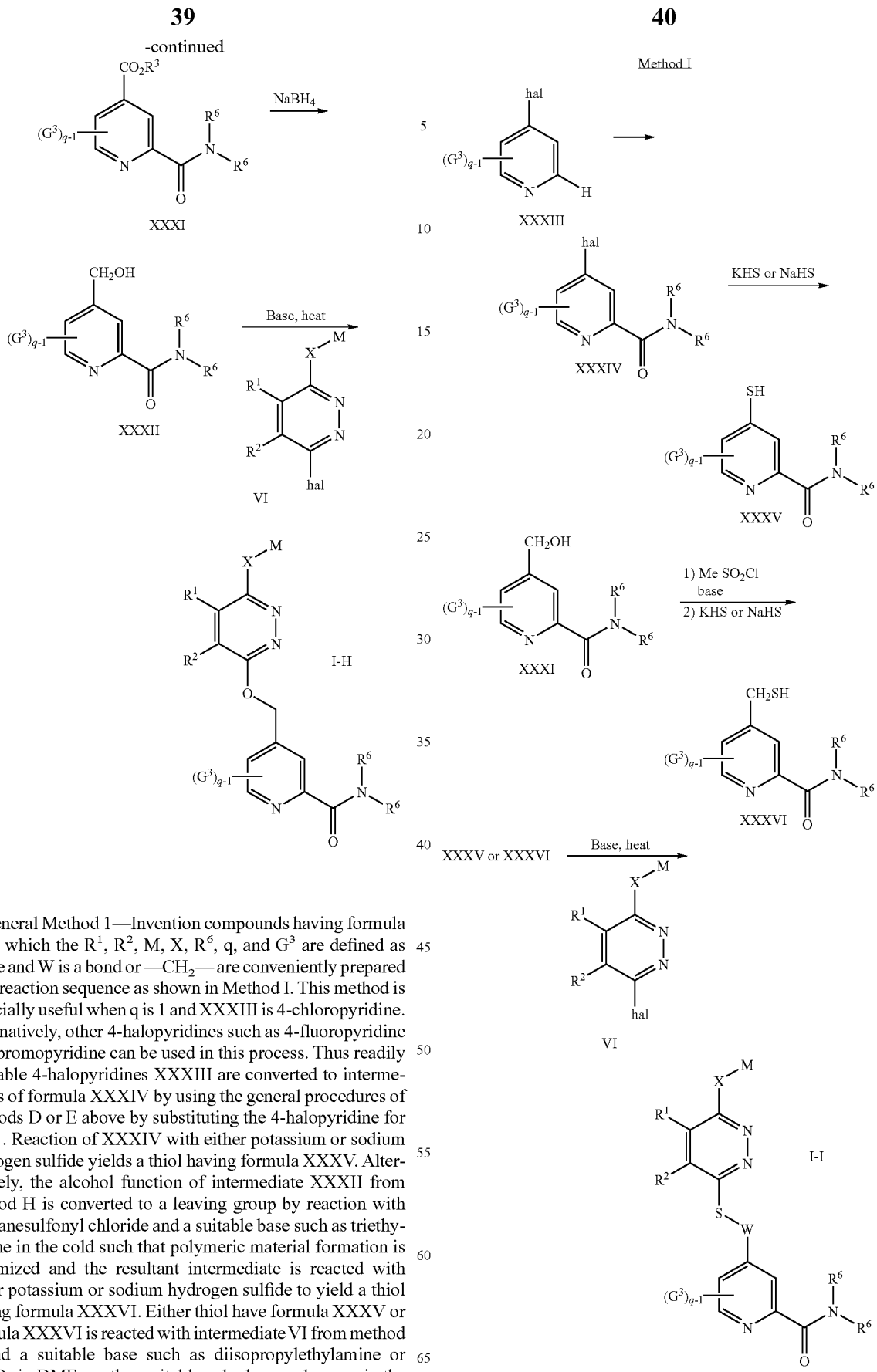

General Method 1—Invention compounds having formula I-I in which the $R^1$, $R^2$, M, X, $R^6$, q, and $G^3$ are defined as above and W is a bond or —$CH_2$— are conveniently prepared via a reaction sequence as shown in Method I. This method is especially useful when q is 1 and XXXIII is 4-chloropyridine. Alternatively, other 4-halopyridines such as 4-fluoropyridine or 4-bromopyridine can be used in this process. Thus readily available 4-halopyridines XXXIII are converted to intermediates of formula XXXIV by using the general procedures of methods D or E above by substituting the 4-halopyridine for I-D-1. Reaction of XXXIV with either potassium or sodium hydrogen sulfide yields a thiol having formula XXXV. Alternatively, the alcohol function of intermediate XXXII from method H is converted to a leaving group by reaction with methanesulfonyl chloride and a suitable base such as triethylamine in the cold such that polymeric material formation is minimized and the resultant intermediate is reacted with either potassium or sodium hydrogen sulfide to yield a thiol having formula XXXVI. Either thiol have formula XXXV or formula XXXVI is reacted with intermediate VI from method A and a suitable base such as diisopropylethylamine or $CsCO_4$ in DMF or other suitable anhydrous solvent or in the absence of solvent to yield I-D-9.

General Method J—Invention compounds such as those having formula I-J-1 or I-J-2 in which the $R^1$, $R^2$, M, X, W, and $G^3$ are defined as above and having a sulfoxide or sulfone within the structure are conveniently prepared via a reaction sequence as shown in Method J. Reaction of compounds of this invention that contain a thioether group either as part of a substituent $G^1$, $G^3$, or $G^4$ or as part of Y as shown in the representative structure I-I from Method I can be converted to the invention compounds with a sulfoxide moiety such as I-J-1 by treatment with one equivalent of m-chloroperbenzoic acid in methylene chloride or chloroform (MCPBA, Synth. Commun., 26, 10, 1913-1920, 1996) or by treatment with sodium periodate in methanol/water at between 0° C. and room temperature (J. Org. Chem., 58, 25, 6996-7000, 1993). The expected side products consisting of mixtures of various N oxides and the sulfone I-J-2 can be removed by chromatography. The sulfone I-J-2 is obtained by the use of an additional equivalent of MCPBA or preferably by use of potassium permanganate in acetic acid/water (Eur. J. Med. Chem. Ther., 21, 1, 5-8, 1986) or by use of hydrogen peroxide in acetic acid (Chem. Heterocycl. Compd., 15, 1085-1088, 1979). In those cases that unwanted N oxides become a significant product, they can be converted back to the desired sulfoxides or sulfones by hydrogenation in ethanol/acetic acid with palladium on carbon catalysts (Yakugaku Zasshi, 69, 545-548, 1949, Chem. Abstr. 1950, 4474).

Method J

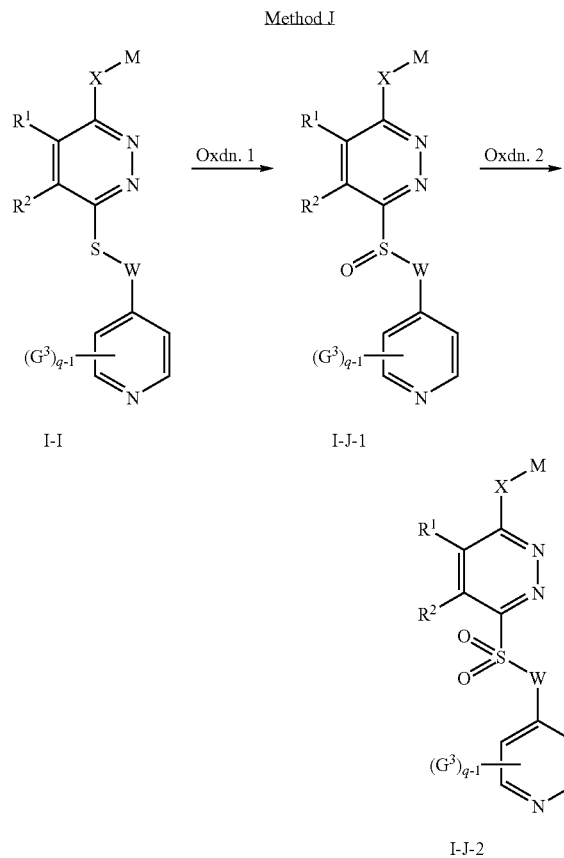

materials of structure XXXVII by methods known in the literature. For example XXXVII wherein $R^1$ and $R^2$ together with the carbons to which they are attached form a 2,3-substituted thiophene, furan, pyrrole, cyclopentadienyl, oxazole or thiazole are prepared using the general chemistry given in J. Org. Chem., 1981, 46, 211 and hydrolizing the initially formed tert-butyl ester with trifluoroacetic acid. The pyrazole starting material can be prepared by reacting 2-oxo-3-pentyn-1,5-dioic acid (J. Chem. Phys. 1974, 60, 1597) with diazomethane. The starting material wherein $R^1$ and $R^2$ together with the carbons to which they are attached form a phenyl are prepared by the methods of Cymerman-Craig et al., Aust. J. Chem. 1956, 9, 222, 225. Compounds of formula XXXVII in which $R^1$ and $R^2$ are lower alkyl are conveniently prepared according to procedures given in patent CH 482415 (Chem. Abstr. 120261u, 1970). The crude diacid of formula XXXVII is subsequently treated with hydrazine to furnish pyridazinone XXXVIII (for specific reaction conditions see Vaughn, W. R.; Baird, S. L. J. Am. Chem. Soc. 1946 68 1314). Pyridazinone XXXVIII is treated with a chlorinating agent such as phosphorous oxychloride to yield an intermediate dichloro species which undergoes hydrolysis upon aqueous workup to furnish chloropyridazine XXXIX. Chloro acid XXXIX is treated with a nucleophile of formula V in the presence of a base such as sodium hydride in a solvent such as DMF or in the absence of a solvent. The resultant acid XXXX is reduced with a reducing agent such as $BH_3 \cdot THF$ according to the procedure of Tilley, J. W.; Coffen D. L. Schaer, B. H.; Lind, J. J. Org. Chem. 1987 52 2469. Product alcohol XXXXI is reacted with a base and optionally substituted 4-halo-pridyl, optionally substituted 4-halo-pyrimidyl or optionally substituted 4-halo-pyridazyl (XXXXII) to furnish invention compound of formula I-K (for specific reaction conditions see Barlow, J. J.; Block, M. H.; Hudson, J. A.; Leach, A.; Longridge, J. L.; Main, B. g.; Nicholson, S. J. Org. Chem. 1992 57 5158).

Method K

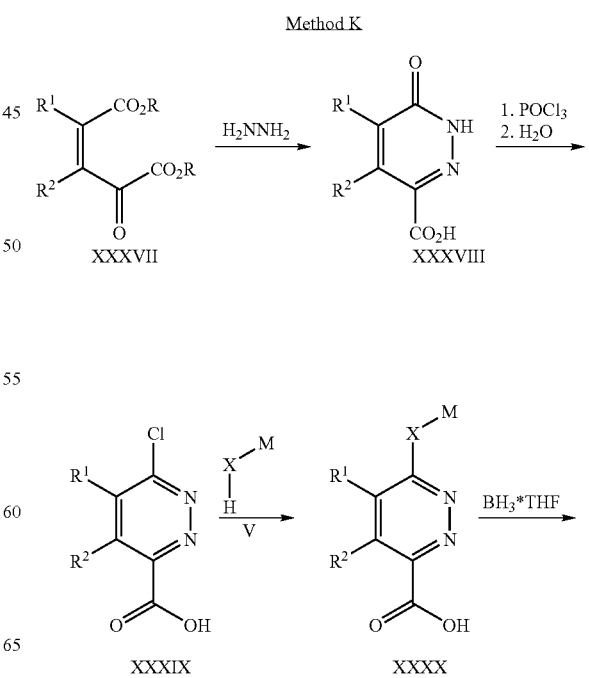

General Method K—Invention compounds having formula I-K in which the $R^1$, $R^2$, M, X, and $Q^1$ are defined as above are conveniently prepared via a reaction sequence as shown in Method K. One skilled in the art prepares starting

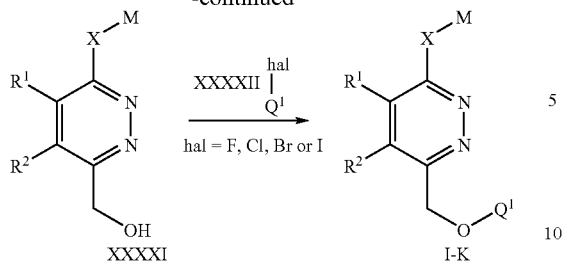

General Method L—Invention compounds having formula I-L in which the $R^1$, $R^2$, M, X, and $Q^1$ are defined as above are conveniently prepared via a reaction sequence as shown in Method L. Thus alcohol of formula XXXXI from method K is reacted with methanesulfonyl chloride in the presence of a suitable base followed by potassium or sodium hydrogen sulfide to yield thiol XXXXIII. The thiol is then reacted with 4-halopyridine XXXXII from method K in the presence of a suitable base such as triethylamine to yield invention compound I-K. Alternatively, XXXXI is converted to halo intermediate of formula XXXXIV by methods well known to those skilled in the art and the halide is reacted with thiol XXXXV to yield I-K. Intermediate XXXXIV can also be converted to intermediate XXXXIII by treatment with KHS or NaHS. Reagents XXXXV are either commercially available such as 4-mercaptopyridine or can be prepared by one skilled in the art such as by method I above.

Method L

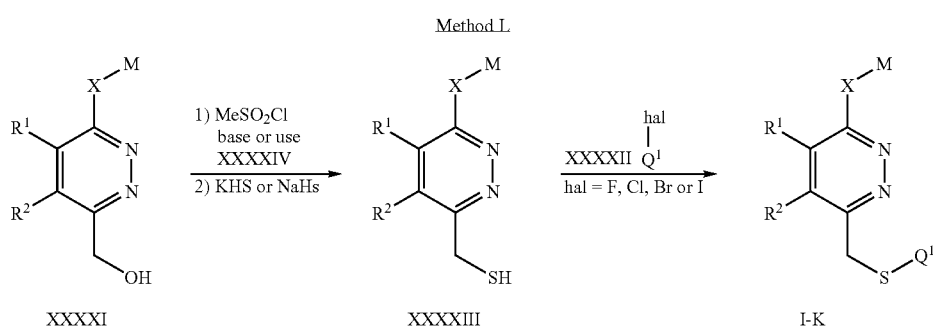

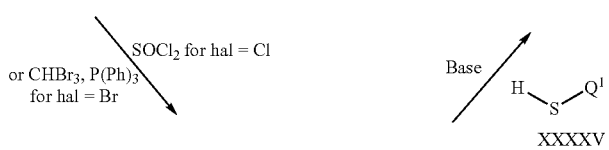

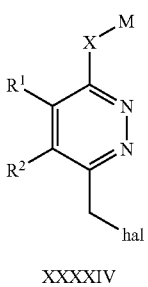

EXPERIMENTAL

Example 1

Preparation of 1-(4-chlorophenylamino)-4-(4-pyridylthio)isoquinoline

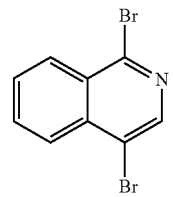

Step 1: Preparation of Intermediate A: A mixture of 2.90 g, 19.07 mMol of isocarbostyril and 14.40 g, 33.68 mMol of phosphorus pentabromide were allowed to melt together at 140° C. The melt turned into a red liquid and after about 10 minutes the reaction mixture solidified and was cooled. The reaction mixture was crushed up and dumped into ice water. The resulting solid was filtered and air-dried. wt. 5.50 g, 96% yield, mp.=94-96'. $R_f$=0.66 in 40% ethyl acetate in hexanes.

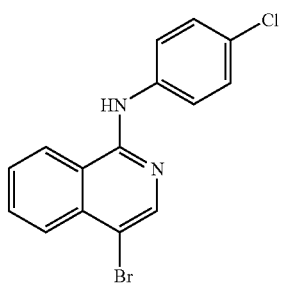

Step 2: A mixture of 1.00 g, 3.49 mMol of 1,4-dibromoisoquinoline (Intermediate A) from step 1 and 4-chloroaniline were melted together at 140°. The reaction mixture turned into a deep red liquid and after about 10 minutes the reaction mixture solidified and was done. The reaction mixture was broken up and triturated with a 50/50 methanol/THF mixture then filtered and air dried without further purification. wt. 0.75 g, 64.4%, mp.=260-263°. $R_f$=0.58 in 40% ethyl acetate in hexanes.

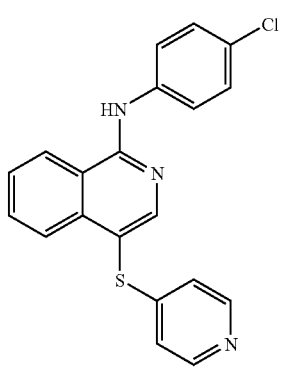

Step 3: A mixture of 0.05 g, 0.1498 mMol of 1-(4-chloroaniline)-4-bromoisoquiniline and 0.02 g, 0.18 mMol of 4-mercaptopyridine were combined and melted together at 140° for about 10 minutes. The resulting reaction mixture was purified on a 1000 micron prep plate using 5% methanol in hexanes as the solvent. wt. 0.0103 g, 19% yield, mp. 192-195°. $R_f$=0.50 in 40% ethyl acetate in hexanes.

Example 2

Preparation of
1-(indan-5-ylamino)-4-(4-pyridylthio)isoquinoline

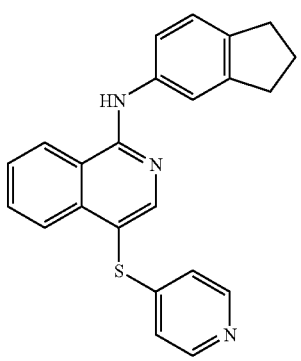

The procedure used for the preparation of Example 1 was used to prepare the title compound by substituting 5-aminoindane for 4-chloroaniline in step 2. Mp. 100-103°, TLC $R_f$ 0.40 (40% ethyl acetate in hexanes).

Example 3

Preparation of 1-(benzothiazol-6-ylamino)-4-(4-pyridylthio)isoquinoline

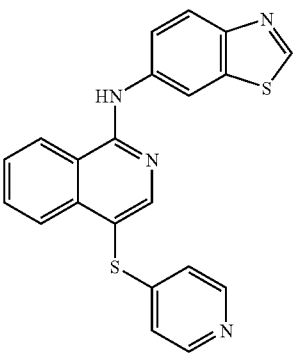

The procedure used for the preparation of Example 1 was used to prepare the title compound by substituting 6-aminobenzothiazole for 4-chloroaniline in step 2.

TLC $R_f$ 0.36 (5% methanol/methylene chloride); MS=387

Example 4

Preparation of 1-(4-chlorophenylamino)-4-(4-pyridylmethyl)isoquinoline

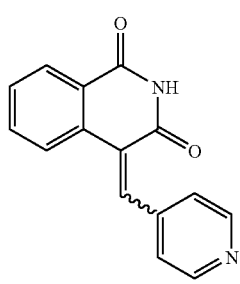

Step 1: A mixture of homophthalimide (770 mg, 4.78 mmol), 4-pyridinecarboxaldehyde (0.469 mL, 4.78 mmol) and piperidine (0.5 mL) in acetic acid (25 mL) was heated at reflux for 1 h. The resultant solution was cooled to room temperature. The solid product was removed by filtration, washed by water (4×10 mL) and dried under vacuum to afford 920 mg (3.67 mmol, 77% yield) of a mixture of Z and E isomers of the above compound. $^1$H-NMR (DMSO-d$_6$) complex proton signals shown in aromatic region due to existence of both E and Z isomers. MS ES 251 (M+H)$^+$, 252 (M+2H)$^+$.

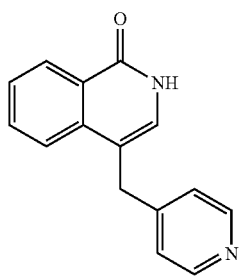

Step 2: To a suspension of starting material (1.70 g, 6.8 mmol) in methanol (250 mL) at 0° C. was added slowly sodium borohydride (3.0 g, 79 mmol). The mixture was allowed warmed to rt and continued stirring for 1 hr. The reaction was quenched with water (10 mL) and stirred for 10 minutes. The resulting mixture was concentrated to remove solvent. To the residue was added water with ice (100 mL), and adjusted the pH=2 with 2 N HCl solution. Stirred for 10 minutes, added 2 N NaOH until pH of the solution was about 11. The resulting solution was extracted by CH$_2$Cl$_2$ (4×100 mL). The combined organic layers were collected, dried over MgSO$_4$ and concentrated. The residue was purified by column chromatography (1:10 v/v methanol-dichloromethane) to afford 400 mg of the title compound as a solid (1.70 mmol, yield 25%). $^1$H-NMR (MeOH-d$_4$) 8.33 to 8.39 (m, 4H), 7.50 to 7.68 (m, 3H), 7.30-7.31 (m, 2H), 7.14 (s, 1H), 4.15 (s, 2H); MS ES 237 (M+H)$^+$, 238 (M+2H); TLC (1:10 v/v methanol-dichloromethane) R$_f$=0.40.

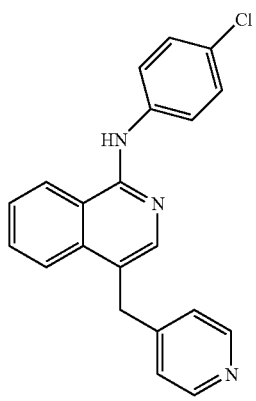

Step 3: A mixture of 4-chloroaniline (178 mg, 1.40 mmol), phosphorus pentoxide (396 mg, 1.40 mmol) and triethylamine hydrochloride (193 mg, 1.40 mmol) was heated and stirred under argon at 200° C. for 1.5 h or until a homogenous melt has formed. To the melt was added starting material (82 mg, 0.35 mmol). The reaction mixture was stirred at 200° C. for 2 h. The resultant solid black mass was cooled to 100° C. Methanol (5 mL) and water (10 mL) were added and the reaction mixture was sonicated until the black mass had become soluble. Dichloromethane (40 mL) was added and concentrated ammonia (~2 mL) was added to adjust the mixture to pH=10. The organic layer was separated, and the aqueous layer was extracted with dichloromethane (3×20 mL). The combined organic layers were dried over MgSO$_4$, filtered, and concentrated. Purification by preparative TLC plate (1:10 v/v methanol-dichloromethane) yielded 26 mg (0.08 mmol, 22% yield) of the title compound as a yellow solid. $^1$H-NMR (MeOH-d$_4$) 8.37 (d, J=7.8 Hz, 3H), 7.86 (s, 1H), 7.55 to 7.77 (m, 5H), 7.27 to 7.33 (m, 4H), 4.31 (s, 2H); MS ES 346 (M+H)$^+$; TLC (1:10 v/v methanol-dichloromethane) R$_f$=0.45.

Example 5

Preparation of 1-(benzothiazol-6-ylamino)-4-(4-pyridylmethyl)-isoquinoline

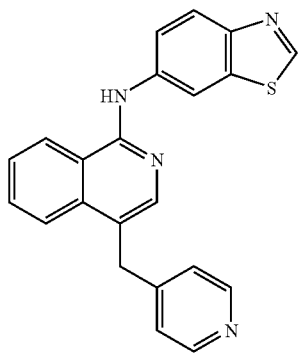

The procedure used for the preparation of Example 4 was used to prepare the title compound by substituting 6-aminobenzothiazole for 4-chloroaniline in step 3. $^1$H-NMR (MeOH-d$_4$) 9.08 (s, 1H), 8.37 to 8.59 (m, 4H), 7.79 to 8.01 (m, 2H), 7.60 to 7.78 (m, 4H), 7.30 (d, 2H), 4.34 (s, 2H); MS ES 369 (M+H)$^+$; TLC (1:4 v/v hexane-ethyl acetate) R$_f$=0.20.

Example 6

Preparation of 1-(indan-5-ylamino)-4-(4-pyridylmethyl)-isoquinoline

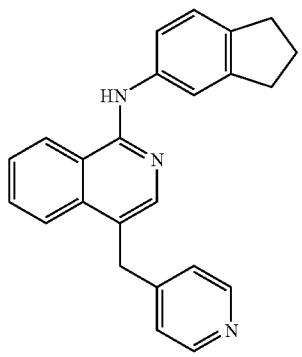

The procedure used for the preparation of Example 4 was used to prepare the title compound by substituting 5-aminoindane for 4-chloroaniline in step 3. $^1$H-NMR (MeOH-d$_4$) 8.35 (m, 3H), 7.46 to 7.77 (m, 5H), 7.15 to 7.27 (m, 4H), 4.26 (s, 2H), 2.87 to 2.90 (m, 4H), 2.05 to 2.10 (m, 2H); MS ES 352 (M+H)$^+$; TLC (1:4 v/v hexane-ethyl acetate) R$_f$=0.25.

Example 7

Preparation of 1-(3-fluoro-4-methylphenylamino)-4-(4-pyridylmethyl)-isoquinoline

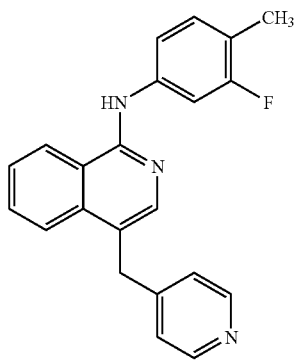

The procedure used for the preparation of Example 4 was used to prepare the title compound by substituting 3-fluoro-4-methylaniline for 4-chloroaniline in step 3. $^1$H-NMR (MeOH-d$_4$) 8.34 (d, 3H), 7.87 (s, 1H), 7.54 to 7.69 (m, 4H), 7.10 to 7.31 (m, 4H), 2.22 (s, 3H); MS ES 344 (M+2H)$^+$; TLC (1:4 v/v hexane-ethyl acetate) R$_f$=0.20.

Example 8

Preparation of 4-(4-chlorophenylamino)-7-(4-pyridylmethoxy)thieno-[2,3-d]pyridazine

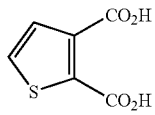

Step 1: A dry, 2 L, 3-necked, round-bottomed flask was equipped with a mechanical stirrer and addition funnel. To the flask was added 2-thiophenecarboxylic acid (25 g, 195 mmol) in anhydrous THF (500 mL) under argon. The mixture was cooled to −78° C. with a dry ice-isopropanol bath and allowed to stir for 30 min. n-Butyllithium in Hexanes (2.5 M, 172 mL) was added dropwise over 30 min. The reaction was kept at −78° C. for an additional hour with stirring then placed under an atmosphere of dry carbon dioxide. With addition of the carbon dioxide the reaction became thick. The reaction remained at −78° C. for an additional hour before warming to −10° C. The reaction was quenched with 2 N HCl (213 mL) and allowed to reach rt. The layers were separated and the aqueous layer was extracted with EtOAc (3×200 mL). The organic layers were combined, dried (Na$_2$SO$_4$) and concentrated by rotary evaporation. The brown solid was crystallized from hot isopropanol and dried overnight under vacuum. Desired thiophene-2,3-dicarboxylic acid was obtained (27.3 g, 159 mmol; 82% yield); $^1$H NMR (DMSO-d$_6$) 7.69 (d, J=1.5, 1), 7.38 (d, J=4.8, 1); ES MS (M+H)$^+$=173; TLC (Chloroform-MeOH-water, 6:4:1); R$_f$=0.74.

Step 1A: Alternatively, 3-thiophenecarboxylic acid rather than 2-thiophenecarboxylic acid has been used in step 1 to yield the same product.

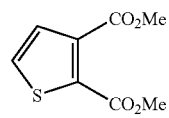

Step 2: A 1 L, round-bottomed flask was equipped with a stir bar and reflux condenser. To the flask was added the product of step 1 (62 g, 360 mmol) in MeOH (500 mL) with a catalytic amount of H$_2$SO$_4$ (~5 mL). The reaction was heated to reflux and stirred for 24 h. The reaction was cooled to rt and concentrated rotary evaporation. The brown mixture was purified by silica gel chromatography (Hexane-EtOAc 80:20 gradient to 60:40). Desired dimethyl thiophene-2,3-dicarboxylate was obtained (21.2 g, 106 mmol; 31% yield); $^1$H NMR (DMSO-d$_6$) 7.93 (d, J=4.8, 1), 7.35 (d, J=4.8, 1), 3.8 (d, J=1, 6); ES MS (M+H)$^+$=201; TLC (Hexane-EtOAc, 70:30); R$_f$=0.48.

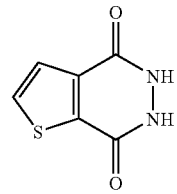

Step 3: A 250 mL, round-bottomed flask was equipped with a stir bar and reflux condenser. To the flask was added the product of step 2 (16 g, 80 mmol), hydrazine hydrate (6.6 mL, 213 mmol), and EtOH (77 mL) and refluxed for 2.5 h. The reaction was cooled to rt and concentrated by rotary evaporation. Water (50 mL) was added and the filtrate was separated from the insoluble solids. The aqueous layer was concentrated by rotary evaporation to give a pale yellow solid. The solid was dried in a vacuum oven overnight at 50° C. Desired thieno[2,3-d]pyridazin-4,7-dione was obtained (12 g, 71 mmol; 89% yield); $^1$H NMR (DMSO-d$_6$) 7.85 (d, J=5.1, 1), 7.42 (d, J=5.1, 1); ES MS (M+H)$^+$=169; TLC (dichloromethane-MeOH, 60:40); R$_f$=0.58.

Step 4: Preparation of Intermediate B: A 250 mL, round-bottomed flask was equipped with a stir bar and reflux condenser. To the flask was added the product of step 3 (2.5 g, 14.8 mmol), phosphorus oxychloride (45 mL, 481 mmol), and pyridine (4.57 mL, 55 mmol) and refluxed for 2.5 h. The reaction was cooled to rt and poured over ice. The mixture was separated and the aqueous layer was extracted with chloroform (4×75 mL). The organic layers were combined, dried (Na$_2$SO$_4$) and concentrated by rotary evaporation to give a dark yellow solid. Desired 4,7-dichlorothieno[2,3-d]pyridazine (Intermediate B; 1.5 g, 7.3 mmol; 49% yield); mp=260-263° C.; $^1$H NMR (DMSO-$d_6$) 8.55 (d, J=5.7, 1), 7.80 (d, J=5.7, 1); ES MS (M+H)$^+$=206; TLC (hexane-EtOAc, 70:30); $R_f$=0.56. See also Robba, M.; Bull. Soc. Chim. Fr.; 1967, 4220-4235.

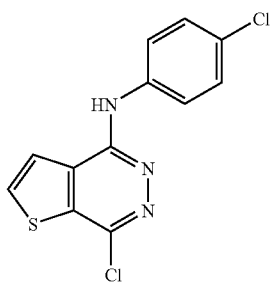

Step 5: A 250 mL, round-bottomed flask was equipped with a stir bar and reflux condenser. To the flask was added the product of step 4 (7.65 g, 37.3 mmol), 4-chloroaniline (4.76, 37.3 mmol) in EtOH (75 mL). The mixture was refluxed for 3 h. An orange solid precipitated from the reaction after 3 h. The reaction was cooled to rt and the solid was collected by filtration and washed with hexane. The desired 7-chloro-4-(4-chlorophenylamino)thieno[2,3-d]pyridazine was obtained (6.5 g, 21.9 mmol; 60% yield); mp=139-142° C.; ES MS (M+H)$^+$=297; TLC (Hexane-EtOAc, 60:40); $R_f$=0.48.

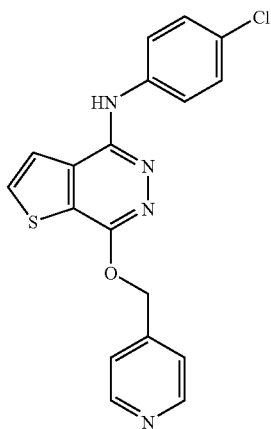

Step 6: A 150 mL, round-bottomed flask was equipped with a stir bar and reflux condenser. To the flask was added the product of step 5 (0.33 g, 1.1 mmol), 4-pyridylcarbinol (1.2 g, 11.2 mmol) in DBU (2.5 mL, 16.7 mmol) and the mixture was heated to 125° C. for 24 hours. EtOAc (10 mL) was added to the reaction while hot and then the reaction was poured into water (10 mL). The layers were separated and the aqueous layer was extracted with EtOAc (3×10 mL). The organic layers were combined, dried (MgSO$_4$) and concentrated by rotary evaporation. The resulting mixture was purified by silica gel chromatography (dichloromethane-methanol-acetone, 90:5:5) to give a pale yellow solid. The desired title compound was obtained (0.03 g, 0.08 mmol; 7.3% yield); mp=203-205° C. dec; ES MS (M+H)$^+$=369; TLC (dichloromethane-methanol-acetone, 95:2.5:2.5); $R_f$=0.56.

Example 9

Preparation of 4-(4-chlorophenylamino)-7-(4-pyridylmethoxy)furo[2,3-d]pyridazine

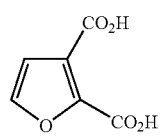

Step 1: n-Butyllithium (2.5M in hexanes, 196 mL, 491 mmol) was introduced into a dry 3 L 3-necked flask fitted with an addition funnel, argon inlet, and mechanical stirrer. The mixture was diluted with dry THF (500 mL), and cooled to −78° C. 3-furoic acid (25 g, 223 mmol) was added as solution in THF (500 mL) dropwise. The mixture was stirred for 1.5 h, at which point dry carbon dioxide was bubbled through the reaction mixture for 1 h. After warming gradually to −10° C., the resultant thick white slurry was treated with aqueous HCl (2 N, 446 mL). The two layers were separated, and the aqueous layer was extracted with EtOAc (3×300 mL). The combined organics were dried (Na$_2$SO$_4$), filtered, and concentrated to afford crude furan-2,3-dicarboxylic acid as an orange solid (44 g) which was used without further purification. $^1$H NMR (300 MHz, $d_6$-acetone) δ 7.06 (d, J=1.7, 1), 7.97 (d, J=1.7, 1), 10.7 (bs, 2H); TLC (CHCl$_3$/MeOH/H$_2$O 6:4:1) $R_f$=0.56.

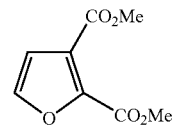

Step 2: A dry 500 mL round bottomed flask was equipped with a stir bar and an argon inlet. The flask was charged with the crude diacid prepared in Step 1 (44 g) dissolved in MeOH (250 mL). To the reaction mixture was added chlorotrimethylsilane (80 mL, 630 mmol) portionwise. After stirring at room temperature for 15.5 h, the solution was concentrated to an oil and silica (5 g) was added. The mixture was suspended in MeOH (100 mL), and the volatiles were removed. Suspension in MeOH (100 mL) and the removal of the volatiles was repeated an additional two times. The residue was applied directly to the top of a flash chromatography column and was eluted hexanes/EtOAc 60:40 to yield dimethyl furan-2,3-dicarboxylate as an orange oil (38 g, 93% for Step 1 and Step 2 combined). $^1$H NMR (300 MHz, CDCl$_3$) δ 3.81 (s, 3), 3.86 (s, 3), 6.71 (d, J=2.8, 1), 7.46 (d, J=2.8, 1); TLC (hexanes/EtOAc 60:40) $R_f$=0.46.

Tr;;31

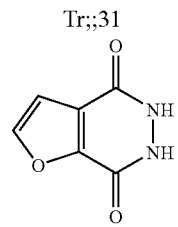

Step 3: A 500 mL round bottomed flask fitted with an argon inlet, a reflux condenser, and a stir bar was charged with dimethyl furan-2,3-dicarboxylate (44 g, 236 mmol) dissolved in EtOH (250 mL). Hydrazine hydrate (55% $N_2H_4$, 40 mL, 3.0 mmol) was added to the solution, and the reaction mixture was warmed to reflux. A yellow solid slowly precipitated over the course of 5.5 h, at which point the mixture was cooled to room temperature. The volatiles were removed under reduced pressure to furnish a yellow paste which was suspended in water and filtered. The yellow solid was washed with water and transferred to a 500 mL round bottomed flask fitted with an argon inlet, a reflux condenser, and a stir bar. The solid was suspended in aqueous HCl (2N, 200 mL), and the mixture was warmed to reflux. After heating for 4 h, the orange slurry was cooled to room temperature and filtered. The solid was washed thoroughly with water and dried under vacuum to yield 4,7-dioxo[2,3-d]furopyridazine as an orange solid (21.5 g, 60%). $^1$H NMR (300 MHz, $d_6$-DMSO) δ 7.00 (d, J=2.1, 1), 8.19 (d, J=2.1, 1H), 11.7 (bs, 2H).

Step 4: Preparation of Intermediate C: A 1 L round bottomed flask was fitted with a reflux condenser, a stir bar, and an argon inlet. The furan from Step 3 (15.5 g, 102 mmol) was added to a mixture of phosphorous oxychloride (300 mL) and pyridine (30 mL), and the resultant orange suspension was warmed to reflux. After heating the reaction mixture for 4 h, the volatiles were removed by rotary evaporation. The residue was poured onto ice, and the aqueous mixture was extracted with $CHCl_3$ (4×250 mL). The combined organics were washed with brine, dried ($MgSO_4$) and concentrated to afford 4,7-dichloro[2,3-d]furopyridazine (Intermediate C, 11.3 g, 59%) as an orange-red solid which was used without further purification. TLC (hexanes/EtOAc) $R_f$=0.352; $^1$H NMR (300 MHz, $d_6$-DMSO) δ 7.40 (d, J=2.0, 1), 8.63 (d, J=2.0, 1).

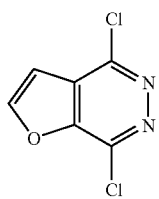

A

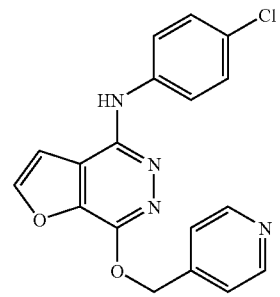

B

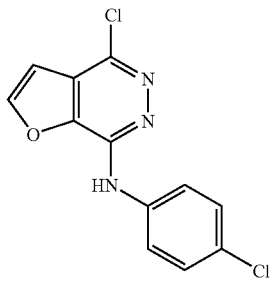

Step 5: A 100 mL round bottomed flask fitted with a stir bar, an argon inlet, and a reflux condenser was charged with the product of Step 4 (1.50 g, 7.98 mmol) dissolved in ethanol (40 mL). Chloroaniline was added to this mixture (1.02 g, 7.98 mmol), and the resultant suspension was warmed to reflux. After heating for 4 h, the mixture was concentrated by rotary evaporation. The crude orange solid was applied to the top of a flash column and eluted with $CH_2Cl_2$/MeOH 97:3 to afford a mixture of 4-chloro-7-[N-(4-chlorophenyl)amino][2,3-d]furopyridazine and 7-chloro-4-[N-(4-chlorophenyl)amino][2,3-d]furopyridazine as a yellow powder (1.2 g, 55%). TLC ($CH_2Cl_2$/MeOH 97:3); $R_f$=0.7; $^1$H NMR (300 MHz, $d_6$-DMSO) δ major isomer (A) 7.40 (d, J=8.9, 2), 7.45 (d, J=2.0, 1), 7.87 (d, J=9.2, 2), 8.34 (d, J=2.0, 1) 9.62 (s, 1); minor isomer (B) 7.28 (d, J=2.0, 1), 7.40 (d, J=8.9, 2), 7.87 (d, J=9.2, 2), 8.48 (d, J=2.1, 1), 9.88 (s, 1).

Step 6: A 25 mL round bottomed flask was fitted with an argon inlet, a stir bar, and a reflux condenser. The product of step 5 (400 mg, 1.4 mmol) was combined with 4-pyridylcarbinol (782 mg, 7.17 mmol) and 1,8-diazabicyclo[5.4.0]undec-7-ene (2.5 mL 16.7 mmol), and the slurry was warmed to 125° C. After stirring for 24, the reaction was cooled, applied directly to the top of a flash column, and eluted with $CH_2Cl_2$/MeOH 95:5. The resultant yellow oil was rechromatographed under the same conditions to yield the title compound as part of a mixture of three components. HPLC separation ($C_{18}$ column $CH_3CN/H_2O$ 10:90 gradient to 100:0) furnished the title compound as an off white solid (13.7 mg, 3%). TLC ($CH_2Cl_2$/MeOH 95:5)=0.19; MP 198° C.; $^1$H NMR (300 MHz, $CDCl_3$) δ 5.60 (s, 2), 6.6 (d, J=2.1, 1), 7.18-7.20 (m, 2), 7.35-7.43 (m, 6), 7.66 (d, J=2.1, 1) 8.54 (d, J=5.6, 2).

Steps 5A and 6A: Alternatively 4,7-dibromo[2,3-d]furopyridazine (Intermediate G below) is used to prepared the title compound by following step 5 but substituting the dibromo intermediate for the dichloro intermediate. Step 6A is conducted by melting the two components together in the presence of $CsCO_4$ rather than 1,8-diazabicyclo[5.4.0]undec-7-ene. The crude product is purified as above.

Intermediates D to G: Preparation of other bicyclic 4,5-fused-3,6-dihalopyridazines

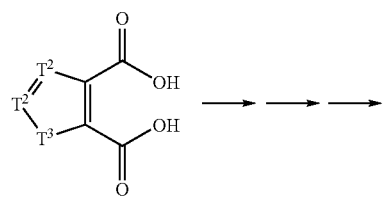

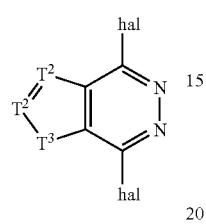

The general procedures of example 9, steps 2 to 4 are used by substituting the appropriate heterocycledicarboxylic acid for furan-2,3-dicarboxylic acid to yield the substituted dichloropyridazines D to G found in the below table. The dibromofuropyridazine G was prepared using steps 2-3 from example 9 and then conducting step 4' as follows: to 0.50 g (3.287 mmol) of the product of step 3 was added 2.83 g (6.57 mmol) of phosphorus pentabromide. This was heated to 125° C. At about 115° C. the reaction mixture melted and then re-solidified before it reached 125° C. The reaction mixture was cooled and the solid residue was crushed up and dumped into ice water. The resulting solid was then filtered and vacuum dried. wt.=0.75 g (82% yield). In several cases the dichloropyridazines are known materials, as indicated by the given reference. All of these dihaloheterocycles can be used to prepare the claimed invention compounds.

TABLE

| | | |
|---|---|---|
| D | Cl-thiazolo-Cl | Was prepared according to methods of: Robba, M.; Bull. Soc. Chim. Fr.; 263, 1966, 1385-1387 1H NMR (DMSO-d6) 9.94 (s, 1); ES MS (M + H)+ = 207 |
| E | Cl-imidazolo-Cl | Was prepared: 1H NMR (DMSO-d6) 8.85 (s, 1); ES MS(M + 1)+ = 189 |
| F | Cl-thieno-Cl | Can be prepared using the methods of: Robba, M., et. al; Bull. Soc. Chim. Fr.; 1967, 4220-4235 |
| G | Br-furo-Br | TLC R$_f$ 0.76 (5% MEOH/methylene chloride) |

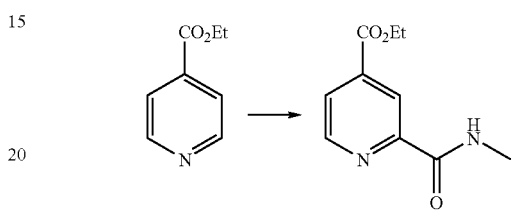

Intermediate H: Preparation of (2-methylaminocarbonyl-4-pyridyl)methanol

Step 1: A stirred solution of ethyl isonicotinate (250 mL, 1.64 mole) and concentrated sulfuric acid (92 mL, 1.64 mole) in N-methylformamide (2.0 L) was cooled to 6° C. with an ice bath. Iron (II) sulfate heptahydrate (22.8 g, 0.0812 mole, milled with a mortar and pestle) was added, followed by the dropwise addition of 30% aqueous hydrogen peroxide (56 mL, 0.492 mole). The additions of iron (II) sulfate and hydrogen peroxide were repeated four additional times, while the reaction temperature was kept below 22° C. After the reaction mixture was stirred for thirty minutes, sodium citrate solution (2 L, 1 M) was added (pH of the resulting mixture was about 5). The mixture was extracted with dichloromethane (1 L, 2×500 mL). The combined organic extracts were washed with water (2×500 mL), 5% aqueous sodium bicarbonate (3×100 mL), and brine (500 mL). The resulting organic solution was then dried over sodium sulfate, filtered and concentrated in vacuo to afford a solid. The crude solid was triturated with hexanes, filtered, washed with hexanes and dried under vacuum to give 270.35 g (79.2%) of pastel yellow solid. $^1$H NMR (DMSO-d$_6$, 300 MHz): δ 8.9 (d, 1H), 8.3 (m, 1H), 8.0 (dd, 1H), 4.4 (q, 2H), 2.8 (d, 3H), 1.3 (t, 3H).

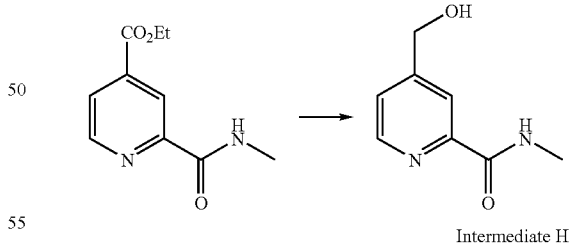

Intermediate H

Step 2: To a mechanically stirred slurry of the product of step 1 (51.60 g, 0.248 mole) in EtOH (1.3 L) was added sodium borohydride (18.7 g, 0.495 mole). The reaction mixture was stirred at rt for 18 hr. The resulting solution was quenched carefully with saturated aqueous ammonium hydrochloride (2 L). Gas evolution was observed during quenching. The resulting mixture was basified with conc. ammonium hydroxide solution (200 ml) to pH=9. It was then extracted with EtOAc (8×400 mL). The combined organic layers were dried (MgSO$_4$), filtered, and concentrated in vacuo to give Intermediate H as a clear light yellow oil (36.6 g, 89% yield). $^1$H NMR (DMSO-$d_6$, 300 MHz): δ 8.74 (q, 1H), 8.53 (dd, 1H), 7.99 (m, 1H), 7.48 (m, 1H), 5.53 (t, 1H), 4.60 (d, 2H), 2.81 (d, 3H); MS m/z 167 [M+H]$^+$.

Intermediates I to N: General Method for Preparation of [2-(N-Substituted)aminocarbonyl-4-pyridyl]methanol Intermediates

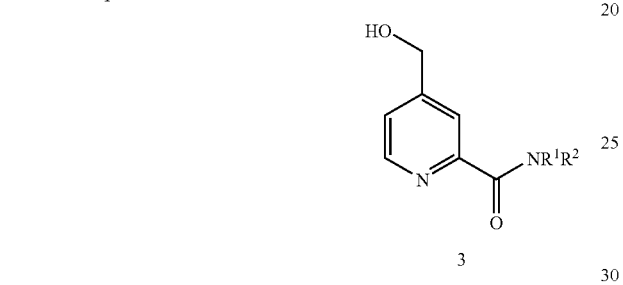

To a 0° C. solution of the amine 2 (3 equiv) in benzene is added trimethyl aluminum (3 equiv). Gas evolution is observed and the reaction is then allowed to warm to rt and stir for 1 h. (Lipton, M. F. et al. *Org. Synth. Coll. Vol.* 6, 1988, 492 or Levin, J. I. et al. *Synth. Comm.*, 1982, 12, 989). The known carbinol 1 (1 equiv, Hadri, A. E.; Leclerc, G. *Heterocyclic Chem*, 1993, 30, 631) is added to the aluminum reagent and the mixture is heated to reflux for 1 h. The reaction is quenched with water and concentrated. The crude product is usually purified by silica gel column chromatography (20/1 EtOAc/MeOH) to afford title compound 3. The final products are generally confirmed by LC/MS and NMR spectroscopy.

| Example | Amine 2 Used | Characterization of Compound 3 |
|---|---|---|
| I | H—N(morpholine) | (M + H)$^{30}$ 223<br>$R_f$ = 0.17 (100% EtOAc) |
| J | H—N(CH$_3$)$_2$ | (M + H)$^{30}$ 181<br>$R_f$ = 0.2 (9:1 EtOAc/MeOH) |
| K | H—NH—CH$_2$CH$_2$—N(CH$_3$)$_2$ | (M + H)$^{30}$ 224 *<br>$R_f$ = 0.14 (1:1 EtOAc/CH$_2$Cl$_2$) |
| L | H—NH—cyclopropyl | (M + H)$^{30}$ 193<br>$R_f$ = (0.58 100% EtOAc) |
| M | H—NH—CH$_2$CH$_2$—OTBS | (M + H)$^{30}$ 311<br>$R_f$ = 0.34 (3/2 EtOAc/Hex) |
| N | H—NH—CH$_2$CH$_3$ | (M + H)$^{30}$ 181<br>$R_f$ = 0.46 (100% EtOAc) |

* CH$_2$Cl$_2$ is used as the solvent rather than benzene.

Example 10

Preparation of 4-(4-chlorophelamino)-7-(2-aminocarbonyl-4-pyridylmethoxy)thieno-[2,3-d]pyridazine

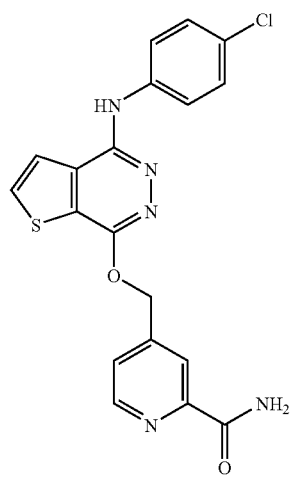

A 25 mL, 3-necked, round-bottomed flask was equipped with a stir bar and thermometer. To the flask was added the product of Example 8 (0.475 g, 1.29 mmol), iron sulfate heptahydrate (0.179 g, 0.64 mmol), formamide (11.15 mL, 281 mmol) and conc. H$_2$SO$_4$ (0.14 mL). The mixture was stirred for 30 min at rt at which time H$_2$O$_2$ (0.2 mL, 6.44 mmol) was added drop wise to the mixture. The reaction stirred at room temperature for an additional hour and then heated to 55° C. over 30 min. The reaction was kept at this temperature for 3 h and then cooled to rt. An aqueous solution of sodium citrate (0.27M, 1 mL) was added to the reaction and subsequently the layers were separated and the aqueous layer was extracted with EtOAc (4×5 mL). The organic layers were combined, dried (MgSO$_4$) and concentrated by rotary evaporation. The resulting solid was taken up in hot acetone and separated from any remaining solids by filtration. The filtrate was then concentrated by rotary evaporation and the resulting residue was taken up in hot MeOH and the white solid was collected by filtration. Desired compound (0.014 g, 0.034 mmol; 2.7% yield); mp=233° C.; ES MS (M+H)+=412; TLC (dichloromethane-methanol-acetone, 95:2.5:2.5); $R_f$=0.20.

Example 11

Preparation of 4-(4-chlorophenylamino)-7-(2-methylaminocarbonyl-4-pyridylmethoxy)thieno-[2,3-d]pyridazine

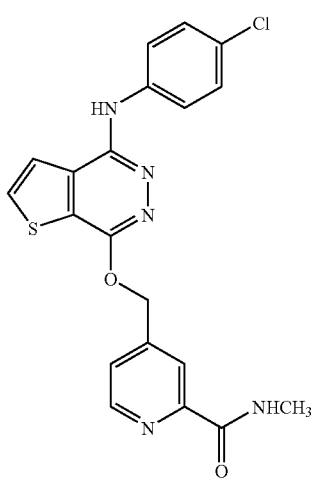

The procedure used for the preparation of Example 10 was used to prepare the title compound by substituting methylformamide for formamide: $^1$H NMR (DMSO-d6) 8.80 (d, 1), 8.62 (d, 1), 8.31 (d, 1), 8.09 (d, 2), 7.86 (d, 2), 7.65 (d, 1), 7.35 (d, 2), 5.74 (s, 2), 2.84 (d, 3); ES MS (M+H)+=426 (ES); $R_f$ (95/2.5/2.5 DCM/MeOH/Acetone)=0.469.

Example 12

Preparation of 1-(4-chlorophenylamino)-4-(2-aminocarbonyl-4-pyridylmethyl)isoquinoline

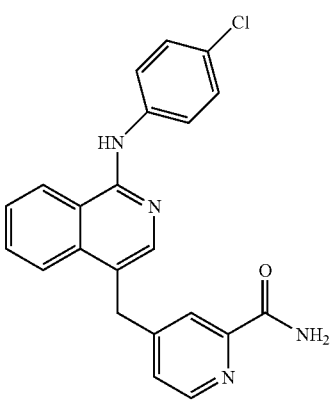

The procedure used for the preparation of Example 10 was used to prepare the title compound by substituting the product of example 4 for the product of example 8. The crude product was purified by preparative TLC plate (1:4 v/v hexane-ethyl acetate, 19% yield) of the title compound as a yellow solid. $^1$H-NMR (MeOH-d$_4$) 8.42 (d, 1H), 8.34 (d, 1H), 7.94 (s, 1H), 7.88 (s, 1H), 7.55 to 7.76 (m, 5H), 7.26 to 7.36 (m, 3H), 4.34 (s, 2H); MS ES 389 (M+H)+; TLC (1:4 v/v hexane-ethyl acetate) $R_f$=0.44.

Example 13

Preparation of 1-(4-chlorophenylamino)-4-(2-methylaminocarbonyl-4-pyridylmethyl)isoquinoline

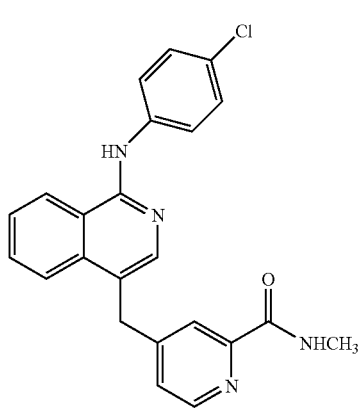

The procedure used for the preparation of Example 11 was used to prepare the title compound by substituting the product of example 4 for the product of Example 8. The crude product was purified by column chromatography (2:3 v/v hexane-ethyl acetate, 20% yield) of the title compound as a yellow solid. $^1$H-NMR (MeOH-d$_4$) 8.42 (d, 1H), 8.33 (d, 1H), 7.88 (d, 2H), 7.55 to 7.77 (m, 5H), 7.28 to 7.36 (m, 3H), 4.34 (s, 2H), 2.89 (s, 3H); MS ES 403 (M+H)+; TLC (2:3 v/v hexane-ethyl acetate) $R_f$=0.30.

Examples 14 and 15

Preparation of 4-(4-chlorophenylamino)-7-(2-methylaminocarbonyl-4-pyridylmethoxy)furo-[2,3-d]pyridazine and 4-(4-chlorophenylamino)-2-methylaminocarbonyl-7-(2-methylaminocarbonyl-4-pyridylmethoxy)furo-[2,3-d]pyridazine

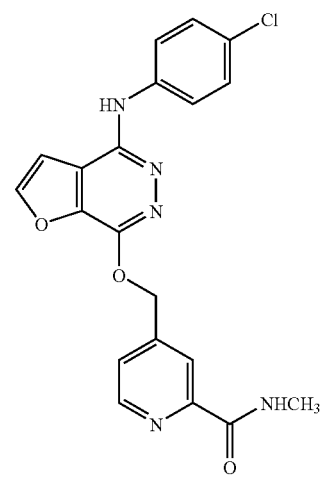

-continued

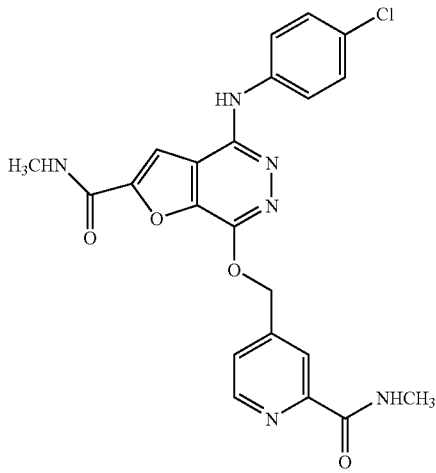

Example 14A

Preparation of 4-(4-chlorophenylamino)-7-(2-methylaminocarbonyl-4-pyridylmethoxy)furo-[2,3-d]pyridazine—Process 2

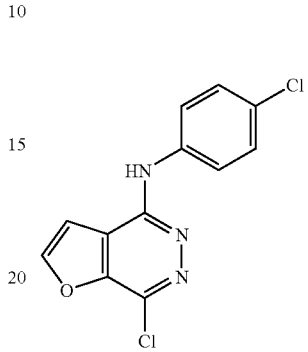 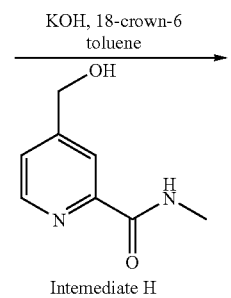

Intermediate H

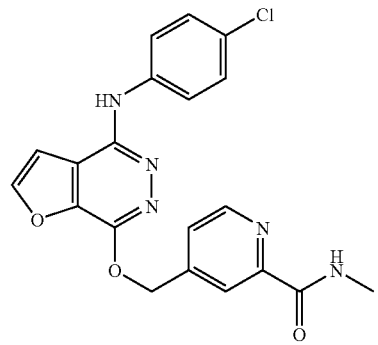

To a suspension of the final product from Example 9 (19.20 g, 54.4 mmol) in N-methylformamide (200 mL) and distilled water (20 mL) at room temperature was added concentrated $H_2SO_4$ (2.9 mL, 54.4 mmol) dropwise. The mixture was stirred until it became a clear solution. To this solution was added $FeSO_4 \cdot 7H_2O$ (1.51 g, 5.43 mmol) in one portion, followed by the addition of hydroxylamine-O-sulfonic acid (HOSA, 1.84 g, 16.3 mmol). The additions of $FeSO_4 \cdot 7H_2O$ and HOSA were repeated in 10 min. intervals for 11 times. HPLC assay showed the consumption of most starting material. The reaction mixture was cooled with an ice bath. A solution of sodium citrate (600 mL, 1M, 600 mmol) was added under vigorous stirring. The resulting suspension was stirred vigorously for additional 10 min. The solid was collected by filtration, washed with water (3×100 mL), and dried under vacuum at 50° C. for 16 hours. The crude product (21 g) was purified by filtering through a silica gel pad eluting with 5% $CH_3OH/CH_2Cl_2$. The resulting 3.7 g product was recrystallized in $CH_3CN$ (125 mL, boiled for 1.5 hours). The solid was collected by filtration, washed with $CH_3CN$ (2×15 mL), and dried under vacuum at 50° C. for 16 hours. The final product (4-(4-chlorophenylamino)-7-(2-methylaminocarbonyl-4-pyridylmethoxy)furo-[2,3-d]pyridazine) is a light yellow solid (3.38 g, 15.2%). mp=223-224° C.

A major byproduct was isolated through the above silica gel pad filtration. The structure of the byproduct (4-(4-chlorophenylamino)-2-methylaminocarbonyl-7-(2-methylaminocarbonyl-4-pyridylmethoxy)furo-[2,3-d]pyridazine) was characterized by $^1H$ NMR, 2D NMR, elemental analysis, and MS. $^1H$ NMR (DMSO-$d_6$, 300 MHz): δ 9.32 (br s, 1H), 8.93 (q, 1H), 8.79 (q, 1H), 8.63 (dd, 1H), 8.12 (m, 1H), 7.91 (m, 3H), 7.70 (dd, 1H), 7.35 (m, 2H), 5.76 (br s, 2H), 2.81 (d, 6H). MS m/z 467 [M+H]$^+$.

To a mixture of the Intermediate from Example 9, step 5 (10.0 g, 35.7 mmol), Intermediate H (12.4 g, 74.6 mmol), and 18-crown-6 (0.42 g, 1.59 mmol) in toluene (100 mL) was added KOH powder (4.4 g, 85%, 66.7 mmol) in one portion at room temperature. The reaction mixture was then heated to 85±2° C. under vigorous stirring. The reaction mixture was stirred vigorously at this temperature overnight. After it was cooled to room temperature, toluene solution was decanted off and water (100 mL) was added to the gummy residue. The resulting mixture was stirred vigorously until it became a free flowing suspension. The solids were collected by filtration, washed with water (2×10 mL), and dried under vacuum at 45° C. for 16 hours. The yellow/brown solids were suspended in acetonitrile (70 mL) and the suspension was stirred at reflux for 2 hours. After it was cooled to room temperature, the solids were collected by filtration, washed with small amount of acetonitrile, and dried under vacuum at 45° C. overnight. The title product was isolated in 46% yield (6.73 g) as a light yellow solid.

Example 16

Preparation of 4-(4-chlorophenylamino)-7-(2-aminocarbonyl-4-pyridylmethoxy)furo-[2,3-d]pyridazine

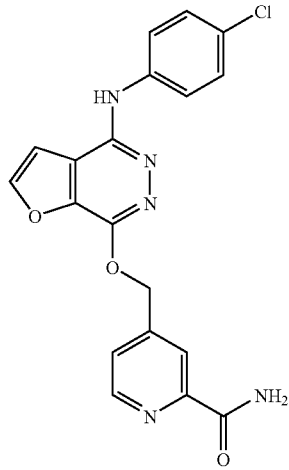

The procedure used for the preparation of Example 14 was used to prepare the title compound by substituting Formamide for N-methylformamide. The reaction was conducted with 500 mg of final product from Example 9 and proportional amounts of solvents and reagents. The crude product was purified by HPLC on a 75×30 mm C18 column and a linear gradient elution from 10 to 100% acetonitrile in water with 0.1% trifluoroacetic acid at 10 ml/min. over 10 min. to yield 18 mg of the title compound as a yellow solid: HPLC (50×4.6 mm YMC CombiScreen® C18 column, linear gradient 10 to 100% acetonitrile in water with 0.1% trifluoroacetic acid at 3 ml/min. over 5 min., UV detection at 254 nm) 2.35 min. peak; MS ES 396 (M+H)$^+$.

Example 17

Preparation of 4-(4-chlorophenylamino)-7-(benzothiazol-6-ylamino)thieno[2,3-d]pyridazine

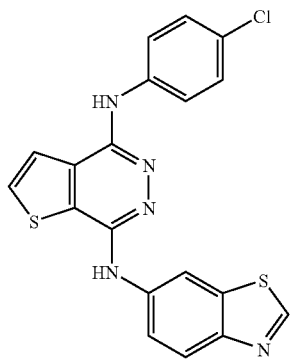

To the dichloride from Example 8, step 4 (1.00 g, 4.90 mmol) was added p-chloroaniline (622 mg, 4.90 mmol) and absolute ethyl alcohol (10.0 mL). The mixture was refluxed at 95° C. for 2 hrs and then cooled to room temperature. The yellow precipitate (2) that formed was filtered and washed with isopropyl alcohol, 4.0 N KOH, H$_2$O, and then hexane. The filtrate (2) was then mixed 6-aminobenzothiazole (883 mg, 5.88 mmol) in 10 mL of n-butanol, and heated at 150° C. overnight. The reaction was allowed to cool to room temperature before the solvent was removed by rotary evaporation. The residue was treated sequentially with aqueous 4.0 N KOH solution and extracted with dichloromethane (50 mL), dried (MgSO$_4$), and the solvent evaporated. The crude product was purified by flash chromatography on silica gel using 95% dichloromethane/methanol as the eluent. The structure of the pure title compound was confirmed by LC/MS and NMR: TLC (30% EtOAc/Hexanes) R$_f$ (3)=0.20; $^1$H NMR (DMSO) δ 7.2 (dd, 3H), 7.38 (dd, 3H), 7.65 (d, 1H), 8.0 (d, 1H), 8.45 (d, 1H), 8.8 (s, 1H); LC/MS m/z 410 rt=4.21 min.

Example 18

Preparation of 4-(indan-5-ylamino)-7-(benzothiazol-6-ylamino)thieno-[2,3-d]pyridazine

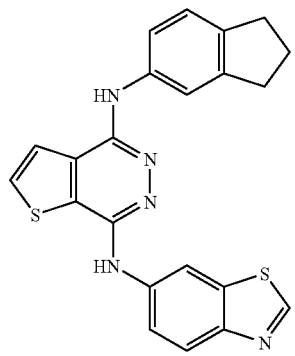

The procedure used for the preparation of Example 17 was used to prepare the title compound by substituting 5-aminoindane for 4-chloroaniline. The crude product was purified by flash chromatography on silica gel using 30% ethyl acetate/hexane as the eluent. The structure of the pure title compound was confirmed by LC/MS and NMR: TLC (30% EtOAc/Hexanes) R$_f$ (3)=0.20; (3) $^1$H NMR (DMSO) δ 2.0 (m, 2H), 2.85 (m, 4H), 7.18 (d, 1H), 7.8 (d, 1H), 7.95 (d, 1H), 8.10 (d, 1H), 8.18 (d, 1H), 8.7 (d, 2H), 9.1 (d, 2H), LC/MS m/z 414 rt=4.43 min.

Example 19

Preparation of 4-(5-bromoindolin-1-yl)-7-(4-pyridylmethoxy)furo[2,3-d]pyridazine

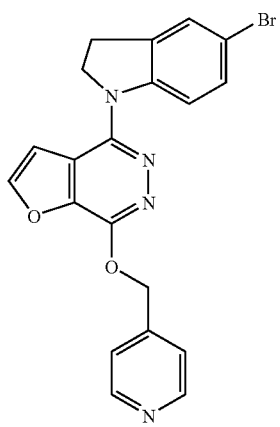

4,7-Dichloro[2,3-d]furopyridazine from step 4 of Example 9 (95 mg, 0.50 mmol) and 5-bromoindoline (100 mg, 0.50 mmol) were refluxed in 60 mL of absolute ethanol at 95° C. for 2 hrs. The reaction mixture was allowed to cool to room temperature and the precipitate that formed was filtered and washed with isopropyl alcohol, 4.0 N KOH, H$_2$O, and hexane, and then dried. The intermediate of about 95% purity (rt=4.72, (M+H)$^+$350) and was used in the next step without further purification. 4-Pyridylcarbinol (28 mg, 0.26 mmol) and sodium hydride (60%, 50 mg, 1.25 mmol) were stirred in 20 mL of anhydrous tetrahydrofuran at 0° C. under Argon for 20 min. and then 44 mg of the above intermediate (0.13 mmol) was added. The reaction was stirred at 0° C. for 2 hrs and the temperature was allowed to rise to room temperature. The mixture was stirred for another 12 hrs and the solvent was evaporated under reduced pressure. The solid that was obtained was dissolved in 50 mL of dichloromethane and washed with K$_2$CO$_3$ solution and H$_2$O. The organic layer was separated, dried (MgSO$_4$), and evaporated under reduced pressure. The crude product was purified by preparative TLC (R$_f$=0.3) on silica gel using dichloromethane/methanol (95:5) as the eluent. The structure of the pure title compound was confirmed by LC/MS and NMR: $^1$H NMR (CDCl$_3$) δ 3.20 (m, 2H), 4.30~4.50 (m, 2H), 5.60 (s, 2H), 6.9~8.0 (m, 7H), 8.60 (m, 2H); LC/MS (M+H)+423 rt=4.49 min.

Example 20

Preparation of 4-(4-methoxyphenylamino)-7-(2-methylaminocarbonyl-4-pyridylmethoxy)furo-[2,3-d]pyridazine

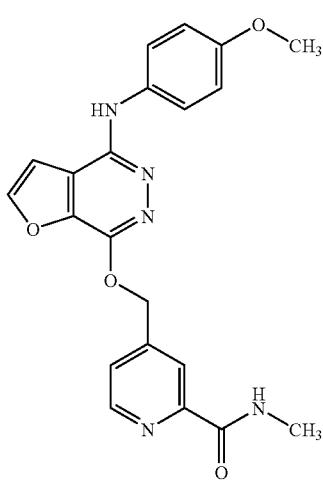

To a suspension of 4,7-Dichloro[2,3-d]furopyridazine from step 4 of Example 9 (400 mg, 2.12 mmol, 1 equiv) and p-anisidine (p-MeOC$_6$H$_4$NH$_2$) (260 mg, 2.12 mmol, 1 equiv) in DME (5 mL) was added water (1 mL). The resulting solution was heated at 50° C. for 48 h. After cooling to rt, the brown precipitate was removed by filtration and the filtrate was concentrated in vacuo to afford the crude product as a brown solid. Trituration of the brown solid with CH$_2$Cl$_2$ furnished 292 mg (50%) of the intermediate 4-(4-methoxyphenylamino)-7-chlorofuro-[2,3-d]pyridazine which was confirmed by LC/MS and NMR. A suspension of this intermediate (292 mg, 1.06 mmol, 1 equiv), (2-methylaminocarbonyl-4-pyridyl)methanol (Intermediate H, 529 mg, 3.18 mmol, 3 equiv) and 18-crown-6 (42 mg, 0.16 mmol, 15 mol %) in toluene (4 mL) was stirred at rt for 20 min. KOH (178 mg, 3.18 mmol, 3 equiv) was then added and the reaction mixture was heated to 80° C. for 36 h. After cooling to rt, water (10 mL) was added and the mixture was stirred vigorously until a fine white suspension was formed. The suspension was filtered and washed with water and diethyl ether to provide 125 mg (29%) of the desired product as a light yellow solid: (M+H)$^+$406; R$_f$=0.50 (100% EtOAc).

Example 21

Preparation of 4-(4-methoxyphenylamino)-7-(4-pyridylmethoxy)furo-[2,3-d]pyridazine

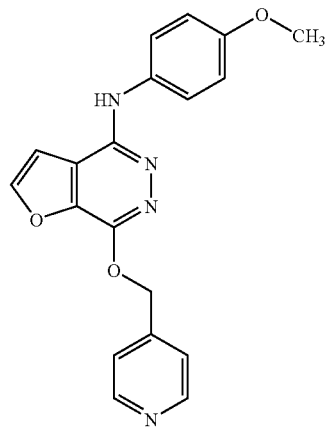

The procedure used for the preparation of Example 20 was used to prepare the title compound by substituting 4-pyridylmethanol for (2-methylaminocarbonyl-4-pyridyl)methanol. The pure product was isolated by chromatography on a flash column: (M+H)$^+$349; R$_f$=0.3 (95:5 CH$_2$Cl$_2$/CH$_3$OH).

Example 22

Preparation of 4-(4-methoxyphenylamino)-7-(2-aminocarbonyl-4-pyridylmethoxy)furo-[2,3-d]pyridazine

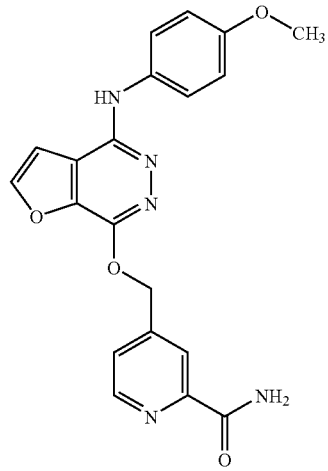

The procedure used for the preparation of Example 16 was used to prepare the title compound by substituting the product of Example 21 for the product from Example 9. The reaction was conducted with 250 mg of the starting material and proportional amounts of solvents and reagents. The crude product was purified by HPLC on a 75×30 mm C18 column and a linear gradient elution from 10 to 100% acetonitrile in water with 0.1% trifluoroacetic acid at 10 ml/min. over 10 min. to yield 16 mg of the title compound as a yellow solid: HPLC (50×4.6 mm YMC CombiScreen® C18 column, linear gradient 10 to 100% acetonitrile in water with 0.1% trifluoroacetic acid at 3 ml/min. over 5 min., UV detection at 254 nm) 1.98 min. peak; MS ES 392 (M+H)+.

Examples 23-80

Preparation of Invention Compounds by Methods A-1, A-2 and A-3

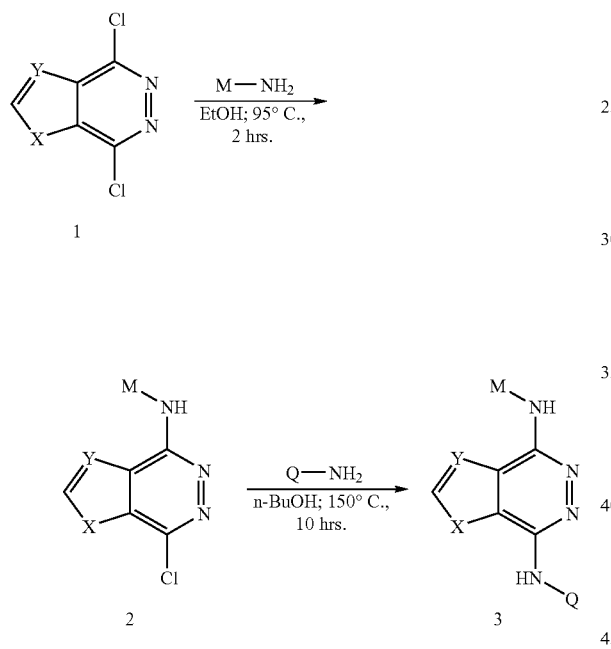

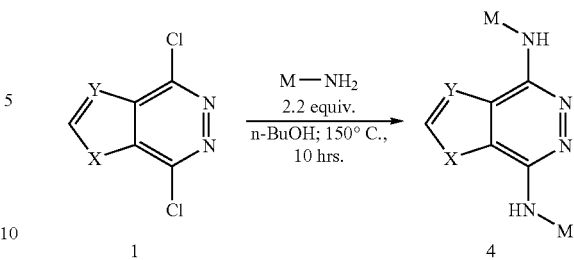

Method A-2: One equivalent of dichloride (1) and 2.2 equivalent of M-NH$_2$ are refluxed in an appropriate amount of n-butanol at 150° C. for 10 hrs. The reaction mixture is allowed to cool to room temperature and the precipitate (4) that forms is filtered and washed sequentially with isopropyl alcohol, 4.0 N KOH, H$_2$O, and hexane, and then dried. The crude product (4) is purified by preparative TLC or flash chromatography on silica gel using dichloromethane/methanol (95:5) as the eluent. Final product is confirmed by LC/MS and/or NMR. The invention compounds of Examples 26-33 and 75 as shown in the below table were prepared by method A-2.

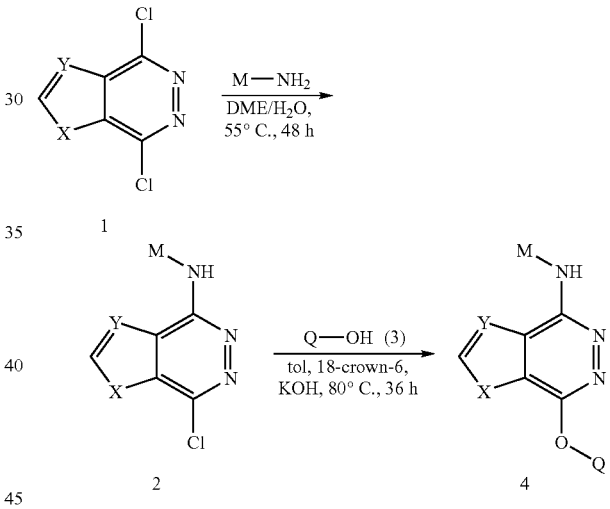

Method A-1: Equal equivalents of dichloride (1) and M-NH$_2$ are refluxed in the appropriate amount of absolute ethanol at 95° C. for 2 hrs. The reaction mixture is allowed to cool to room temperature and the precipitate (2) that forms is filtered and washed sequentially with isopropyl alcohol, 4.0 N KOH, H$_2$O, and hexane, and then dried. The filtrate (2) is then reacted with 1.2 equivalent of Q-NH$_2$ in an appropriate amount of n-butyl alcohol at 150° C. for 10 hrs. The reaction is cooled to room temperature before the solvent is evaporated under reduced pressure. The residue is treated with aqueous 4.0 N KOH solution and extracted with dichloromethane. The organic layer is dried (MgSO$_4$) and evaporated. The crude product (3) is purified by preparative thin layer chromatography (TLC) or flash chromatography on silica gel using dichloromethane/methanol (95:5) as the eluent. Final product is confirmed by LC/MS and/or NMR. The invention compounds of Examples 23-25, 48, and 76-80 as shown in the below table were prepared by method A-1.

Method A-3: One equivalent of dichloride (1) and one equivalent of M-NH$_2$ are suspended in DME (0.3M) and water is added until a solution was formed. The reaction mixture is heated to 65° C. for 48 h. After cooling to rt, the resulting precipitate is filtered and washed with DME to provide the intermediate product (2) which is confirmed by LC/MS and NMR. In some instances, intermediate (2) is further purified by preparative TLC or washed with other solvents. A suspension of (2) (1 equiv), carbinol (3) (3 equiv), and 18-crown-6 (10 mol %) in toluene (0.3M) is stirred at rt for 10 min. KOH (3 equiv) is then added and the reaction mixture is heated to 80° C. for 24 h. After cooling to rt, water is added and the mixture is stirred vigorously until a suspension is formed. The suspension is filtered and washed with water to provide the desired product (4). Preparative TLC and/or washing with other solvents is used to further purify final products in some examples. The final products are assigned by LC/MS and NMR spectroscopy. Final product is confirmed by LC/MS and/or NMR. The invention compounds of Examples 34-47, 49-74, and 81-82D as shown in the below table were prepared by method A-3.

Compounds that were Prepared by Parallel Methods A-1, A-2 or A-3

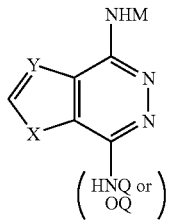

| Ex. # | X | Y | MNH | NHQ or OQ | Method | Characterization* |
|---|---|---|---|---|---|---|
| 23 | S | CH | 4-Cl-phenyl-NH- | benzothiazol-6-yl-NH- | A-1 | m/z = 410<br>rt = 4.21 min.[a] |
| 24 | S | CH | indan-5-yl-NH- | benzothiazol-6-yl-NH- | A-1 | m/z = 414<br>rt = 4.43 min.[a] |
| 25 | O | CH | 5-Br-indolin-1-yl- | pyridin-4-ylmethoxy- | A-1[d] | (M + H)+423<br>rt = 4.49 min.[a] |
| 26 | S | CH | 1H-benzotriazol-5-yl-NH- | 1H-benzotriazol-5-yl-NH- | A-2 | (M + H)+401<br>rt = 2.01 min.[a] |
| 27 | S | CH | 1H-indazol-5-yl-NH- | 1H-indazol-5-yl-NH- | A-2 | (M + H)+399<br>NH<br>rt = 2.27 min.[a] |
| 28 | O | CH | benzothiazol-6-yl-NH- | benzothiazol-6-yl-NH- | A-2 | (M + H)+417<br>rt = 2.47 min.[a] |

-continued

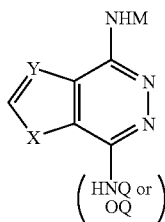

| Ex. # | X | Y | MNH | NHQ or OQ | Method | Characterization* |
|---|---|---|---|---|---|---|
| 29 | O | CH | 1H-benzotriazol-5-yl-NH | 1H-benzotriazol-5-yl-NH | A-2 | (M + H)⁺385<br>rt = 1.75 min.ᵃ |
| 30 | O | CH | 1H-indazol-5-yl-NH | 1H-indazol-5-yl-NH | A-2 | (M + H)⁺383<br>rt = 1.83 min.ᵃ |
| 31 | N | N | 1H-benzotriazol-5-yl-NH | 1H-benzotriazol-5-yl-NH | A-2 | (M + H)⁺385<br>rt = 1.62 min.ᵃ |
| 32 | N | N | 1H-indazol-5-yl-NH | 1H-indazol-5-yl-NH | A-2 | (M + H)⁺383<br>rt = 1.88 min.ᵃ |
| 33 | N | N | benzothiazol-6-yl-NH | benzothiazol-6-yl-NH | A-2 | (M + H)⁺417<br>rt = 2.47 min.ᵃ |
| 34 | O | CH | 4-methoxyphenyl-NH | CH₂O-pyridazine-C(O)NHCH₃ | A-3 | (M + H)⁺406<br>R_f = 0.50 (100% EtOAc) |

-continued

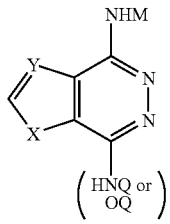

| Ex. # | X | Y | MNH | NHQ or OQ | Method | Characterization* |
|---|---|---|---|---|---|---|
| 35 | O | CH | 3-Cl-phenyl-NH | 4-(CH2O-)pyridine-2-C(O)NHCH3 | A-3 | (M + H)+410<br>Rf = 0.51 (100% EtOAc) |
| 36 | O | CH | 4-F-3-Cl-phenyl-NH | 4-(CH2O-)pyridine-2-C(O)NHCH3 | A-3 | (M + H)+428<br>Rf = 0.55 (100% EtOAc) |
| 37 | O | CH | 4-F-phenyl-NH | 4-(CH2O-)pyridine-2-C(O)NHCH3 | A-3 | (M + H)+394<br>Rf = 0.57 (100% EtOAc) |
| 38 | O | CH | 4-Br-phenyl-NH | 4-(CH2O-)pyridine-2-C(O)NHCH3 | A-3 | (M + H)+455<br>Rf = 0.56 (100% EtOAc) |
| 39 | O | CH | 4-CH3-phenyl-NH | 4-(CH2O-)pyridine-2-C(O)NHCH3 | A-3 | (M + H)+390<br>Rf = 0.53 (100% EtOAc) |
| 40 | O | CH | 3-CH3-phenyl-NH | 4-(CH2O-)pyridine-2-C(O)NHCH3 | A-3 | (M + H)+390<br>Rf = 0.68 (100% EtOAc) |

-continued

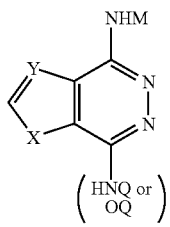

| Ex. # | X | Y | MNH | NHQ or OQ | Method | Characterization* |
|---|---|---|---|---|---|---|
| 41 | O | CH | 4-(dimethylamino)phenyl-NH- | pyridine-2-carboxamide-CH₂O- | A-3 | (M + H)⁺419<br>$R_f$ = 0.12 (3:2 CH₂Cl₂/EtOAc) |
| 42 | O | CH | 4-(trifluoromethyl)phenyl-NH- | pyridine-2-carboxamide-CH₂O- | A-3 | (M + H)⁺444<br>$R_f$ = 0.60 (100% EtOAc) |
| 43 | O | CH | 4-(trifluoromethoxy)phenyl-NH- | pyridine-2-carboxamide-CH₂O- | A-3 | (M + H)⁺460<br>$R_f$ = 0.57 (100% EtOAc) |
| 44 | O | CH | 3-chloro-4-methoxyphenyl-NH- | pyridine-2-carboxamide-CH₂O- | A-3 | (M + H)⁺440<br>$R_f$ = 0.43 (100% EtOAc) |
| 45 | O | CH | 4-(N-methylacetamido)phenyl-NH- | pyridine-2-carboxamide-CH₂O- | A-3 | (M + H)⁺447<br>$R_f$ = 0.07 (100% EtOAc) |
| 46 | O | CH | 4-morpholinophenyl-NH- | pyridine-2-carboxamide-CH₂O- | A-3 | (M + H)⁺461<br>$R_f$ = 0.38 (100% EtOAc) |

-continued

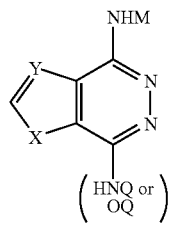

| Ex. # | X | Y | MNH | NHQ or OQ | Method | Characterization* |
|---|---|---|---|---|---|---|
| 47 | O | CH | 3,4-difluorophenyl-NH- | 4-(methylcarbamoyl)pyridin-2-yl-CH2-O- | A-3 | (M + H)+412<br>Rf = 0.43 (100% EtOAc) |
| 48 | O | CH | 4-chlorophenyl-NH- | benzothiazol-6-yl-NH- | A-1 | (M + H)+394<br>Rf = 0.37 (100% EtOAc) |
| 49 | O | CH | indan-5-yl-NH- | 4-(methylcarbamoyl)pyridin-2-yl-CH2-O- | A-3 | (M + H)+416<br>Rf = 0.64 (100% EtOAc) |
| 50 | O | CH | 2-methoxyphenyl-NH- | 4-(methylcarbamoyl)pyridin-2-yl-CH2-O- | A-3 | (M + H)+406<br>Rf = 0.55 (100% EtOAc) |
| 51 | O | CH | 3-methoxyphenyl-NH- | 4-(methylcarbamoyl)pyridin-2-yl-CH2-O- | A-3 | (M + H)+406<br>Rf = 0.52 (100% EtOAc). |
| 52 | O | CH | benzo[1,3]dioxol-5-yl-NH- | 4-(methylcarbamoyl)pyridin-2-yl-CH2-O- | A-3 | (M + H)+420<br>Rf = 0.37(4:1 EtOAc/ |

-continued

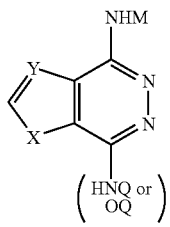

| Ex. # | X | Y | MNH | NHQ or OQ | Method | Characterization* |
|---|---|---|---|---|---|---|
| 53 | O | CH | 3,4-dichlorophenyl-NH- | 4-(methylcarbamoyl)pyridin-2-yl)methoxy | A-3 | (M + H)+444<br>Rf = 0.47 (100% EtOAc). |
| 54 | O | CH | 3,5-dimethylphenyl-NH- | 4-(methylcarbamoyl)pyridin-2-yl)methoxy | A-3 | (M + H)+404<br>Rf = 0.49 (100% EtOAc). |
| 55 | O | CH | 1H-indazol-5-yl-NH- | 4-(methylcarbamoyl)pyridin-2-yl)methoxy | A-3 | (M + H)+416<br>Rf = 0.23 (100% EtOAc). |
| 14 | O | CH | 4-chlorophenyl-NH- | 4-(methylcarbamoyl)pyridin-2-yl)methoxy | A-3 | (M + H)+410<br>rt = 2.38 min. |
| 56 | O | CH | 4-methoxyphenyl-NH- | pyridin-4-ylmethoxy | A-3 | (M + H)+349<br>Rf = 0.3 (95:5 CH2Cl2/CH3OH) |
| 57 | O | CH | 4-hydroxyphenyl-NH- | 4-(methylcarbamoyl)pyridin-2-yl)methoxy | A-3 | (M + H)+392<br>Rf = 0.43 (4:1 EtOAc/CH2Cl2) |

-continued

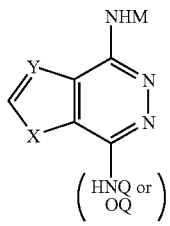

| Ex. # | X | Y | MNH | NHQ or OQ | Method | Characterization* |
|---|---|---|---|---|---|---|
| 58 | O | CH | HO-C6H4-NH- | 4-pyridylmethyloxy | A-3 | (M + H)+335<br>R_f = 0.37 (4/1 EtOAc/CH2Cl2) |
| 59 | O | CH | phenyl-NH- | 4-(N-methylcarbamoyl)pyridin-2-ylmethyloxy | A-3 | (M + H)+376<br>R_f = 0.32 (4/1 EtOAc/Hex) |
| 60 | O | CH | 3-methoxy-4-methylphenyl-NH- | 4-(N-methylcarbamoyl)pyridin-2-ylmethyloxy | A-3 | (M + H)+420<br>R_f = 0.43 (100% EtOAc). |
| 61 | O | CH | 4-chlorophenyl-NH- | 4-(morpholinocarbonyl)pyridin-2-ylmethyloxy | A-3 | (M + H)+466<br>R_f = 0.25 (100% EtOAc). |
| 62 | O | CH | 2-methylbenzothiazol-5-yl-NH- | 4-(N-methylcarbamoyl)pyridin-2-ylmethyloxy | A-3 | (M + H)+447<br>R_f = 0.11 (4:1 EtOAc/Hex) |
| 63[c] | O | CH | benzothiazol-6-yl-NH- | 4-(N-methylcarbamoyl)pyridin-2-ylmethyloxy | A-3 | (M + H)+435<br>R_f = 0.35 (100% EtOAc) |

-continued

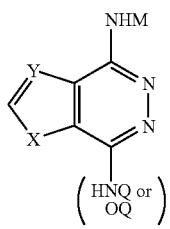

| Ex. # | X | Y | MNH | NHQ or OQ | Method | Characterization* |
|---|---|---|---|---|---|---|
| 64 | O | CH | 4-Cl-phenyl-NH- | 4-(hydroxymethyl)pyridin-2-yl-CH2-O- | A-3 | (M + H)+383 rt = 1.77 min.[b] |
| 65 | O | CH | 2,3-dihydrobenzofuran-5-yl-NH- | 4-(N-methylcarbamoyl)pyridin-2-yl-CH2-O- | A-3[e] | (M + H)+418 Rf = 0.50 (100% EtOAc) |
| 66 | S | CH | 2,3-dihydrobenzofuran-5-yl-NH- | 4-(N-methylcarbamoyl)pyridin-2-yl-CH2-O- | A-3[e] | (M + H)+434 Rf = 0.50 (100% EtOAc) |
| 67 | S | CH | 4-F-phenyl-NH- | 4-(N-methylcarbamoyl)pyridin-2-yl-CH2-O- | A-3 | (M + H)+410 rt = 2.04 min.[b] |
| 68 | S | CH | 3-methyl-phenyl-NH- | 4-(N-methylcarbamoyl)pyridin-2-yl-CH2-O- | A-3 | (M + H)+406 rt = 2.36 min.[b] |
| 69 | S | CH | 4-methoxy-phenyl-NH- | 4-(N-methylcarbamoyl)pyridin-2-yl-CH2-O- | A-3 | (M + H)+422 rt = 2.31 min.[b] |

-continued

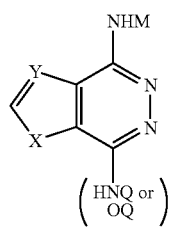

| Ex. # | X | Y | MNH | NHQ or OQ | Method | Characterization* |
|---|---|---|---|---|---|---|
| 70 | S | CH | 4-(F₃CO)-C₆H₄-NH- | 4-(CH₂O-)-pyridine-2-C(O)NHCH₃ | A-3 | (M + H)⁺476 rt = 2.72 min.[b] |
| 71 | S | CH | 4-(F₃C)-C₆H₄-NH- | 4-(CH₂O-)-pyridine-2-C(O)NHCH₃ | A-3 | (M + H)⁺460 rt = 2.39 min.[b] |
| 72 | S | CH | 4-Br-C₆H₄-NH- | 4-(CH₂O-)-pyridine-2-C(O)NHCH₃ | A-3 | (M + H)⁺472 rt = 2.53 min.[b] |
| 73 | S | CH | indan-5-yl-NH- | 4-(CH₂O-)-pyridine-2-C(O)NHCH₃ | A-3 | (M + H)⁺432 rt = 2.63 min.[b] |
| 74 | S | CH | benzo[1,3]dioxol-5-yl-NH- | 4-(CH₂O-)-pyridine-2-C(O)NHCH₃ | A-3 | (M + H)⁺436 rt = 2.26 min.[b] |
| 75 | S | CH | benzothiazol-6-yl-NH- | benzothiazol-6-yl-NH- | A-2 | (M + H)⁺433 rt = 2.61 min.[a] |

-continued
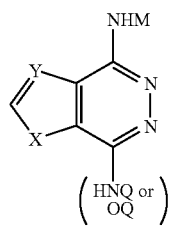
| Ex. # | X | Y | MNH | NHQ or OQ | Method | Characterization* |
|---|---|---|---|---|---|---|
| 76 | S | CH | 4-Br-C6H4-NH- | 6-benzothiazolyl-NH- | A-1 | (M + H)+455 rt = 3.43 min.$^a$ |
| 77 | S | CH | 4-iPr-C6H4-NH- | 6-benzothiazolyl-NH- | A-1 | (M + H)+432 rt = 4.05 min.$^a$ |
| 78 | S | CH | 2,4-diMe-C6H3-NH- | 6-benzothiazolyl-NH- | A-1 | (M + H)+404 rt = 3.08 min.$^a$ |
| 79 | S | CH | 3-F-4-Me-C6H3-NH- | 6-benzothiazolyl-NH- | A-1 | (M + H)+408 rt = 3.07 min.$^a$ |
| 80 | S | CH | 3,4,5-triOMe-C6H2-NH- | 6-benzothiazolyl-NH- | A-1 | (M + H)+466 rt = 2.86 min.$^a$ |

-continued
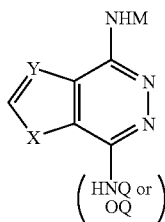
| Ex. # | X | Y | MNH | NHQ or OQ | Method | Characterization* |
|---|---|---|---|---|---|---|
| 81 | O | CH | Cl-C6H4-NH- | 4-(CH2O-)pyridine-2-C(O)N(CH3)2 | A-3 | (M + H)+424<br>Rf = 0.38 (100% EtOAc). |
| 82A | O | CH | Cl-C6H4-NH- | 4-(CH2O-)pyridine-2-C(O)NH-CH2CH2-N(CH3)2 | A-3 | (M + H)+467<br>Rf = 0.19 (1:1 EtOAc/CH3OH). |
| 82B | O | CH | Cl-C6H4-NH- | 4-(CH2O-)pyridine-2-C(O)NH-cyclopropyl | A-3 | (M + H)+436<br>Rf = 0.78 (100% EtOAc) |
| 82C | O | CH | Cl-C6H4-NH- | 4-(CH2O-)pyridine-2-C(O)NH-CH2CH2OH | A-3f | (M + H)+440<br>Rf = 0.35 (100% EtOAc) |
| 82D | O | CH | Cl-C6H4-NH- | 4-(CH2O-)pyridine-2-C(O)NH-CH2CH3 | A-3 | (M + H)+424<br>Rf = 0.70 (100% EtOAc) |

All compounds in this table can be characterized by HPLC—positive ion electrospray mass spectroscopy (HPLC ES-MS, conditions as below). In addition some of the compounds were characterized by TLC on silica gel plates and the $R_f$ values and solvents are shown. HPLC retention times are given for other examples in this table; [a] HPLC—electrospray mass spectra (HPLC ES-MS) were obtained using a Hewlett-Packard 1100 HPLC equipped with a quaternary pump, a variable wavelength detector, a YMC Pro C18 2.0 mm×23 mm column, and a Finnigan LCQ ion trap mass spectrometer with electrospray ionization. Gradient elution from 90% A to 95% B over 4 minutes was used on the HPLC. Buffer A was 98% water, 2% Acetonitrile and 0.02% TFA. Buffer B was 98% Acetonitrile, 2% water and 0.018% TFA. Spectra were scanned from 140-1200 amu using a variable ion time according to the number of ions in the source; [b] An HPLC assay with UV peak detection was run in addition to the HPLC ES-MS experiment and the conditions are: 50×4.6 mm YMC CombiScreen® C18 column, linear gradient 10 to 100% acetonitrile in water with 0.1% trifluoroacetic acid at 3 ml/min. over 5 min., UV detection at 254 nm; [c] The product was purified by RP-HPLC on a C18 column using a water/acetonitrile gradient with added trifluoroacetic acid such that the trifluoroacetate salt was isolated by evaporation of the pure product; [d] 4-pyridylmethanol, as indicated, was used in step 2 of method A-1 rather than an amine; [e] For preparation of 5-amino-2,3-dihydrobenzofurane see Mitchell, H.; Leblanc, Y. *J. Org. Chem.* 1994, 59, 682-687. [f] The reference to make the known TBS protected alcohol intermediate is: Parsons, A. F.; Pettifer, R. M. *J. Chem. Soc. Perkin Trans.* 1, 1998, 651.

The deprotection of

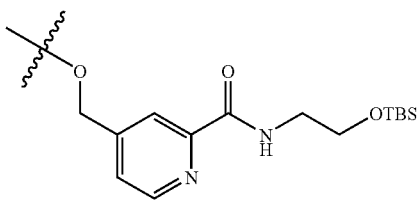

was accomplished in the following manner:

Three equiv of a 1.0 Molar solution of TBAF in THF was added to a solution of the protected alcohol in THF (0.05 Molar) at rt. The reaction mixture was allowed to stir at rt for 1 h and was quenched with water followed by extraction with EtOAc.

Examples 83-92

Preparation of Isoquinolines by Method B-1

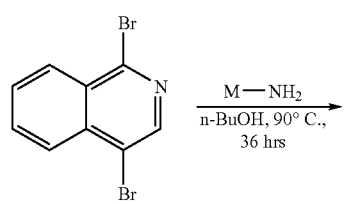

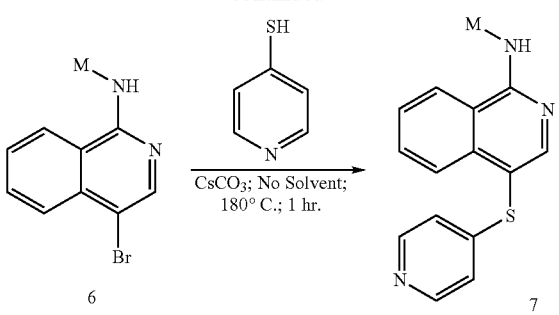

Method B-1: Dibromoisoquinoline (5, 29 mg, 0.1 mmol) Example 1, step 1, and M-NH₂ (0.2 mmol) in 8-mL vial were heated in 1 mL of n-butanol at 90° C. for 36 hrs. The mixture was cooled to room temperature and the solvent was evaporated under reduced pressure. 4-Mercaptopyridine (23 mg, 0.2 mmol) and cesium carbonate (67 mg, 0.2 mmol) were added to the vial. The mixture was heated at 180° C. for 1 hr and was allowed to cool to room temperature. Methanol (2 mL) was added to the vial and the mixture was sonicated for 10 min and filtered. The methanol solution of reaction mixture was collected and evaporated under reduced pressure. The formation of product was confirmed by LC/MS. The invention compounds of Examples 83-92 as shown in the below table were prepared by method B-1.

Compounds that were Prepared by Method B-1

| Example # | MNH | Characterization* |
|---|---|---|
| 83 | ![F3C-phenyl-CH2-NH structure] | $(M + H)^+$ 412<br>rt = 3.46 min. |
| 84 | ![benzodioxole-CH2-NH structure] | $(M + H)^+$ 388<br>rt = 2.89 min. |
| 85 | ![4-Cl-phenyl-NH structure] | $(M + H)^+$ 364<br>rt = 3.41 min. |

| Example # | MNH | Characterization* |
|---|---|---|
| 86 | 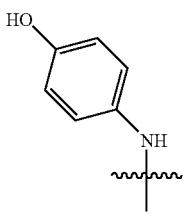 | (M + H)+ 346<br>rt = 1.83 min. |
| 87 | 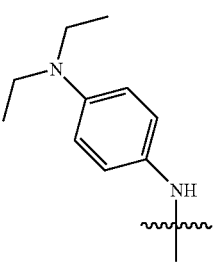 | (M + H)+ 401<br>rt = 2.52 min. |
| 88 | 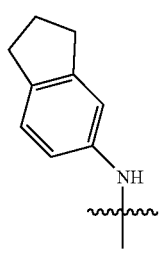 | (M + H)+ 370<br>rt = 3.17 min. |
| 89 | 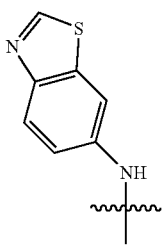 | (M + H)+ 387<br>rt = 3.02 min. |
| 90 | 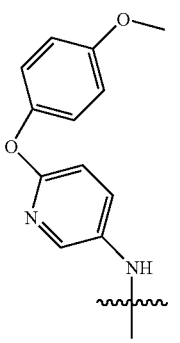 | (M + H)+ 453<br>rt = 3.39 min. |
| 91 | 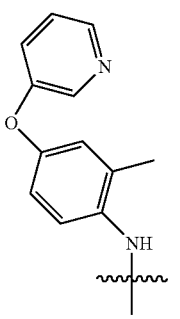 | (M + H)+ 437<br>rt = 3.33 in. |
| 92 | 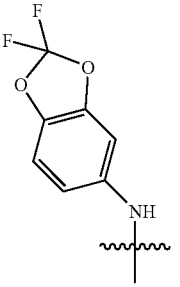 | (M + H)+ 401<br>rt = 2.52 min. |

*HPLC - electrospray mass spectra (HPLC ES-MS) were obtained using a Hewlett-Packard 1100 HPLC equipped with a quaternary pump, a variable wavelength detector, a YMC Pro C18 2.0 mm × 23 mm column, and a Finnigan LCQ ion trap mass spectrometer with electrospray ionization. Gradient elution from 90% A to 95% B over 4 minutes was used on the HPLC. Buffer A was 98% water, 2% Acetonitrile and 0.02% TFA. Buffer B was 98% Acetonitrile, 2% water and 0.018% TFA. Spectra were scanned from 140-1200 amu using a variable ion time according to the number of ions in the source.

Examples 93-105

Preparation of Novel Phthalazine Invention Compounds by Parallel Synthesis

Method A-1 or A-2, as indicated, were used to prepare the novel phthalimide invention compounds 93-105 from 1,4-dichlorophthalazine (for preparation see Novartis patent WO98/35958, Nov. 2, 1998) rather than the dichloroheterocyclopyridazines together with the appropriate bicyclic and substituted anilines.

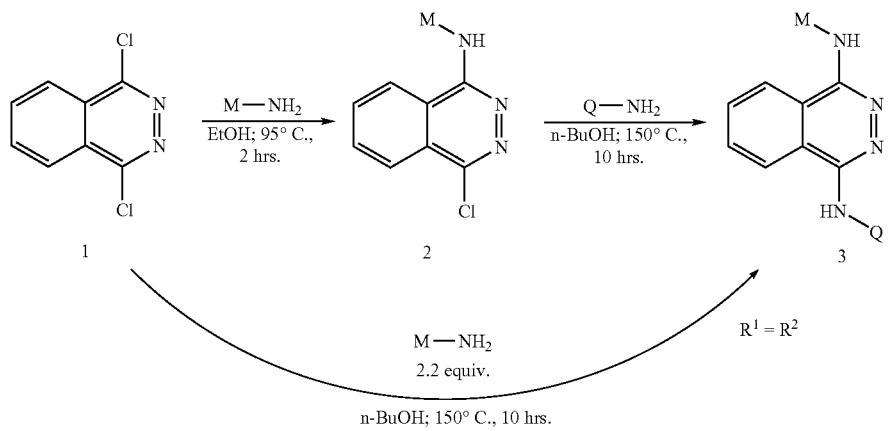
Novel Phthalazines that were Prepared by Methods A-1 or A-2
| Example # | MNH | ONH | Method | Characterization |
|---|---|---|---|---|
| 93 | benzothiazol-6-yl | benzothiazol-6-ylamino | A-2 | (M + H)+ 427<br>rt = 3.13 min. |
| 94 | 1H-benzotriazol-5-yl | 1H-benzotriazol-5-ylamino | A-2 | (M + H)+ 395<br>rt = 2.52 min. |
| 95 | 4-chlorophenyl | benzothiazol-6-ylamino | A-1 | (M + H)+ 387<br>rt = 2.77 min. |

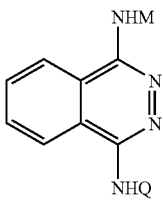
| Example # | MNH | ONH | Method | Characterization |
|---|---|---|---|---|
| 96 | 4-Cl-C6H4-NH- | benzotriazol-5-yl-NH- | A-1 | (M + H)+ 388  rt = 2.51 min. |
| 97 | 5-Br-indolin-1-yl | benzothiazol-6-yl-NH- | A-1 | (M + H)+ 474  rt = 3.67 min. |
| 98 | 2,2-difluoro-benzo[1,3]dioxol-5-yl-NH- | benzothiazol-6-yl-NH- | A-1 | (M + H)+ 450  rt = 3.54 min. |
| 99 | 4-(piperidin-1-yl)phenyl-NH- | benzothiazol-6-yl-NH- | A-1 | (M + H)+ 453  rt = = 2.70 min. |
| 100 | 4-(N-ethyl-N-isopropylamino)phenyl-NH- | benzothiazol-6-yl-NH- | A-1 | (M + H)+ 455  rt = 2.58 min. |

-continued

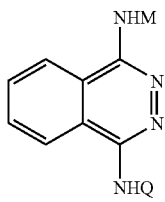

| Example # | MNH | ONH | Method | Characterization |
|---|---|---|---|---|
| 101 | 3-Br-C6H4-NH- | benzothiazol-6-yl-NH- | A-1 | (M + H)+ 448<br>rt = 3.02 min. |
| 102 | 4-iPr-C6H4-NH- | benzothiazol-6-yl-NH- | A-1 | (M + H)+ 412<br>rt = 3.27 min. |
| 103 | 3-MeO-C6H4-NH- | benzothiazol-6-yl-NH- | A-1 | (M + H)+ 400<br>rt = 2.79 min. |
| 104 | 3-F-4-Me-C6H3-NH- | benzothiazol-6-yl-NH- | A-1 | (M + H)+ 402<br>rt = 2.96 min. |
| 105 | 4-Cl-C6H4-NH- | benzothiazol-6-yl-NH- | A-1 | (M + H)+ 404<br>rt = 3.03 min. |

* HPLC - electrospray mass spectra (HPLC ES-MS) were obtained using a Hewlett-Packard 1100 HPLC equipped with a quaternary pump, a variable wavelength detector, a YMC Pro C18 2.0 mm × 23 mm column, and a Finnigan LCQ ion trap mass spectrometer with electrospray ionization. Gradient elution from 90% A to 95% B over 4 minutes was used on the HPLC. Buffer A was 98% water, 2% Acetonitrile and 0.02% TFA. Buffer B was 98% Acetonitrile, 2% water and 0.018% TFA. Spectra were scanned from 140-1200 amu using a variable ion time according to the number of ions in the source.

Examples 106-114

Preparation of Salts of Example 14

The product of Example 14 (1.50 g, 3.66 mmol) was stirred as a slurry in methanol (20 ml) as a solution of toluenesulfonic acid hydrate (0.701 g, 3.67 mmol) in methanol (5 ml plus 5 ml rinse) was added quickly dropwise. All materials dissolved over 5 min to yield a yellow solution. Anhydrous ether (30 ml) was added and stirring was continued for 5 minutes until solid began to precipitate. The resultant mixture was chilled with stirring in an ice/water bath for 45 minutes and then the solid title product (Example 104) was collected by filtration, washed with ether and dried at 55 IC in a vacuum oven until NMR analysis showed a lack of solvents (1.5 hours). Other compounds were prepared in a similar way by using a variety of acids rather than toluenesulfonic acid. Scale up and use of less methanol in the first step generally led to quicker precipitation of salts and a variety of solvents were used rather than ether, as indicated, to help crystallize the individual salts. In some cases the methanol was first removed by evaporation in vacuo. Final drying took between 1.5 hours and several days, depending on the quantity of material and the specific acid used.

Salts of Example 14 that were Prepared

| Example # | Acid Used | Scale: (14 used, g) | Solvent Added | Characterization (melting point, ° C.) |
|---|---|---|---|---|
| 106 | 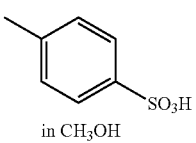 in CH$_3$OH | 1.5 | Ether | 167-168 with decomposition |
| 107 | 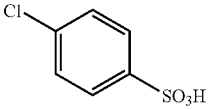 | 0.7 | Ether | 157-159 |
| 108 | H$_3$C-SO$_3$H | 0.6 | Ether | 180-182 with decomposition |
| 109 | C$_2$H$_5$-SO$_3$H | 0.7 | Ether | 153-154 |
| 110 | (HCl)$_2$ * in Ether | 1.5 | Ether | 128-131 with decomposition |
| 111 | HBr | 0.7 | Most MeOH evaporated, then acetone/benzene | 137-139 with decomposition |
| 112 | H$_2$SO$_4$ | 0.6 | Most MeOH evaporated, then acetone/ether | 177-179 with decomposition |
| 113 | HNO$_3$ | 0.5 | Ether | 135 (decomposed) melted 150-152 |
| 114 | 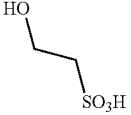 | 0.5 | Ether, Prolonged drying, Hygroscopic | 123-128 |
| 115 | 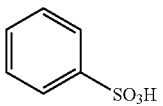 | 4.5 | Ether | 148-149 |

* The disalt with HCl was isolated rather than the 1:1 salt. This occurred even if less than 2 equivalents of acid were used.

Biological Protocols and In Vitro Test Data
KDR Assay:

The cytosolic kinase domain of KDR kinase was expressed as a 6His fusion protein Sf9 insect cells. The KDR kinase domain fusion protein was purified over a Ni++ chelating column. Ninety-six well ELISA plates were coated with 5 µg poly(Glu4;Tyr1) (Sigma Chemical Co., St Louis, Mo.) in 100 µl HEPES buffer (20 mM HEPES; pH 7.5, 150 mM NaCl, 0.02% Thimerosal) at 4° overnight. Before use, the plate was washed with HEPES, NaCl buffer and the plates were blocked with 1% BSA, 0.1% Tween 20 in HEPES, NaCl buffer.

Test compounds were serially diluted in 100% DMSO from 4 mM to 0.12 µM in half-log dilutions. These dilutions were further diluted twenty fold in H2O to obtain compound solutions in 5% DMSO. Following loading of the assay plate with 85 µl of assay buffer (20 mM HEPES, pH 7.5, 100 mM KCl, 10 mM $MgCl_2$, 3 mM $MnCl_2$, 0.05% glycerol, 0.005% Triton X-100, 1 mM-mercaptoethanol, with or without 3.3 µM ATP), 5 µl of the diluted compounds were added to a final assay volume of 100 µl. Final concentrations were between 10 µM, and 0.3 nM in 0.25% DMSO. The assay was initiated by the addition of 10 µl (30 ng) of KDR kinase domain.

The assay was incubated with test compound or vehicle alone with gentle agitation at room temperature for 60 minutes. The wells were washed and phosphotyrosines (PY) were probed with an anti-phosphotyrosine (PY), mAb clone $4G^{10}$ (Upstate Biotechnology, Lake Placid, N.Y.). PY/anti-PY complexes were detected with an anti-mouse IgG/HRP conjugate (Amersham International plc, Buckinghamshire, England). Phosphotyrosine was quantitated by incubating with 100 µl 3,3',5,5' tetramethylbenzidine solution (Kirkegaard and Perry, TMB Microwell 1 Component peroxidase substrate). Color development was arrested by the addition of 100 µl 1% HCl-based stop solution (Kirkegaard and Perry, TMB 1 Component Stop Solution).

Optical densities were determined spectrophotometrically at 450 nm in a 96-well plate reader, SpectraMax 250 (Molecular Devices). Background (no ATP in assay) OD values were subtracted from all ODs and the percent inhibition was calculated according to the equation:

$$\% \text{ Inhibition} = \frac{(OD(\text{vehicle control}) - OD(\text{with compound})) \times 100}{OD(\text{vehicle control}) - OD(\text{no ATP added})}$$

The $IC_{50}$ values were determined with a least squares analysis program using compound concentration versus percent inhibition. Compounds that have $IC_{50} \leq 100$ nM in this assay include those of Examples 1, 2, 4, 6, 8, 9, 10, 11, 12, 13, 14, 16, 17, 18, 19, 20, 22, 23, 24, 34, 37, 38, 39, 40, 42, 43, 44, 47, 49, 51, 52, 53, 54, 56, 57, 59, 60, 62, 63, 65, 66, 68, 69, 70, 71, 72, 73, 74, 75, 78, 82B, 82C, 82D, 85, 88, 93, 96, 97, 98, 101, 102, 103, 104, 105, 106, 107, 108, 109, 110, 111, and 112. Compounds that have $IC_{50}$ values between 100 nM and 1,000 nM include those of examples 3, 5, 7, 21, 27, 28, 35, 36, 45, 46, 48, 50, 55, 58, 61, 64, 67, 76, 79, 82A, 89, 95, 99, and 100. Those that have measured $IC_{50}$ values >1,000 nM include those of examples 26, 29, 30, 31, 32, 33, 41, 77, 80, 81, and 94. Example numbers not in this list may be assumed to be weakly active, with $IC_{50}$ values greater than 1 µM.

Cell Mechanistic Assay-Inhibition of 3T3 KDR Phosphorylation:

$NIH3T^3$ cells expressing the full length KDR receptor were grown in DMEM (Life Technologies, Inc., Grand Island, N.Y.) supplemented with 10% newborn calf serum, low glucose, 25 mM/L sodium pyruvate, pyridoxine hydrochloride and 0.2 mg/ml of G418 (Life Technologies Inc., Grand Island, N.Y.). The cells were maintained in collagen I-coated T75 flasks (Becton Dickinson Labware, Bedford, Mass.) in a humidified 5% CO2 atmosphere at 37° C.

Fifteen thousand cells were plated into each well of a collagen I-coated 96-well plate in the DMEM growth medium. Six hours later, the cells were washed and the medium was replaced with DMEM without serum. After overnight culture to quiesce the cells, the medium was replaced by Dulbecco's phosphate-buffered saline (Life Technologies Inc., Grand Island, N.Y.) with 0.1% bovine albumin (Sigma Chemical Co., St Louis, Mo.). After adding various concentrations (0-300 nM) of test compounds to the cells in 1% final concentration of DMSO, the cells were incubated at room temperature for 30 minutes. The cells were then treated with VEGF (30 ng/ml) for 10 minutes at room temperature. Following VEGF stimulation, the buffer was removed and the cells were lysed by addition of 150 µl of extraction buffer (50 mM Tris, pH 7.8, supplemented with 10% glycerol, 50 mM BGP, 2 mM EDTA, 10 mM NaF, 0.5 mM NaVO4, and 0.3% TX-100) at 4° C. for 30 minutes.

To assess receptor phosphorylation, 100 microliters of each cell lysate was added to the wells of an ELISA plate precoated with 300 ng of antibody C20 (Santa Cruz Biotechnology, Inc., Santa Cruz, Calif.). Following a 60-minute incubation, the plate was washed and bound KDR was probed for phosphotyrosine using an anti-phosphotyrosine mAb clone 4G10 (Upstate Biotechnology, Lake Placid, N.Y.). The plate was washed and wells were incubated with anti-mouse IgG/HRP conjugate (Amersham International plc, Buckinghamshire, England) for 60 minutes. Wells were washed and phosphotyrosine was quantitated by addition of 100 µl per well of 3,3',5,5' tetramethylbenzidine (Kirkegaard and Perry, TMB Microwell 1 Component peroxidase substrate) solution. Color development was arrested by the addition of 100 µl HCl based stop solution (Kirkegaard and Perry, TMB 1 Component Stop Solution).

Optical densities (OD) were determined spectrophotometrically at 450 nm in a 96-well plate reader (SpectraMax 250, Molecular Devices). Background (no VEGF added) OD values were subtracted from all ODs and percent inhibition was calculated according to the equation:

$$\% \text{ Inhibition} = \frac{(OD(VEGF \text{ control}) - OD(\text{with test compound})) \times 100}{OD(VEGF \text{ control}) - OD(\text{no } VEGF \text{ added})}$$

$IC_{50}$s were determined on some of the exemplary materials with a least squares analysis program using compound concentration versus percent inhibition. Compounds that have $IC_{50} \leq 20$ nM in this assay include those of Examples 2, 6, 10, 11, 14, 23, 96, 101, 102, 103, 104, 105. Compounds that have $IC_{50}$ values between 20 nM and 50 nM include those of examples 1, 4, 8, 9, 12, 13, 17, 24, 93, 98. Compounds that have $IC_{50}$ values between 50 nM and 400 nM include those of examples 97, 99, and 100.

Matrigel® Angiogenesis Model:

Preparation of Matrigel Plugs and in vivo Phase: Matrigel® (Collaborative Biomedical Products, Bedford, Mass.) is a basement membrane extract from a murine tumor composed primarily of laminin, collagen IV and heparan sulfate proteoglycan. It is provided as a sterile liquid at 4° C., but rapidly forms a solid gel at 37° C.

Liquid Matrigel at 4° C. was mixed with SK-MEL2 human tumor cells that were transfected with a plasmid containing the murine VEGF gene with a selectable marker. Tumor cells were grown in vitro under selection and cells were mixed with cold liquid Matrigel at a ratio of 2×10⁶ per 0.5 ml. One half milliliter was implanted subcutaneously near the abdominal midline using a 25 gauge needle. Test compounds were dosed as solutions in Ethanol/Cremaphor EL/saline (12.5%:12.5%:75%) at 30, 100, and 300 mg/kg po once daily starting on the day of implantation. Mice were euthanized 12 days post-implantation and the Matrigel pellets were harvested for analysis of hemoglobin content.

Hemoglobin Assay: The Matrigel pellets were placed in 4 volumes (w/v) of 4° C. Lysis Buffer (20 mM Tris pH 7.5, 1 mM EGTA, 1 mM EDTA, 1% Triton X-100 [EM Science, Gibbstown, N.J.], and complete, EDTA-free protease inhibitor cocktail [Mannheim, Germany]), and homogenized at 4° C. Homogenates were incubated on ice for 30 minutes with shaking and centrifuged at 14K×g for 30 minutes at 4° C. Supernatants were transferred to chilled microfuge tubes and stored at 4° C. for hemoglobin assay.

Mouse hemoglobin (Sigma Chemical Co., St. Louis, Mo.) was suspended in autoclaved water (BioWhittaker, Inc, Walkersville, Md.) at 5 mg/ml. A standard curve was generated from 500 micrograms/ml to 30 micrograms/ml in Lysis Buffer (see above). Standard curve and lysate samples were added at 5 microliters/well in duplicate to a polystyrene 96-well plate. Using the Sigma Plasma Hemoglobin Kit (Sigma Chemical Co., St. Louis, Mo.), TMB substrate was reconstituted in 50 mls room temperature acetic acid solution. One hundred microliters of substrate was added to each well, followed by 100 microliters/well of Hydrogen Peroxide Solution at room temperature. The plate was incubated at room temperature for 10 minutes.

Optical densities were determined spectrophotometrically at 600 nm in a 96-well plate reader, SpectraMax 250 Microplate Spectrophotometer System (Molecular Devices, Sunnyvale, Calif.). Background Lysis Buffer readings were subtracted from all wells.

Total sample hemoglobin content was calculated according to the following equation:

Total Hemoglobin=(Sample Lysate Volume)×(Hemoglobin Concentration)

The average Total Hemoglobin of Matrigel samples without cells was subtracted from each Total Hemoglobin Matrigel sample with cells. Percent inhibition was calculated according to the following equation:

% Inhibition =

$$\frac{\text{(Average Total Hemoglobin Drug-Treated Tumor Lysates)}}{\text{(Average Total Hemoglobin Non-Treated Tumor Lysates)}} \times 100$$

Example 8 showed significant activity in this assay at 100 and 300 mg/kg po sid with >60% inhibition of total hemoglobin content of the Matrigel samples from the dosed animals vs. those from vehicle control animals. The other exemplary materials were not tested in this model.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:
1. A compound having the generalized structural formula

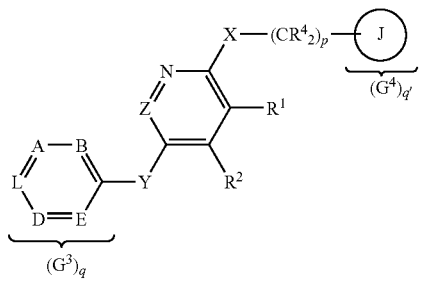

I.
wherein
R¹ and R²
together form a bridge containing two T² moieties and one T³ moiety, said bridge, taken together with the ring to which it is attached, forming a bicyclic of structure

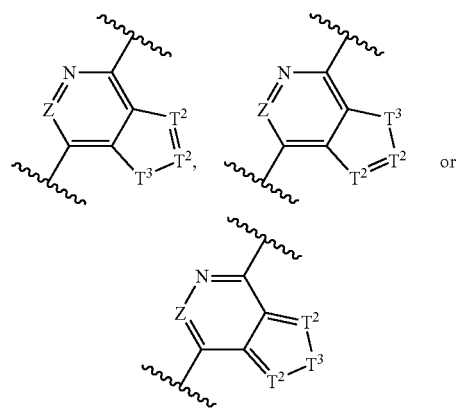

wherein
each T² independently represents CH, or CG¹; and
T³ represents CR⁴G¹ or C(R⁴)₂;
and wherein
G¹ is a substituent independently selected from the group consisting of
—N(R⁶)₂;
—NR³COR⁶;
halogen;
alkyl;
cycloalkyl;
lower alkenyl;
lower cycloalkenyl;
halogen-substituted alkyl;
amino-substituted alkyl;
N-lower alkylamino-substituted alkyl;
N,N-di-lower alkylamino-substituted alkyl;
N-lower alkanoylamino-substituted alkyl;
hydroxy-substituted alkyl;
cyano-substituted alkyl;
carboxy-substituted alkyl;
lower alkoxycarbonyl-substituted alkyl;
phenyl lower alkoxycarbonyl-substituted alkyl;
halogen-substituted alkylamino;
amino-substituted alkylamino;
N-lower alkylamino-substituted alkylamino;

N,N-di-lower alkylamino-substituted alkylamino;
N-lower alkanoylamino-substituted alkylamino;
hydroxy-substituted alkylamino;
cyano-substituted alkylamino;
carboxy-substituted alkylamino;
lower alkoxycarbonyl-substituted alkylamino;
phenyl-lower alkoxycarbonyl-substituted alkylamino;
—$OR^6$;
—$SR^6$;
—$S(O)R^6$;
—$S(O)_2R^6$;
halogenated lower alkoxy;
halogenated lower alkylthio;
halogenated lower alkylsulfonyl;
—$OCOR^6$;
—$COR^6$;
—$CO_2R^6$;
—$CON(R^6)_2$;
—$CH_2OR^3$;
—$NO_2$;
—CN;
amidino;
guanidino;
sulfo;
—B(OH)2;
optionally substituted aryl;
optionally substituted heteroaryl;
optionally substituted saturated heterocyclyl;
optionally substituted saturated heterocyclylalkyl;
optionally substituted partially unsaturated heterocyclyl;
optionally substituted partially unsaturated heterocyclylalkyl;
—$OCO_2R^3$;
optionally substituted heteroarylalkyl;
optionally substituted heteroaryloxy;
—$S(O)_p$ (optionally substituted heteroaryl);
optionally substituted heteroarylalkyloxy;
—$S(O)_p$ (optionally substituted heteroarylalkyl);
—CHO;
—$OCON(R^6)_2$;
—$NR^3CO_2R^6$;
—$NR^3CON(R^6)_2$
$R^3$ is H or lower alkyl;
$R^6$ is independently selected from the group consisting of
H;
alkyl;
cycloalkyl;
optionally substituted aryl; and
optionally substituted aryl lower alkyl;
lower alkyl-$N(R^3)_2$; and
lower alkyl-OH;
$R^4$ is H, halogen, or lower alkyl;
p is 0, 1, or 2;
X is selected from the group consisting of O, S, and $NR^3$;
Y is selected from the group consisting of
lower alkylene;
—$CH_2$—O—;
—$CH_2$—S—;
—$CH_2$—NH—;
—O—;
—S—;
—NH—;
—$(CR^4_2)_n$—$S(O)_p$-(5-membered heteroaryl)-$(CR^4_2)_s$—;
—$(CR^4_2)_n$—$C(G^2)(R^4)$—$(CR^4_2)_s$—;
wherein
n and s are each independently 0 or an integer of 1-2; and
$G^2$ is selected from the group consisting of —CN, —$CO_2R^3$, —$CON(R^6)_2$, and —$CH_2N(R^6)_2$;
—O—$CH_2$—;
—S(O)—;
—$S(O)_2$—;
—$SCH_2$—;
—$S(O)CH_2$—;
—$S(O)_2CH_2$—;
—$CH_2S(O)$—; and
—$CH_2S(O)_2$
Z is N;
q is 0, 1, or 2;
$G^3$ is a monovalent or bivalent moiety selected from the group consisting of:
lower alkyl;
—$NR^3COR^6$;
carboxy-substituted alkyl;
lower alkoxycarbonyl-substituted alkyl;
—$OR^6$;
—$SR^6$;
—$S(O)R^6$;
—$S(O)_2R^6$;
—$OCOR^6$;
—$COR^6$;
—$CO_2R^6$;
—$CH_2OR^3$;
—$CON(R^6)_2$;
—$S(O)_2N(R^6)_2$;
—$NO_2$;
—CN;
optionally substituted aryl;
optionally substituted heteroaryl;
optionally substituted saturated heterocyclyl;
optionally substituted partially unsaturated heterocyclyl;
optionally substituted heteroarylalkyl;
optionally substituted heteroaryloxy;
—$S(O)_p$ (optionally substituted heteroaryl);
optionally substituted heteroarylalkyloxy;
—$S(O)_p$ (optionally substituted heteroarylalkyl);
—$OCON(R^6)_2$;
—$NR^3CO_2R^6$;
—$NR^3CON(R^6)_2$; and
bivalent bridge of structure $T^2$=$T^2$-$T^3$
wherein
each $T^2$ independently represents N, CH, or $CG^{3'}$; and
$T^3$ represents S, O, $CR^4G^{3'}$, $C(R^4)_2$, or $NR^3$; wherein
$G^{3'}$ represents any of the above-defined moieties $G^3$ which are monovalent; and
the terminal $T^2$ is bound to L, and $T^3$ is bound to D, forming a 5-membered fused ring;
A and D independently represent N or CH;
B and E independently represent N or CH;
L represents N or CH; and
with the provisos that
a) the total number of N atoms in the ring containing A, B, D, E, and L is 0, 1, 2, or 3; and
b) when L represents CH and q=0 or any $G^3$ is a monovalent substituent, at least one of A and D is an N atom; and
c) when L represents CH and a $G^3$ is a bivalent bridge of structure $T^2$=$T^2$-$T^3$, then A, B, D, and E are also CH;
J is a ring selected from the group consisting of
aryl;
pyridyl; and
cycloalkyl;
q' represents the number of substituents $G^4$ on ring J and is 0, 1, 2, 3, 4, or 5, and $G^4$ is a monovalent or bivalent moiety selected from the group consisting of
—$N(R^6)_2$;
—$NR^3COR^6$;
halogen;
alkyl;
cycloalkyl;
lower alkenyl;
lower cycloalkenyl;
halogen-substituted alkyl;
amino-substituted alkyl;
N-lower alkylamino-substituted alkyl;
N,N-di-lower alkylamino-substituted alkyl;
N-lower alkanoylamino-substituted alkyl;
hydroxy-substituted alkyl;
cyano-substituted alkyl;
carboxy-substituted alkyl;
lower alkoxycarbonyl-substituted alkyl;
phenyl lower alkoxycarbonyl-substituted alkyl;
halogen-substituted alkylamino;
amino-substituted alkylamino;
N-lower alkylamino-substituted alkylamino;
N,N-di-lower alkylamino-substituted alkylamino;
N-lower alkanoylamino-substituted alkylamino;
hydroxy-substituted alkylamino;
cyano-substituted alkylamino;
carboxy-substituted alkylamino;
lower alkoxycarbonyl-substituted alkylamino;
phenyl-lower alkoxycarbonyl-substituted alkylamino;
—$OR^6$;
—$SR^6$;
—$S(O)R^6$;
—$S(O)_2R^6$;
halogenated lower alkoxy;
halogenated lower alkylthio;
halogenated lower alkylsulfonyl;
—$OCOR^6$;
—$COR^6$;
—$CO_2R^6$;
—$CON(R^6)_2$;
—$CH_2OR^3$;
—$NO_2$;
—$CN$;
amidino;
guanidino;
sulfo;
—$B(OH)2$;
optionally substituted aryl;
optionally substituted heteroaryl;
optionally substituted saturated heterocyclyl;
optionally substituted partially unsaturated heterocyclyl;
—$OCO_2R^3$;
optionally substituted heteroarylalkyl;
optionally substituted heteroaryloxy;
—$S(O)_p$ (optionally substituted heteroaryl);
optionally substituted heteroarylalkyloxy;
—$S(O)_p$ (optionally substituted heteroarylalkyl);
—CHO;
—$OCON(R^6)_2$;
—$NR^3CO_2R^6$;
—$NR^3CON(R^6)_2$; and
  fused ring-forming bivalent bridges attached to and connecting adjacent positions of ring J, said bridges having the structures:

a)

wherein
  each $T^2$ independently represents N, CH, or $CG^{4'}$;
  $T^3$ represents S, O, $CR^4G^{4'}$, $C(R^4)_2$, or $NR^3$;
  wherein
    G4' represents any of the above-defined moieties $G^4$ which are monovalent; and
  binding to ring J is achieved via terminal atoms $T^2$ and $T^3$;

b)

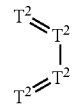

wherein
  each $T^2$ independently represents N, CH, or $CG^{4'}$;
  wherein
    G4' represents any of the above-defined moieties $G^4$ which are monovalent; and
  with the proviso that a maximum of two bridge atoms $T^2$ may be N; and
  binding to ring J is achieved via terminal atoms $T^2$; and c)

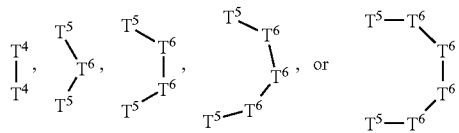

wherein
  each $T^4$, $T^5$, and $T^6$ independently represents O, S, $CR^4G^{4'}$, $C(R^4)_2$, or $NR^3$;
  wherein
    G4' represents any of the above-defined moieties $G^4$ which are monovalent; and
  binding to ring J is achieved via terminal atoms $T^4$ or $T^5$;
  with the provisos that:
    i) when one $T^4$ is O, S, or $NR^3$, the other $T^4$ is $CR^4G^{4'}$ or $C(R^4)_2$;
    ii) a bridge comprising $T^5$ and $T^6$ atoms may contain a maximum of two heteroatoms O, S, or N; and
    iii) in a bridge comprising $T^5$ and $T^6$ atoms, when one $T^5$ group and one $T^6$ group are O atoms, or two $T^6$ groups are O atoms, said O atoms are separated by at least one carbon atom;
when $G^4$ is an alkyl group located on ring J adjacent to the linkage —$(CR^4{}_2)_p$—, and X is $NR^3$ wherein $R^3$ is an alkyl substituent, then $G^4$ and the alkyl substituent $R^3$ on X may be joined to form a bridge of structure —$(CH_2)_{p'}$— wherein p' is 2, 3, or 4, with the proviso that the sum of p and p' is 2, 3, or 4, resulting in formation of a nitrogen-containing ring of 5, 6, or 7 members;
and with the further provisos that:
in $G^1, G^2, G^3$, and $G^4$, when two groups $R^3$ or $R^6$ are each alkyl and located on the same N atom they may be linked by a bond, an O, an S, or $NR^3$ to form a N-containing heterocycle of 5-7 ring atoms;
when an aryl, heteroaryl, or heterocyclyl ring is optionally substituted, that ring may bear up to 5 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —$CO_2R^3$, —CHO, —$CH_2OR^3$, —$OCO_2R^3$, —$CON(R^6)_2$, —$OCON(R^6)_2$, —$NR^3CON(R^6)_2$, nitro, amidino, guanidino, mercapto, sulfo, and cyano; and
when any alkyl group is attached to O, S, or N, and bears a hydroxyl substituent, then said hydroxyl substituent is separated by at least two carbon atoms from the O, S, or N to which the alkyl group is attached,
or a pharmaceutically acceptable salt or prodrug thereof.

2. A compound of claim 1 wherein
$R^1$ and $R^2$
together form a bridge containing two $T^2$ moieties and one $T^3$ moiety, said bridge, taken together with the ring to which it is attached, forming a bicyclic of structure

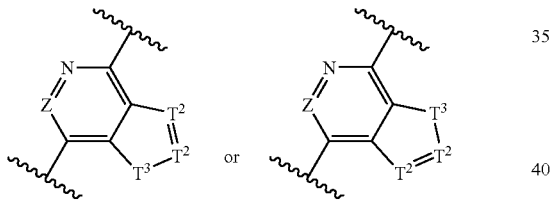

wherein
each $T^2$ independently represents CH, or $CG^1$; and $T^3$ represents $CH_2$.

3. A pharmaceutical composition comprising a compound of claim 1 and a pharmaceutically acceptable carrier.

4. A compound having the generalized structural formula

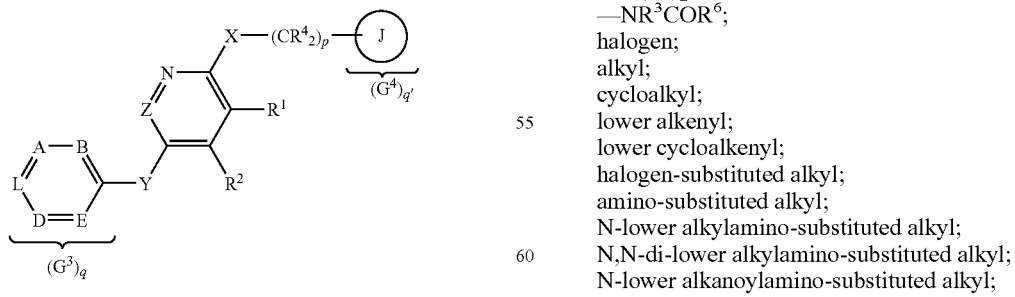

II.
wherein
$R^1$ and $R^2$:
i)
ii) together form a bridge of structure

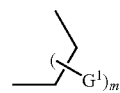

wherein binding is achieved via the terminal carbon atoms;
iii) together form a bridge of structure

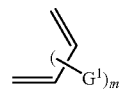

wherein binding is achieved via the terminal carbon atoms;
or
v) together form a bridge containing two $T^2$ moieties and one $T^3$ moiety, said bridge, taken together with the ring to which it is attached, forming a bicyclic of structure

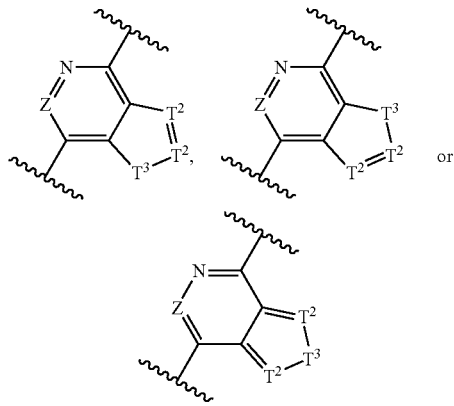

wherein
each $T^2$ independently represents CH, or $CG^1$; and $T^3$ represents $CR^4G^1$, or $C(R^4)_2$;
and wherein
m is 0 or an integer 1-4; and
$G^1$ is a substituent independently selected from the group consisting of
—$N(R^6)_2$;
—$NR^3COR^6$;
halogen;
alkyl;
cycloalkyl;
lower alkenyl;
lower cycloalkenyl;
halogen-substituted alkyl;
amino-substituted alkyl;
N-lower alkylamino-substituted alkyl;
N,N-di-lower alkylamino-substituted alkyl;
N-lower alkanoylamino-substituted alkyl;
hydroxy-substituted alkyl;
cyano-substituted alkyl;
carboxy-substituted alkyl;
lower alkoxycarbonyl-substituted alkyl;
phenyl lower alkoxycarbonyl-substituted alkyl;
halogen-substituted alkylamino;

amino-substituted alkylamino;
N-lower alkylamino-substituted alkylamino;
N,N-di-lower alkylamino-substituted alkylamino;
N-lower alkanoylamino-substituted alkylamino;
hydroxy-substituted alkylamino;
cyano-substituted alkylamino;
carboxy-substituted alkylamino;
lower alkoxycarbonyl-substituted alkylamino;
phenyl-lower alkoxycarbonyl-substituted alkylamino;
—$OR^6$;
—$SR^6$;
—$S(O)R^6$;
—$S(O)_2R^6$;
halogenated lower alkoxy;
halogenated lower alkylthio;
halogenated lower alkylsulfonyl;
—$OCOR^6$;
—$COR^6$;
—$CO_2R^6$;
—$CON(R^6)_2$;
—$CH_2OR^3$;
—$NO_2$;
—CN;
amidino;
guanidino;
sulfo;
—B(OH)2;
optionally substituted aryl;
optionally substituted heteroaryl;
optionally substituted saturated heterocyclyl;
optionally substituted saturated heterocyclylalkyl;
optionally substituted partially unsaturated heterocyclyl;
optionally substituted partially unsaturated heterocyclylalkyl;
—$OCO_2R^3$;
optionally substituted heteroarylalkyl;
optionally substituted heteroaryloxy;
—$S(O)_p$ (optionally substituted heteroaryl);
optionally substituted heteroarylalkyloxy;
—$S(O)_p$ (optionally substituted heteroarylalkyl);
—CHO;
—$OCON(R^6)_2$;
—$NR^3CO_2R^6$;
—$NR^3CON(R^6)_2$
$R^3$ is H or lower alkyl;
$R^6$ is independently selected from the group consisting of
H;
alkyl;
cycloalkyl;
optionally substituted aryl; and
optionally substituted aryl lower alkyl;
lower alkyl-$N(R^3)_2$; and
lower alkyl-OH;
$R^4$ is H, halogen, or lower alkyl;
p is 0, 1, or 2;
X is selected from the group consisting of O, S, and $NR^3$;
Y is selected from the group consisting of
lower alkylene;
—$CH_2$—O—;
—$CH_2$—S—;
—$CH_2$—NH—;
—O—;
—S—;
—NH—;
—$(CR^4_2)_n$—$S(O)_p$-(5-membered heteroaryl)-$(CR^4_2)_s$—;
—$(CR^4_2)_n$—$C(G^2)(R^4)$—$(CR^4_2)_s$—;
wherein
n and s are each independently 0 or an integer of 1-2; and
$G^2$ is selected from the group consisting of —CN, —$CO_2R^3$, —$CON(R^6)_2$, and —$CH_2N(R^6)_2$;
—O—$CH_2$—;
—S(O)—;
—$S(O)_2$—;
—$SCH_2$—;
—$S(O)CH_2$—;
—$S(O)_2CH_2$—;
—$CH_2S(O)$—; and
—$CH_2SO_2$
Z is N;
q is 1 or 2;
$G^3$ is a monovalent or bivalent moiety selected from the group consisting of
lower alkyl;
—$NR^3COR^6$;
carboxy-substituted alkyl;
lower alkoxycarbonyl-substituted alkyl;
—$OR^6$;
—$SR^6$;
—$S(O)R^6$;
—$S(O)_2R^6$;
—$OCOR^6$;
—$COR^6$;
—$CO_2R^6$;
—$CH_2OR^3$;
—$CON(R^6)_2$;
—$S(O)_2N(R^6)_2$;
—$NO_2$;
—CN;
optionally substituted aryl;
optionally substituted heteroaryl;
optionally substituted saturated heterocyclyl;
optionally substituted partially unsaturated heterocyclyl;
optionally substituted heteroarylalkyl;
optionally substituted heteroaryloxy;
—$S(O)_p$ (optionally substituted heteroaryl);
optionally substituted heteroarylalkyloxy;
—$S(O)_p$ (optionally substituted heteroarylalkyl);
—$OCON(R^6)_2$;
—$NR^3CO_2R^6$;
—$NR^3CON(R^6)_2$; and
bivalent bridge of structure $T^2$=$T^2$-$T^3$:
wherein
each $T^2$ independently represents N, CH, or $CG^{3'}$; and
$T^3$ represents S, O, $CR^4G^{3'}$, $C(R^4)_2$, or $NR^3$; wherein
$G^{3'}$ represents any of the above-defined moieties G3 which are monovalent; and
the terminal $T^2$ is bound to L, and $T^3$ is bound to D, forming a 5-membered fused ring;
A and D are CH;
B and E are CH;
L is CH;
with the proviso that the resulting phenyl ring bears as a $G^3$ substituent said bivalent bridge of structure $T^2$=$T^2$-$T^3$;
J is a ring selected from the group consisting of
aryl;
pyridyl; and
cycloalkyl;
q' represents the number of substituents $G^4$ on ring J and is 0, 1, 2, 3, 4, or 5, and
$G^4$ is a monovalent or bivalent moiety selected from the group consisting of —N(R⁶)₂;
—NR³COR⁶;
halogen;
alkyl;
cycloalkyl;
lower alkenyl;
lower cycloalkenyl;
halogen-substituted alkyl;
amino-substituted alkyl;
N-lower alkylamino-substituted alkyl;
N,N-di-lower alkylamino-substituted alkyl;
N-lower alkanoylamino-substituted alkyl;
hydroxy-substituted alkyl;
cyano-substituted alkyl;
carboxy-substituted alkyl;
lower alkoxycarbonyl-substituted alkyl;
phenyl lower alkoxycarbonyl-substituted alkyl;
halogen-substituted alkylamino;
amino-substituted alkylamino;
N-lower alkylamino-substituted alkylamino;
N,N-di-lower alkylamino-substituted alkylamino;
N-lower alkanoylamino-substituted alkylamino;
hydroxy-substituted alkylamino;
cyano-substituted alkylamino;
carboxy-substituted alkylamino;
lower alkoxycarbonyl-substituted alkylamino;
phenyl-lower alkoxycarbonyl-substituted alkylamino;
—OR⁶;
—SR⁶;
—S(O)R⁶;
—S(O)₂R⁶;
halogenated lower alkoxy;
halogenated lower alkylthio;
halogenated lower alkylsulfonyl;
—OCOR⁶;
—COR⁶;
—CO₂R⁶;
—CON(R⁶)₂;
—CH₂OR³;
—NO₂;
—CN;
amidino;
guanidino;
sulfo;
—B(OH)2;
optionally substituted aryl;
optionally substituted heteroaryl;
optionally substituted saturated heterocyclyl;
optionally substituted partially unsaturated heterocyclyl;
—OCO₂R³;
optionally substituted heteroarylalkyl;
optionally substituted heteroaryloxy;
—S(O)$_p$ (optionally substituted heteroaryl);
optionally substituted heteroarylalkyloxy;
—S(O)$_p$ (optionally substituted heteroarylalkyl);
—CHO;
—OCON(R⁶)₂;
—NR³CO₂R⁶;
—NR³CON(R⁶)₂; and
fused ring-forming bivalent bridges attached to and connecting adjacent positions of ring J, said bridges having the structures:

a)

wherein
each T² independently represents N, CH, or CG⁴';
T³ represents S, O, CR⁴G⁴', C(R⁴)₂, or NR³;
wherein
G⁴' represents any of the above-defined moieties G⁴ which are monovalent; and
binding to ring J is achieved via terminal atoms T² and T³;

b)

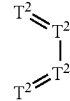

wherein
each T² independently represents N, CH, or CG⁴';
wherein
G4' represents any of the above-defined moieties G⁴ which are monovalent; and
with the proviso that a maximum of two bridge atoms T² may be N; and
binding to ring J is achieved via terminal atoms T²; and c)

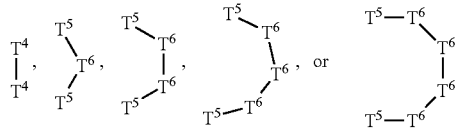

wherein
each T⁴, T⁵, and T⁶ independently represents O, S, CR⁴G⁴', C(R⁴)₂, or NR³;
wherein
G4' represents any of the above-identified moieties G4 which are monovalent; and
binding to ring J is achieved via terminal atoms T⁴ or T⁵;
with the provisos that:
i) when one T⁴ is O, S, or NR³, the other T⁴ is CR⁴G⁴' or C(R⁴)₂;
ii) a bridge comprising T⁵ and T⁶ atoms may contain a maximum of two heteroatoms O, S, or N; and
iii) in a bridge comprising T⁵ and T⁶ atoms, when one T⁵ group and one T⁶ group are O atoms, or two T⁶ groups are O atoms, said O atoms are separated by at least one carbon atom;
when G⁴ is an alkyl group located on ring J adjacent to the linkage —(CR⁴₂)$_p$—, and X is NR³ wherein R³ is an alkyl substituent, then G⁴ and the alkyl substituent R³ on X may be joined to form a bridge of structure —(CH₂)$_{p'}$— wherein p' is 2, 3, or 4, with the proviso that the sum of p and p' is 2, 3, or 4, resulting in formation of a nitrogen-containing ring of 5, 6, or 7 members;
and with the further provisos that:

in $G^1$, $G^2$, $G^3$, and $G^4$, when two groups $R^3$ or $R^6$ are each alkyl and located on the same N atom they may be linked by a bond, an O, an S, or $NR^3$ to form a N-containing heterocycle of 5-7 ring atoms;

when an aryl, heteroaryl, or heterocyclyl ring is optionally substituted, that ring may bear up to 5 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —$CO_2R^3$, —CHO, —$CH_2OR^3$, —$OCO_2R^3$, —$CON(R^6)_2$, —$OCON(R^6)_2$, —$NR^3CON(R^6)_2$, nitro, amidino, guanidino, mercapto, sulfo, and cyano; and when any alkyl group is attached to O, S, or N, and bears a hydroxyl substituent, then said hydroxyl substituent is separated by at least two carbon atoms from the O, S, or N to which the alkyl group is attached, or a pharmaceutically acceptable salt or prodrug thereof.

5. A compound of claim 4 wherein, in the ring comprising A, B, D, E, and L and a bivalent bridge of structure $T^2$=T2-$T^3$, the terminal $T^2$ represents N and the $T^3$ unit of said bridge represents S, O, $CR^4_2$, or $NR^3$.

6. A pharmaceutical composition comprising a compound of claim 4 and a pharmaceutically acceptable carrier.

7. A compound selected from the group consisting of

| Ex. No.: | Compound Name (IUPAC): |
|---|---|
| 93 | N-(1,3-benzothiazol-6-yl)-N-[4-(1,3-benzothiazol-6-ylamino)-1-phthalaziny]amine |
| 95 | N-(1H-benzimidazol-6-yl)-N-{4-[(4-chlorophenyl)amino]-1-phthalazinyl}amine |
| 96 | N-(1H-1,2,3-benzotriazol-5-yl)-N-{4-[(4-chlorophenyl)amino]-1-phthalazinyl}amine |
| 97 | N-(1,3-benzothiazol-6-yl)-4-(5-bromo-2,3-dihydro-1H-indol-1-yl)-1-phthalazinamine |
| 98 | N-(1,3-benzothiazol-6-yl)-N-{4-[(2,2-difluoro-1,3-benzodioxol-5-yl)amino]-1-phthalazinyl}amine |
| 99 | N-(1,3-benzothiazol-6-yl)-N-(4-{[4-(1-piperidinyl)phenyl]amino}-1-phthalazinyl)amine |
| 100 | N-(1,3-benzothiazol-6-yl)-N-[4-({4-[ethyl(isopropyl)amino]phenyl}amino)-1-phthalazinyl]amine |
| 101 | N-(1,3-benzothiazol-6-yl)-N-{4-[(3-bromophenyl)amino]-1-phthalazinyl}amine |
| 102 | N-(1,3-benzothiazol-6-yl)-N-{4-[(4-isopropylphenyl)amino]-1-phthalazinyl}amine |
| 103 | N-(1,3-benzothiazol-6-yl)-N-{4-[(3-methoxyphenyl)amino]-1-phthalazinyl}amine |
| 104 | N-(1,3-benzothiazol-6-yl)-N-{4-[(3-fluoro-4-methylphenyl)amino]-1-phthalazinyl}amine |
| 105 | N-(1,3-benzothiazol-6-yl)-N-{4-[(4-chlorophenyl)amino]-1-phthalazinyl}amine. |

* * * * *